(12) United States Patent
Gudas et al.

(10) Patent No.: US 7,687,606 B2
(45) Date of Patent: Mar. 30, 2010

(54) ANTIBODIES DIRECTED TO MONOCYTE CHEMO-ATTRACTANT PROTEIN-1 (MCP-1) AND USES THEREOF

(75) Inventors: Jean M. Gudas, Pacific Palisades, CA (US); Mary Haak-Frendscho, Newark, CA (US); Orit Foord, Foster-City, CA (US); Meina L. Liang, Danville, CA (US); Kiran Ahluwalia, Fremont, CA (US); Sunil Bhakta, Hayward, CA (US)

(73) Assignee: AstraZeneca AB, Sodertalje (SE)

( * ) Notice: Subject to any disclaimer, the term of this patent is extended or adjusted under 35 U.S.C. 154(b) by 86 days.

(21) Appl. No.: 11/641,633

(22) Filed: Dec. 19, 2006

(65) Prior Publication Data

US 2007/0116708 A1 May 24, 2007

Related U.S. Application Data

(62) Division of application No. 10/644,277, filed on Aug. 19, 2003, now Pat. No. 7,202,343.

(60) Provisional application No. 60/404,802, filed on Aug. 19, 2002.

(51) Int. Cl.
*C07K 14/00* (2006.01)
*A61K 39/395* (2006.01)
*C12P 21/00* (2006.01)

(52) U.S. Cl. .................. 530/387.7; 424/130.1; 435/70.1

(58) Field of Classification Search ..................... None
See application file for complete search history.

(56) References Cited

U.S. PATENT DOCUMENTS

2004/0047860 A1  3/2004  Hiestand et al.

FOREIGN PATENT DOCUMENTS

| WO | WO 01/89565 | 11/2001 |
|----|-------------|---------|
| WO | WO 02/02640 | 1/2002  |

OTHER PUBLICATIONS

Rudikoff et al (Proc Natl Acad Sci USA 1982 vol. 79 p. 1979).*
Panka et al (Proc Natl Acad Sci USA vol. 85 3080-3084 May 1988).*
Amit et al Science vol. 233 747-753 1986.*
Bradwell et al., "Control of hypercalcaemia of parathyroid carcinoma by immunisation," *Lancet*, 353: 370-373 (1999).
Hemmerich et al., "Identification of Residues in the Monocyte Chemotactic Protein-1 That Contact the MCP-1 Receptor, CCR2," *Biochemistry*, 38: 13013-13025 (1999).
Jarnagin et al., "Identification of Surface Residues of the Monocyte Chemotactic Protein 1 That Affect Signaling through the Receptor CCR2," *Biochemistry*, 38: 16167-16177 (1999).
Logue et al., "Production and characterisation of monoclonal antibodies to parathyroid hormone (1-34)," *J. Immunol. Methods*, 137: 159-166 (1991).
Magerlein et al., "Production of Sequence Specific Polyclonal Antibodies to Human Parathyroid Hormone 1-37 by Immunization with Multiple Antigenic Peptides," *Drug Res.*, 48: 783-787 (1998).
Vieira et al., "Monoclonal Antibodies to Bovine Parathyroid Hormone: Production and Characterization," *Braz. J. Med. Biol. Res.*, 21: 1005-1011 (1988).
Visser et al., "Production and Characterization of Antisera to Synthetic 1-34 Human Parathyroid Hormone Fragments: Possible Implications for the Correctness of Proposed Structures," *Acta Endocrinol.*, 90: 90-102 (1979).
PCT International Search Report, International Application No. PCT/US03/26232.
Patent Abstracts of Japan. vol. 1999, No. 8 (1999). 11 06052, Teijin Ltd.
Patent Abstracts of Japan. vol. 1997, No. 7 (1997). 09 067399, Mitsui Toatsu Chem. Inc.
Kaji et al. "Analysis of peptide motifs recognized with anti-MCP-1 monoclonal antibody." *Peptide Science*. 33-36 (1999).
Yoshimura et al. "Production and characterization of mouse monoclonal antibodies against human monocyte chemoattractant protein-1." *Journal of Immunology*. 147(7):2229-2233 (1991).
Zhang et al. "Structure/activity analysis of human monocyte chemoattractant protein-1 (MCP-1) by mutagenesis. Identification of a mutated protein that inhibits MCP-1 mediated protein that inhibits MCP-1 mediated monocyte chemotaxis." *Journal of Biological Chemistry*. 269(22):15918-159924 (2003).
Stancoviski et al. (Proceedings of the Natioanl Academyh of Science3 USA. 1991;88:8691-8695).
Jiang et al. (J.Biol.Chem. Feb. 11, 2005;280(6):4656-4662).
Reimer et al. (Mol.Immunol. 2005;42:1121-1124).

* cited by examiner

*Primary Examiner*—Christopher H Yaen

(57) ABSTRACT

Embodiments of the invention described herein relate to antibodies directed to the antigen monocyte chemo-attractant protein-1 (MCP-1) and uses of such antibodies. In particular, in accordance with some embodiments, there are provided fully human monoclonal antibodies directed to the antigen MCP-1. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDRs), specifically from FR1 through FR4 or CDR1 through CDR3, are provided. Hybridomas or other cell lines expressing such immunoglobulin molecules and monoclonal antibodies are also provided.

33 Claims, 15 Drawing Sheets

Figure 7A

Alignment of sequences using VH1-24

```
                                                      CDR1                      CDR2
                                                      ----                      ----
VH1-24          QVQLVQSGAEVKKPGASVKVSCKVSGYTLTELSMHWVRQAPGKGLEWMGGFDPEDGETIY
MCP1-1.1.1_HC   QVQLVQSGAEVKKPGASVKVSCKVSGYTLTELSMHWVRQAPGNGLEWMGGFDPEDGETIY
MCP1-1.10_HC    QVQLVQSGAEVKKPGASVKVSCKVSGYTLTELSMHWVRQAPGKGLEWMGGFDPEDGETIY
MCP1-1.11_HC    QVQVVQSGAEVKNPGASVKVSCKVSGSTLTELSMHWVRQAPGKGLEWMGGFDPEDGETIY
MCP1-1.12_HC    QVQLVQSGAEVKKPGASVKVSCKVSGYTLTELSMHWVRQAPGKGLEWMGGFDPEDGETIY
MCP1-1.13_HC    QVQLVQSGAEVKKPGASVKVSCKVSGHTLTELSMHWVRQAPGKGLEWMGGFDPEDDETIY
MCP1-1.18_HC    QVQLVQSGAEVKKPGASVKVSCKVSGYTLTELSMHWVRQAPGKGLEWMGGFDPEDGETIY
MCP1-1.2_HC     QVQLVQSGAEVKKPGASVKVSCKVSGYTFTELSMHWVRQAPGKGLEWMGGFDPEDGETSY
MCP1-1.3_HC     QVQLVQSGAEVKKPGASVKVSCKVSGYTLTELSMHWVRRIPGKGLEWMGGFDPEDGETIY
MCP1-1.5.1_HC   QVQLVQSGAEVKKPGASVKVSCKVSGYTLTELSMHWVRQAPGKGLEWMGGFDPEDDETIY
MCP1-1.6_HC     QVQLVQSGAEVKKPGASVKVSCKVSGYTLTELSMHWVRQAPGKGLEWMGGFDPEDGETIY
MCP1-1.7_HC     QVQLVQSGAEVKKPGASVKVSCKVSGYTLTELSMHWVRQAPGKGLEWMGGFDPEDGETIY
MCP1-1.8_HC     QVQLVQSGAEVKKPGASVKVSCKVSGHIFTELSIHWVRQAPGKGLEWMGGFDPEDGETIY
MCP1-1.9_HC     QVQLVQSGAEVKKPGASVKVSCKVSGYTLTELSMHWVRQAPGKGLEWMGGFDPEDGETIN
MCP1-2.3_HC     QVQLVQSGAEVKKPGASVKVSCKVSGYTLTELSMHWVRQAPGKGLEWMGGFDPEDDETIY
MCP1-3.10_HC    QVQLVQSGAEVKKPGASVKVSCKVSGYTLTELSMHWVRQAPGKGLEWMGGFDPEDGETIY
MCP1-3.15_HC    QVQLVQSGAEVKKPGASVQVSCKVSGDTLTELSMHWVRQAPGKGLEWMGGFDPEDGETIY
MCP1-3.16_HC    QVQLVQSGAEVKKPGASVKVSCKVSGYTLTDLSMHWVRQAPGKGLEWMGGFDPEDGETIY
MCP1-3.2_HC     QVQLVQSGAEVKKPGASVKVSCKVSGYTLSELSMHWVRQAPGKGLEWMGGFDPEDGEIIH
MCP1-3.4_HC     QVQLVQSGAEVKKPGASVKVSCKVSGYTLTELSMHWVRQAPGKGLEWMGGFDPEDGETMY
MCP1-3.5_HC     QVQLVQSGAEVKKPGASVKVSCKVSGYTLSELSMHWVRQAPGKGLEWMGGFDPEDDETIY
MCP1-3.6_HC     QVQLVQSGAEVKKPGASVKVSCKVSGYTLTELSMHWVRQAPGKGLEWMGGFDPEDGETIY
MCP1-3.7_HC     QVQLVQSGAEVKKPGASVKVSCKVSGYTLTELSMHWVRQTPGKGLEWMGGFDPEDGETIY
MCP1-3.8_HC     QVQLVQSGAEVKKPGASVKVSCKVSGYTLTELSMHWVRQAPGKGLEWMGGFDPENGETIH
MCP1-4.5_HC     QVQLVQSGAEVKKPGASVKVSCKVSGYTLTELSMHWVRQAPGKGLEWMGGFDPEDGETIY
MCP1-4.6.3_HC   QVQLVQSGAEVKKPGASVKVSCKVSGYTLTELSMHWVRQAPGKGLEWMGGFDPEDGETIY
MCP1-4.7_HC     QVQLVQSGAEVKKPGASVKVSCKVSGYTLTELSMHWVRQAPGKGLEWMGGFDPEDGETIY
MCP1-5.3_HC     QVQLVQSGAEVKKPGASVKVSCKVSGYTLSELSMHWVRQAPGKGLEWMGGFDPEDGETIY
MCP1-4.8.1_HC   QVQLVQSGAEVKKPGASVKVSCKVSGYTLTELSMHWVRQAPGKGLEWMGGFDPEDGETIY
```

Figure 7A (cont.)

```
                         CDR2                                          CDR3
VH1-24          AQKFQGRVTMTEDTSTDTAYMELSSLRSEDTAVYYCAT-------------------
MCP1-1.1.1_HC   AQRFQGRVVMTEDPSTDTAYMELSSLRSEDTAVYYCATNEFWSGYF-----DYWGQGTLV
MCP1-1.10_HC    AQKFQGRVTMTEDTSTDTAYMELSSLRSEDTAVYYCATNEFWSGYF-----DYWGQGTLV
MCP1-1.11_HC    AQKFQGRVTMTEDTSTDTVYMELSSLRSEDTAVYYCATNDFWSGYF-----DYWGQGTLV
MCP1-1.12_HC    AQKFQGRVTMTEDTSTDTAYMELSSLRSEDTAVYYCATNDFWSGYY-----NYWGQGTLV
MCP1-1.13_HC    AQKFQDRVTMTEDTSTDTAYMELSSLRSEDTAVYYCATNDFWSGYF-----DCWGQGTLV
MCP1-1.18_HC    AQKFQGRVTMTEDTSTDTVYMELSSLRSEDTAMYYCATREFWTGYF-----DHWGQGTLV
MCP1-1.2_HC     AQKFRGRVTMTEDTSTDTAHMELSSLRSEDTAVYYCATNDFWSGYF-----DYWGQGTLV
MCP1-1.3_HC     AQKFQGRVTMTEDTSTDTAYMELSSLRSEDTAVYYCATNDFWSGYW-----GHWGQGTLV
MCP1-1.5.1_HC   AQKFQGRVTMTEDTSTDTAYMELSSLRSEDTAVYFCATNDFWSGYF-----DCWDQGTLV
MCP1-1.6_HC     AQKFQGRVTMTEDTSTDTAYMELSSLRSEDTAVYYCATWYSGIYLAF----DIWGQGTMV
MCP1-1.7_HC     AQKFQGRVSMTEDTSTDTAYMELSSLRSEDTAVYFCATNEFWSGYF-----DYWGQGTLV
MCP1-1.8_HC     AQKFQGRVTMTEDTSTDTVYMELSSLRSEDTAVYYCATNDFWSGYF-----DYWGQGTLV
MCP1-1.9_HC     AQKFQGRVTMTEDTSTDTGYMELSSLRSEDTAVYYCATDPGGYSGYF----DHWGQGTLV
MCP1-2.3_HC     AQKFQGRVTMTEDTSTHTAYMELSSLRSEDTAVYYCATHDFWSAYF-----YYWGQGTLV
MCP1-3.10_HC    AQKFQGRVMMTEDTSTDTAFMDLSSLRSEDTAVYYCATDDMLTPHYLYFGMDVWGQGTTV
MCP1-3.15_HC    ARKFQGRVTMTEDTSTDTVYMELSSLRSEDTAVYFCATDSRGYSGYF----DNWGQGTLV
MCP1-3.16_HC    AQKFQGRVTMTEDTSSDTAYMELSSLRSEDTAVYYCATHEFWSGYF-----DYWGQGTLV
MCP1-3.2_HC     AQKFQGRVTMTEDTSTDTAYMELSSLRSEDTAVYYCATGDFWSGYYL----DWWGQGTLV
MCP1-3.4_HC     AQKFQGRVTMTEDTSTDTAYMELSSLRSEDTAVYYCATDDFWSGYF-----DYWGQGTLV
MCP1-3.5_HC     AQKFQGRVTMTEDTSTDTAFMELSSLRSEDTAVYYCATHDFWSGYF-----HYWGQGTLV
MCP1-3.6_HC     AQKFQGRVTMTEDTSTDTAYMELSSLRSEDTAVYYCAIHEFWSGYF-----DYWGQGTLV
MCP1-3.7_HC     AQKFQDRVTMTEDTSTDTAYMELSSLRSEDTAVYYCATNDFWTGYY-----DYWGQGTLV
MCP1-3.8_HC     AQKFQGRVIMTEDTSTDTAYMELSSLRSEDTAVYYCATDQGGYSGYF----DCWGQGTLV
MCP1-4.5_HC     AQKFQGRVTMTEDTSTDTAYMELSSLRSEDTAVYYCATDDFWSGYF-----DYWGQGTLV
MCP1-4.6.3_HC   AQKFQGRVTMTEDTSTDTAYMELSSLRSEDTAVYYCATDDFWSGYF-----DYWGQGTLV
MCP1-4.7_HC     AQKFQGRVTMTEDTSTDTAYMELSSLRSEDTAVYYCATDDFWSGYF-----DYWGQGTLV
MCP1-5.3_HC     AQKFQGRVTMTEDTSTDTAYMELSSLRSEDTAVFYCATKREYSGYF-----DYWGQGTLV
MCP1-4.8.1_HC   AQKFQGRVTMTEDTSTDTAYMELSSLRTEDTAVYYCTTDDFWSGYF-----DYWGQGTLV
```

Figure 7A (cont.)

| | |
|---|---|
| VH1-24 | --- |
| MCP1-1.1.1_HC | VSS |
| MCP1-1.10_HC | VSS |
| MCP1-1.11_HC | VSS |
| MCP1-1.12_HC | VSS |
| MCP1-1.13_HC | VSS |
| MCP1-1.18_HC | VSS |
| MCP1-1.2_HC | VSS |
| MCP1-1.3_HC | VSS |
| MCP1-1.5.1_HC | VSS |
| MCP1-1.6_HC | VSS |
| MCP1-1.7_HC | VSS |
| MCP1-1.8_HC | VSS |
| MCP1-1.9_HC | VSS |
| MCP1-2.3_HC | VSS |
| MCP1-3.10_HC | VSS |
| MCP1-3.15_HC | VSS |
| MCP1-3.16_HC | VSS |
| MCP1-3.2_HC | VSS |
| MCP1-3.4_HC | VSS |
| MCP1-3.5_HC | VSS |
| MCP1-3.6_HC | VSS |
| MCP1-3.7_HC | VSS |
| MCP1-3.8_HC | VSS |
| MCP1-4.5_HC | VSS |
| MCP1-4.6.3_HC | VSS |
| MCP1-4.7_HC | VSS |
| MCP1-5.3_HC | VSS |
| MCP1-4.8.1_HC | VSS |

Figure 8A

Alignment of sequences using VK-B3

```
                              CDR1                    CDR2
                              ━━━━━━━━━━━━            ━━━━

VK-B3            DIVMTQSPDSLAVSLGERATINCKSSQSVLYSSNNKNYLAWYQQKPGQPPKLLIYWASTR
MCP1-1.1.1_LC    DIVMTQSPDSLAMSLGERATINCKSSQSVLYSSNNKNYLVWYQQKPGQPPKLLIYWASIR
MCP1-1.10_LC     DIVMTQSPASLAESLGERATINCKSSQSVLYSSNNKNYLVWYQQKLGQPPKLLIYWASTR
MCP1-1.11_LC     DIVMTQSPDSLAVSLGERATITCKSSQTVLYSSNNKNYLVWYQQKSGQPPKLLIHWASIR
MCP1-1.12_LC     DIVMTQSPDSLAVSLGERATINCKSSQSVLYSSNNKNYLVWYQQKPGQPPKLLIYWASIR
MCP1-1.13_LC     DIVMTQSPDSLAVCLGERATINCKSSQSVLYSPNNKNFLVWYQQRPGQPPKLLIYWASTR
MCP1-1.14.1.1_LC DIVMTQSPDSLAVSLGERATINCKSSQSVLYSSNNKNYIVWYQQKPGQPPKLLIYWTSTR
MCP1-1.18_LC     DIVMTQSPDSLAVSLGERATINCKSSQSVLYSSNNKNYLVWYQQKPGQPPKLLIYWASIR
MCP1-1.3_LC      DIVMTQSPDSLAVSLGERATINCKSSQSVLYSSNNKNYLAWYXQKPGQPPKLLIYWTYIR
MCP1-1.5.1_LC    DIVMTQSPDSLAASLGERATINCKSSQSVLYRSNNKNYLVWYQQKPGQPPKLLIYWASIR
MCP1-1.7_LC      DIVMTQSPDSLAVSLGERATINCKSSQSVLYSSNNKNYLVWYQQRPGQPPKLLIYWASTR
MCP1-1.8_LC      DIVMTQSPGSLAVSLGERATINCKSSQSILFRSNNKNYLTWYQQKPGQPPKLLIYWASIR
MCP1-1.9_LC      DIVMTQSPDFLAVSLGERPTINCKSSQSVFYSSNNKNYLVWYQQKPGQPPKLLLYWASTR
MCP1-2.3_LC      DIVMTQSPDSLAVSLGERATINCKSSQSVLYGSNNKSYLAWYQQKPGQPPKLLIYWASTR
MCP1-3.14.1.1_LC DIVMTQSPDSLAVSLGERAAINCKSSQTVLYSSNNKNYLVWYQQKPGQPPKLLIYWASTR
MCP1-3.15_LC     DIVMTQSPDSLAVSLGERATINCKSSQSVLYSSNNNNYLVWYQQKPGQPPKLLIYWASTR
MCP1-3.16_LC     DIVMTQSPDSLAVSLGERATINCKSSQSVLFSSNNKSYLTWYQQKPGQPPKLLIFWASIR
MCP1-3.4_LC      DIVMTQSPDSLAVSLDERATINCKSSQSVLYSPNQKNYLVWYQQKPGQPPKLLLYWASIR
MCP1-3.5_LC      DIVMTQSPDSLAVSLGERATINCKSSQSVLYSSDNKSYLVWYQQKPGQPPKVLIYWASIR
MCP1-3.6_LC      DIVMTQSPDSLAVSLGERATINCKSSLSVLYSSNNKNYLWYLQKPGQPPKLLIYWASTR
MCP1-3.7_LC      DIVMTQSPDSLAVSLGERATINCKSSQSVLYSSNNKNYLVWYQQKPGQPPKTLIYWASTR
MCP1-3.8_LC      DIVMTQSPDSLAVSLGERATINCKSSQSILYSSNNKNYLVWYQQKPGQPPKLLIYWASTR
MCP1-4.5_LC     ·DIVMTQSPDSLAVSLGERATINCKSSQSVLYRSNNKSYLVWYQQKLGQSPKLLIYWASTR
MCP1-4.6.3_LC    DIVMTQSPDSLAVSLGERATINCKSSQSVLYSSNNKNYLVWYQQKPGQPPKLLIYWASTR
MCP1-4.7_LC      DIVMTQSPDSLAVSLGERATINCKSSQSVLYSSNNKNYLAWYQQKPGQPPKLLIYWTSTR
MCP1-4.8.1_LC    DIVMTQSPDSLAVSLGERATINCKSSQSLLYSSKNKNYLVWYQQKPGQPPKLLINWASTR
MCP1-5.3_LC      DIVMTQSPDSLAVSLGERATINCKSSQSVLYSSNSKNYLAWFQQKPGQPPKLLIYWASTR
```

Figure 8A (cont.)

```
                          CDR2                              CDR3
                          ━━━                               ━━━━━━━
VK-B3             ESGVPDRFSGSGSGTDFTLTISSLQAEDVAVYYCQQYYSTP------------
MCP1-1.1.1_LC     ESGVPDRFSSSGSETDFTLTISSLQAEDVAVYYCQQYFSSPWTFGQGTKVEIK
MCP1-1.10_LC      ESGVPDRFSGSGSGTDFTLTISSLQAEDVAVYYCQQYYRSPWTFGQGTKVEIK
MCP1-1.11_LC      ESGVPDRFSGSGSGTDFTLTISSLQAEDVAVYYCQQYYSSPWTFGQGTKVEIK
MCP1-1.12_LC      ESGVPDRFSGSGSGTDFTLTINSLQAEDVAVYYCQQYFYSPWTFGQGTKVEIK
MCP1-1.13_LC      ESGVPDRFSGSGSGTDFTLTISSLQAEDVAVYYCQQYYSSPWTFGQGTKVEIK
MCP1-1.14.1.1_LC  ESGVPDRFSGSGSGTDFTLTISSLQAEDVAVYYCQQYFSSPWTFGQGTKVDIK
MCP1-1.18_LC      ESGVPDRFSGSGSGTDFTLTISSLQAEDVAVYYCQQYYSTPLTFGGGTKVEIK
MCP1-1.3_LC       ESGVPDRFSGSGSGTDFTLTISSLQAEDVAVYYCQEHYSIPWTFGQGTKVEIK
MCP1-1.5.1_LC     ESGVPDRFSGSGSGTDFTLTISSLQAEDVAVYFCQQYYSSPWTFGQGTKVEIK
MCP1-1.7_LC       ESGVPDRFSGSGSGTDFTLTISSLQAEDVAVYYCQQYFYSPWTFGQGTKVEIK
MCP1-1.8_LC       ESGVPDRFSGSGSGSNFTLTITSLQAEDVAIYYCQQYYSSPWTFGQGTKVEIK
MCP1-1.9_LC       ESGVPDRFSGSGSGTDFTLTISSLQAEDVAVYYCQQYYSSPWTFGQGTKVEIK
MCP1-2.3_LC       ESGVPDRFSGSGSGTDFTLTISSLQAADVAVYYCQQHYSTPCSFGQGTKLEIK
MCP1-3.14.1.1_LC  ESGVPDRFSGSGSGTDFTLTISSLQAEDVAVYYCQQYYKSPWTFGQGTKVEIK
MCP1-3.15_LC      EFGVPDRFSGSGSGTDFTLTISSLQAEDVAVYYCQQYYFSPWTFGQGTKVEIK
MCP1-3.16_LC      ESGVPDRISGSGSGTDLTLTISSLQAEDAAVYYCQQYYSSPWTFGQGTKVEIK
MCP1-3.4_LC       ESGVPDRFSGSGSGTDFTLTISSLQAEDVAVYYCQQSYFTPWTFGQGTKVEIK
MCP1-3.5_LC       ESGVPDRFSGSGSGTDFTLTISSLQAEDVAVYYCQQYYTSPWTFGQGTKVEIK
MCP1-3.6_LC       ESGVPDRFSGSGSGTDFTLTISSLQAEDVAVYYCQQYYSSPWTFGQGTKVEIK
MCP1-3.7_LC       ESGVPDRFSGSGSGTDFTLTISSLQAEDVGVYYCQQYYTSPWTFGQGTKVEIK
MCP1-3.8_LC       ESGVPDRFSGSGSGTDFTLTISSLQAEDVAVYYCQQYYSSPPTFGQGTKVEIK
MCP1-4.5_LC       ESGVPDRFSGSGSGTDFTLTISSLQAEDVAVYYCQQYYSTPWTFGQGTKVEIK
MCP1-4.6.3_LC     ESGVPDRFSGSGSGTDFTLTISSLQAEDVAVYYCQQYYSPTWTFGQGTKVEIK
MCP1-4.7_LC       ESGVPDRFSGSGSVTDFTLTISSLQAEDVAVYYCQQYYSSPWTFGQGTKVEIK
MCP1-4.8.1_LC     ESGVPDRFSGSGSGTDFTLTISSLQAEDVAVYYCQQYYSSPWTFGQGTKVEIK
MCP1-5.3_LC       ESGVPDRFSGSGSGTDFTLTISRLQAEDVAVYSCQQYFITPWTFGQGTKVELK
```

Dendrogram:

Figure 9A

Alignment of sequences using VK-O8

```
                                            CDR1                      CDR2
                                            ────                      ────
VK-O8         DIQMTQSPSSLSASVGDRVTITCQASQDISNYLNWYQQKPGKAPKLLIYDASNLETGVPS
MCP1-2.4_LC   DIQMTQSPSSLSASVGDRVTITCQASQDITTYLNWYQQKPGKAPKLLIYDASNLETGVPS
MCP1-3.11_LC  DIQMTQSPSSLSASVGDRVTITCQASQDISNYLNWYQQKPGKAPKLLIYDASNLETGVPS
              ****************************:.******************************

CDR3
                                    ────
VK-O8         RFSGSGSGTDFTFTISSLQPEDIATYYCQQYDNLP------------
MCP1-2.4_LC   RFSGSGSGTDFTFTISSLQPEDIATYYCQQYDNLPITFGQGTRLEIK
MCP1-3.11_LC  RFSGSGSGTDFTFTINSLQPEDIATYYCQEYNNLPYSFGQGTKLEIK
              ***************.*************:*:***
```

Figure 9B

Dendrogram:

Figure 10A

Alignment of sequences using VH6-1

```
                                            CDR1                    CDR2
VH6-1             QVQLQQSGPGLVKPSQTLSLTCAISGDSVSSNSAAWNWIRQSPSRGLEWLGRTYYRSKWY
MCP1-1.4.1.1_HC   QVQAEQSGPGLVKPSQTLSLTCAISGDSVSSNSAAWNWIRQSPSRGLEWLGRTYYRSKWY
MCP1-1.14.1.1_HC  QVQAEQSGPGLVKPSQTLSLTCAISGDSVSSYSAAWNWIRQSPSRGLEWLGRTYYRSKWY
MCP1-3.14.1.1_HC  QVQAEQSGPGLVKPSQTLSLTCAISGDSVSSNSAAWNWIRQSPSRGLEWLGRTYYRSKWY

CDR2                              CDR3
VH6-1             NDYAVSVKSRITINPDTSKNQFSLQLNSVTPEDTAVYYCAR-------------------
MCP1-1.4.1.1_HC   SDHAVSVRSRITIYPDTSKNQFSLQLNSVTPEDTAVYYCARDRISGTYVGMDVWGQGTTV
MCP1-1.14.1.1_HC  SDHAVSVRSRITIYPDTSKNQFSLQLNSVTPEDTAVYYCARDRISGTYVGMDVWGQGTTV
MCP1-3.14.1.1_HC  SDHAVSVRSRITIYPDTSKNQFSLQLNSVTPEDTAVYYCARDRISGTYVGMDVWGQGTTV

VH6-1             ---
MCP1-1.4.1.1_HC   VSS
MCP1-1.14.1.1_HC  VSS
MCP1-3.14.1.1_HC  VSS
```

Figure 10B

Dendrogram:

ANTIBODIES DIRECTED TO MONOCYTE CHEMO-ATTRACTANT PROTEIN-1 (MCP-1) AND USES THEREOF

PRIORITY CLAIM

This application is a divisional application of U.S. patent application Ser. No. 10/644,277, filed on Aug. 19, 2003, now U.S. Pat. No. 7,202,343 which claims priority under 35 U.S.C. §119(e) to U.S. Provisional Application No. 60/404,802, filed Aug. 19, 2002, which is hereby expressly incorporated by reference.

BACKGROUND OF THE INVENTION

1. Field of the Invention

Embodiments of the invention described herein relate to antibodies directed to the antigen monocyte chemo-attractant protein-1 (MCP-1) and uses of such antibodies. In particular, in accordance with embodiments of the invention, there are provided fully human monoclonal antibodies directed to the antigen MCP-1. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDRs), specifically from FR1 through FR4 or CDR1 through CDR3, are provided. The antibodies of the invention find use as diagnostics and as treatments for diseases associated with the overproduction of MCP-1. Hybridomas or other cell lines expressing such immunoglobulin molecules and monoclonal antibodies are also provided.

2. Description of the Related Art

An increased production of angiogenic factors and decreased production of angiogenesis inhibitors by cancer cells, vascular endothelial cells and other stromal cell types are believed to induce tumor angiogenesis. Stroma, comprised of interstitial connective tissues, basal lamina, blood cells, blood vessels and fibroblastic cells, surround almost all solid tumor cells. Interactions between the stroma and cancer cells play a critical role in the neovascularization of tumors. Further, macrophage, which are also stromal components, are important in tumor angiogenesis. (M. Ono et al., *Cancer Chemother. Pharmacol.* (1999) 43(Suppl.): S69-S71.)

Macrophages are the major terminally differentiated cell type of the mononuclear phagocyte system, and are also one of the key angiogenic effector cells, producing a number of growth stimulators and inhibitors. A number of angiogenic cytokines are known to be produced by macrophages, including monocyte chemo-attractant protein 1 (MCP-1).

MCP-1 is known to be chemotactic for T lymphocytes, basophils and NK cells. MCP-1 is one of the most potent macrophage recruiting molecules. Once recruited to sites of inflammation or tumors, macrophages can generate a number of angiogenic cytokines, thereby stimulating pathologic angiogenesis. A number of studies have shown a relationship between angiogenesis, macrophage recruitment, and prognosis in patients with various kinds of tumors (G. Fantanini et al., *Int. J. Cancer* (1996) 67:615; N. Weidner et al., *J. Natl. Cancer Inst.* (1992) 84:1875). Leek et al. have further demonstrated that focally increased macrophage numbers are closely related to vascularization and prognosis in breast cancer patients (*Cancer Res.* (1996) 56:4625). R. Huang et al. (*Cancer Res.* (2002) 62:2806-2812) have shown that Connexin 43 suppresses human glioblastoma cell growth by down regulation of MCP-1, as discovered by using protein array technology.

Goede et al. (*Int. J. Cancer* (1999) 82: 765-770) first demonstrated that MCP-1 had an angiogenic potency which was equivalent to that of VEGF when tested in a rabbit corneal model. In their model, the angiogenic activity induced by MCP-1 was associated with an intense recruitment of macrophages into the rabbit cornea. Salcedo et al. have reported that MCP-1 induced chemotaxis of human endothelial cells at nanomolar concentrations. This chemotactic response was inhibited by a polyclonal antibody to human MCP-1 (R. Salcedo et al., *Blood* (2000) 96(1):34-40).

MCP-1 is the predominant chemokine expressed in ovarian cancer (Negus, R. P. M. et al., *J. Clin. Investig.* (1995) 95: 2391-96; Sica, A. et al., *J. Immunology* (2000) 164(2):733-8). MCP-1 is also elevated in a number of other human cancers including bladder, breast, lung, and glioblastomas.

In addition, the importance of MCP-1 in inflammation has been shown in a number of studies. For example, H. J. Anders et al., have demonstrated chemokine and chemokine receptor expression during initiation and resolution of immune complex glomerulonephritis (*J. Am. Soc. Nephrol.* (2001) 12: 919-2001). Segerer et al. (*J. Am. Soc. Nephrol.* (2000) 11:2231-2242) also have studied the expression of MCP-1 and its receptor chemokine receptor 2 in human crescentic glomerulonephritis. J. A. Belperio et al. have shown a critical role for the chemokine MCP-1/CCR2 in the pathogenesis of bronchiolitis obliterans syndrome (*J. Clin. Investig.* (2001) 108: 547-556). N. G. Frangogiannis et al. have delineated the role of MCP-1 in the inflammatory response in myocardial infarction (*Cardiovacular Res.* (2002) 53: 31-47). Gerard and Rollins (*Nature Immunol.* (2001) 2:108-115) and Reape and Groot (*Atherosclerosis* (1999) 147: 213-225) have discussed the role of MCP-1 in atherosclerosis and other diseases. Also, Schmidt and Stern (*Arterioscler. Thromb. Vasc. Biol.* (2001) 21:297-299) describe MCP-1 interactions in restenosis.

Human MCP-1, a 76-amino-acid CC chemokine with an N-terminal pyroglutamic acid, was originally purified from several sources including phytohemagglutinin-stimulated human lymphocytes (Yoshimura, T. et al., *J. Immunol.* (1989) 142:1956-62), a human glioma cell line (Yoshimura, T., et al., *J. Exp. Med.* (1989) 169:1449-59), and the human myelomonocytic cell line THP-1 (Matsushima, K., et al., (1989) *J. Exp. Med.* (1989) 169: 1485-90). MCP-1 was first described as lymphocyte-derived chemotactic factor (LDCF). Other names for the protein are tumor-cell-derived chemotactic factor (TDCF), glioma-derived monocyte chemotactic factor (TDCF), glioma-derived monocyte chemotactic factor (GDCF), smooth muscle cell-derived chemotactic factor (SMC-CF), monocyte chemotactic activating factor (MCAF) and CCL2. Molecular cloning of the cDNA encoding MCP-1 (Furutani, Y., et al., (1989) *Biochem. Biophys. Res. Comm.* (1989) 169:249-55; B. J. Rollins, et al., *Mol. Cell. Biol.* (1989) 9:4687-95; Chang, H. C., et al., *Int. Immunol.* (1989) 1:388-97) revealed an open reading frame of 99 amino acids, including a signal peptide of 23 amino acids. The mouse homologue gene of MCP-1 was named JE (B. J. Rollins et al., 1989).

WO 200189565, published Nov. 29, 2001, discloses polyclonal antibodies to human MCP-1 and describes the inhibition of tumor growth in a nude mouse model by the use of such polyclonal antibodies.

Embodiments of the invention described herein relate to fully human monoclonal antibodies to human MCP-1 that block MCP-1-induced chemotaxis of THP-1 cells, a cell line derived from a patient with acute monocytic leukemia. These cells are used as a surrogate for assessing the migration of normal human mononuclear cells in circulation. Mononuclear cell infiltration stimulated by MCP-1 plays a pathologic role in a number of inflammatory conditions including rheumatoid arthritis, glomerulonephritis, atherosclerosis, transplant rejection, psoriasis, restenosis, and autoimmune diseases such as multiple sclerosis. An antibody that blocks MCP-1 activity and prevents monocyte infiltration will find use as a treatment for these and other inflammatory diseases.

SUMMARY OF THE INVENTION

Embodiments of the invention described herein related to monoclonal antibodies that were found to bind MCP-1 and affect MCP-1 function. Other embodiments relate to human anti-MCP-1 antibodies and anti-MCP-1 antibody preparations with desirable properties from a therapeutic perspective, including strong binding affinity for MCP-1, the ability to neutralize MCP-1 in vitro, and the ability to inhibit neovascularization of solid tumors.

One embodiment of the invention is an isolated human monoclonal antibody that binds to MCP-1 and includes a heavy chain polypeptide having the sequence of SEQ ID NO: 18. Optionally, the antibody may also include a light chain polypeptide having the sequence of SEQ ID NO: 20. In another aspect of the invention, the isolated antibody may be immobilized on an insoluble matrix, wherein the antibody includes a heavy chain polypeptide having the sequence of SEQ ID NO.: 18 and a light chain polypeptide having the sequence of SEQ ID NO: 20.

In one aspect of the invention, a method for assaying the level of monocyte chemo-attractant protein-1 (MCP-1) in a patient sample is provided. The method may include contacting an anti-MCP-1 antibody with the patient sample and detecting the level of MCP-1 in the patient sample. Advantageously, the patient sample is blood.

One embodiment of the invention is a fully human monoclonal antibody that binds to MCP-1 and has a heavy chain amino acid sequence selected from the group consisting of SEQ ID NOS: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142 and 146. In one embodiment, the antibody further comprises a light chain amino acid sequence selected from the group consisting of SEQ ID NOS: 4, 8, 12, 16, 20, 24, 28, 32, 36, 40, 44, 48, 52, 56, 60, 64, 68, 72, 76, 80, 84, 88, 92, 96, 100, 104, 108, 112, 116, 120, 124, 128, 132, 136, 140, 144 and 148.

Accordingly, one embodiment of the invention described herein provides isolated antibodies, or fragments of those antibodies, that bind to MCP-1. As known in the art, the antibodies can advantageously be, for example, monoclonal, chimeric and/or human antibodies. Embodiments of the invention described herein also provide cells for producing these antibodies.

Another embodiment of the invention is a fully human antibody that binds to MCP-1 that comprises a heavy chain amino acid sequence having the CDRs comprising the sequences shown in FIGS. 7 and 10. It is noted that CDR determinations can be readily accomplished by those of ordinary skill in the art. In general, CDRs are presented in the invention described herein as defined by Kabat et al., in *Sequences of Proteins of Immunological Interest* vols. 1-3 (Fifth Edition, NIH Publication 91-3242, Bethesda Md. 1991).

Yet another embodiment of the invention is a fully human antibody that binds to MCP-1 and comprises a light chain amino acid sequence having the CDRs comprising the sequences shown in FIGS. 8 and 9.

A further embodiment of the invention is a fully human antibody that binds to MCP-1 and comprises a heavy chain amino acid sequence having the CDRs comprising the sequences shown in FIGS. 7 and 10 and a light chain amino acid sequence having the CDRs comprising the sequences shown in FIGS. 8 and 9.

Another embodiment of the invention is a fully human antibody that binds to other MCP-1 family members including, but not limited to, MCP-2, MCP-3 and MCP-4. A further embodiment of the invention is an antibody that cross-competes for binding to MCP-1 with the fully human antibodies of the invention.

In still another aspect of the invention, a composition having an antibody which includes a heavy chain polypeptide having the sequence of SEQ ID NO.: 18 and a light chain polypeptide having the sequence of SEQ ID NO: 20 and a pharmaceutically acceptable carrier.

In another aspect of the invention, a method of treating a neoplastic disease is disclosed. The method may include selecting an animal in need of treatment for a neoplastic disease and administering to the animal a therapeutically effective dose of a fully human monoclonal antibody having a heavy chain polypeptide that includes the sequence of SEQ ID NO.: 18. Advantageously, the neoplastic disease can be breast cancer, ovarian cancer, bladder cancer, lung cancer, glioblastoma, stomach cancer, endometrial cancer, kidney cancer, colon cancer, pancreatic cancer, or prostate cancer.

In yet another aspect of the invention, a method of treating inflammatory conditions is provided. The method may include selecting an animal in need of treatment for an inflammatory condition and administering to that animal a therapeutically effective dose of the fully human monoclonal antibody having a heavy chain polypeptide which includes the sequence of SEQ ID NO.: 18. The inflammatory condition may be rheumatoid arthritis, glomerulonephritis, atherosclerosis, psoriasis, restenosis, autoimmune disease, or multiple sclerosis.

In another embodiment, an isolated human monoclonal antibody that cross-competes for binding to MCP-1 is provided, wherein the antibody comprises a heavy chain polypeptide having the sequence of SEQ ID NO.: 18. Optionally, the antibody may further include a light chain polypeptide having the sequence of SEQ ID NO.: 20.

In yet another embodiment, a method of manufacturing an antibody that binds to MCP-1 and includes a heavy chain polypeptide having the sequence of SEQ ID NO: 18 is disclosed. The method includes immunizing a mammal with a synthetic peptide of MCP-1, recovering lymphatic cell that expresses the antibody from the immunized mammal, and fusing the lymphatic cell with a myeloid-type cell to prepare a hybridoma cell that produces the fully human antibody.

In another embodiment, the isolated fully human monoclonal antibody that binds to MCP-1 and includes a heavy chain polypeptide having the sequence of SEQ ID NO: 18 is conjugated to a therapeutic agent. The therapeutic agent may be a toxin such as an immunotoxin. Alternatively, the therapeutic agent may be a chemotherapeutic agent such as taxol, doxorubicin, cis-platinum, or 5-fluorouracil. Optionally, the therapeutic agent is a radioisotope such as $^{3}H$, $^{14}C$, $^{15}N$, $^{35}S$, $^{90}Y$, $^{99}Tc$, $^{111}In$, $^{125}I$, or $^{131}I$.

In yet another embodiment, an isolated human monoclonal antigen binding fragment that binds to MCP-1 and comprises a heavy chain polypeptide having the sequence of SEQ ID NO: 18 is provided. The antigen binding fragment may include a light chain polypeptide having the sequence of SEQ ID NO: 20. Optionally, the antigen binding fragment is Fab, Fab', F(ab')$_2$, or F$_v$. The antigen binding fragment may be conjugated to a therapeutic agent.

In still another embodiment, an isolated fully human monoclonal antibody or binding fragment thereof that binds to an epitope comprising the amino acid sequence SVQRL (SEQ ID NO:157) is provided.

Another embodiment of the invention is a fully human antibody that binds to other MCP-1 family members including, but not limited to, MCP-2, MCP-3 and MCP-4. A further embodiment of the invention is an antibody that cross-competes for binding to MCP-1 with the fully human antibodies of the invention.

It will be appreciated that embodiments of the invention are not limited to any particular form of an antibody or method of generation or production. For example, the anti-MCP-1 antibody may be a full-length antibody (e.g., having an intact human Fc region) or an antibody fragment (e.g., a Fab, Fab' or F(ab')$_2$). In addition, the antibody may be manufactured from a hybridoma that secretes the antibody, or from a recombinantly produced cell that has been transformed or transfected with a gene or genes encoding the antibody.

Other embodiments of the invention include isolated nucleic acid molecules encoding any of the antibodies described herein, vectors having an isolated nucleic acid molecules encoding any of such the anti-MCP-1 antibodies, a host cell transformed with any of such nucleic acid molecules. In addition, one embodiment of the invention is a method of producing an anti-MCP-1 antibody by culturing host cells under conditions wherein a nucleic acid molecule is expressed to produce the antibody followed by recovering the antibody.

A further embodiment of the invention includes a method of producing high affinity antibodies to MCP-1 by immunizing a mammal with human MCP-1 or a fragment thereof and one or more orthologous sequences or fragments thereof.

Embodiments of the invention described herein are based upon the generation and identification of isolated antibodies that bind specifically to MCP-1. MCP-1 is expressed at elevated levels in neoplastic diseases, such as tumors, and other inflammatory diseases. Inhibition of the biological activity of MCP-1 can prevent further infiltration of mononuclear cells into tissues.

Another embodiment of the invention includes a method of diagnosing diseases or conditions in which an antibody prepared according to the invention described herein is utilized to detect the level of MCP-1 in a patient sample. In one embodiment, the patient sample is blood or blood serum. In further embodiments, methods for the identification of risk factors, diagnosis of disease, and staging of disease is presented which involves the identification of the overexpression of MCP-1 using anti-MCP-1 antibodies.

In another embodiment, the invention includes a method for diagnosing a condition associated with the expression of MCP-1 in a cell, comprising contacting the cell with an anti-MCP-1 antibody, and detecting the presence of MCP-1. Preferred conditions include, but are not limited to, neoplastic diseases including, without limitation, tumors, cancers, such as breast, ovarian, stomach, endometrial, salivary gland, lung, kidney, colon, colorectal, thyroid, pancreatic, prostate and bladder cancer, as well as other inflammatory conditions, including, but not limited to, rheumatoid arthritis, glomerulonephritis, atherosclerosis, psoriasis, organ transplants, restenosis and autoimmune diseases.

In another embodiment, the invention includes an assay kit for the detection of MCP-1 and MCP-1 family members in mammalian tissues or cells to screen for neoplastic diseases or inflammatory conditions, comprising an antibody that binds to MCP-1 and a means for indicating the reaction of the antibody with the antigen, if present. Preferably the antibody is a monoclonal antibody. In one embodiment, the antibody that binds MCP-1 is labeled. In another embodiment the antibody is an unlabeled first antibody and the means for indicating the reaction comprises a labeled second antibody that is an anti-immunoglobulin. Preferably the antibody is labeled with a marker selected from the group consisting of a fluorochrome, an enzyme, a Radionuclide and a radiopaque material.

Other embodiments of the invention include pharmaceutical compositions comprising an effective amount of the antibody of the invention in admixture with a pharmaceutically acceptable carrier or diluent. In yet other embodiments, the anti-MCP-1 antibody or fragment thereof is conjugated to a therapeutic agent. The therapeutic agent can be a toxin or a radioisotope. Preferably, such antibodies can be used for the treatment of diseases, such as, for example, tumors, including, without limitation, cancers, such as breast, ovarian, stomach, endometrial, salivary gland, lung, kidney, colon, colorectal, thyroid, pancreatic, prostate and bladder cancer, as well as other inflammatory conditions, including, but not limited to, rheumatoid arthritis, glomerulonephritis, atherosclerosis, psoriasis, organ transplants, restenosis and autoimmune diseases.

Yet another embodiment of the invention provides a method for treating diseases or conditions associated with the expression of MCP-1 in a patient, comprising administering to the patient an effective amount of an anti-MCP-1 antibody. The method can be performed in vivo. The patient is a mammalian patient, preferably a human patient. In a preferred embodiment, the method concerns the treatment of tumors, including, without limitation, cancers, such as breast, ovarian, stomach, endometrial, salivary gland, lung, kidney, colon, colorectal, thyroid, pancreatic, prostate and bladder cancer. In another embodiment, the method concerns the treatment of inflammatory conditions, including, but not limited to, rheumatoid arthritis, glomerulonephritis, atherosclerosis, psoriasis, organ transplants, restenosis and autoimmune diseases. Additional embodiments include methods for the treatment of diseases and conditions associated with the expression of MCP-1, which can include identifying a mammal in need of treatment for overexpression of MCP-1 and administering to the mammal, a therapeutically effective dose of anti-MCP-1 antibodies.

In another embodiment, the invention provides an article of manufacture comprising a container, comprising a composition containing an anti-MCP-1 antibody, and a package insert or label indicating that the composition can be used to treat neoplastic and inflammatory diseases characterized by the overexpression of MCP-1. Preferably a mammal, and more preferably, a human receives the anti-MCP-1 antibody. In a preferred embodiment, tumors, including, without limitation, cancers, such as breast, ovarian, stomach, endometrial, salivary gland, lung, glioblastomas, kidney, colon, colorectal, thyroid, pancreatic, prostate and bladder cancer, as well as other inflammatory conditions, including, but not limited to, rheumatoid arthritis, glomerulonephritis, atherosclerosis, psoriasis, organ transplants, restenosis and autoimmune diseases such as multiple sclerosis are treated.

In some embodiments, the anti-MCP-1 antibody is administered, followed by a clearing agent to remove circulating antibody from the blood.

In some embodiments, anti-MCP-1 antibodies can be modified to enhance their capability of fixing complement and participating in complement-dependent cytotoxicity (CDC). In one embodiment, the anti-MCP-1 antibody can be modified, such as by an amino acid substitution, to alter antibody clearance. For example, certain amino acid substitutions may accelerate clearance of the antibody from the body. Alternatively, the amino acid substitutions may slow the clearance of antibody from the body. In other embodiments, the anti-MCP-1 antibody can be altered such that it is eliminated less rapidly from the body.

BRIEF DESCRIPTION OF THE DRAWINGS

FIG. 9A shows a Clustal W comparison of anti-MCP-1 sequences using VK-08, indicating the CDR1, CDR2, and CDR3 regions, and the associated dendrogram (FIG. 9B).

FIG. 10A shows a Clustal W comparison of anti-MCP-1 sequences using VH6-1, indicating the CDR1, CDR2, and CDR3 regions, and the associated dendrogram (FIG. 10B).

DETAILED DESCRIPTION OF THE PREFERRED EMBODIMENT

Figure 1:
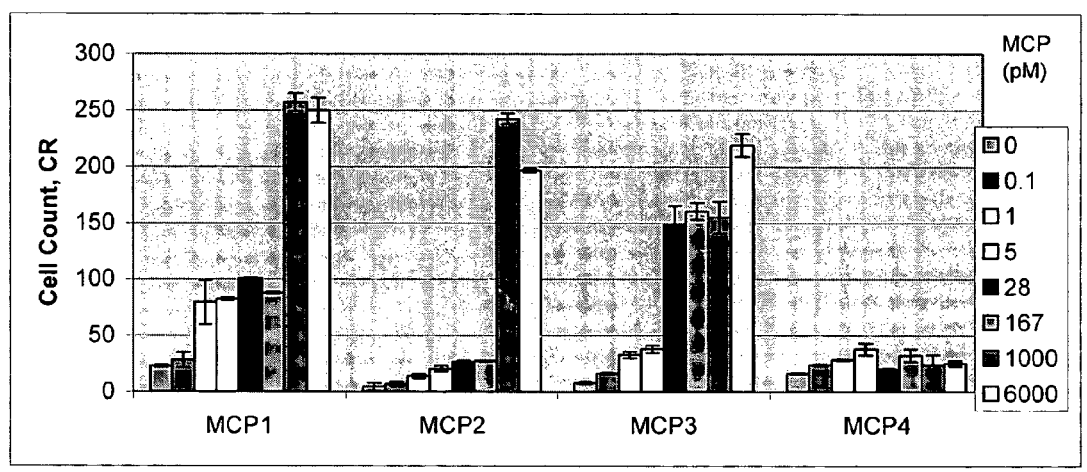
FIG. 1 shows results of THP-1 monocyte migration studies in response to MCP-1, MCP-2, MCP-3 and MCP-4.

Embodiments of the invention described herein relate to monoclonal antibodies that bind to MCP-1. In some embodiments, the antibodies bind to MCP-1 and affect MCP-1 function. Other embodiments provide fully human anti-MCP-1 antibodies and anti-MCP-1 antibody preparations with desirable properties from a therapeutic perspective, including strong binding affinity for MCP-1, the ability to neutralize MCP-1 in vitro, and the ability to inhibit the growth and neovascularization of solid tumors in vivo.

Accordingly, embodiments of the invention provide isolated antibodies, or fragments of those antibodies, that bind to MCP-1. As known in the art, the antibodies can advantageously be, e.g., monoclonal, chimeric and/or human antibodies. Embodiments of the invention also provide cells for producing these antibodies.

In some embodiments, the antibodies described herein possess therapeutic utilities. An anti-MCP-1 antibody can potentially block or limit the extent of tumor neovascularization and tumor growth. Many cancer cells including those from glioblastomas and renal cancers express the receptor for MCP-1, CCR2. The co-expression of ligand and receptor in the same tumor cell suggests that MCP-1 may regulate an autocrine growth loop in cancer cells that express both components. Huang et al. (*Cancer Res.* (2002) 62:2806-2812) have recently reported that MCP-1 can directly influence the growth and survival of tumor cells that express the CCR2 receptor for MCP-1. Thus, in addition to its effects on angiogenesis, MCP-1 may also directly regulate tumor cell growth, migration and invasion.

In addition, embodiments of the invention provide for using these antibodies as a diagnostic or treatment for disease. For example, embodiments of the invention provide methods and antibodies for inhibition expression of MCP-1 associated with tumors and inflammatory conditions. Preferably, the antibodies are used to treat cancers, such as breast, ovarian, stomach, endometrial, salivary gland, lung, kidney, colon, colorectal, thyroid, pancreatic, prostate and bladder cancer, as well as other inflammatory conditions, including, but not limited to, rheumatoid arthritis, glomerulonephritis, atherosclerosis, psoriasis, organ transplants, restenosis and autoimmune diseases. In association with such treatment, articles of manufacture comprising antibodies of the invention described herein are provided. Additionally, an assay kit comprising antibodies in accordance with the invention described herein is provided to screen for tumors and inflammatory conditions.

Additionally, the nucleic acids described herein, and fragments and variants thereof, may be used, by way of nonlimiting example, (a) to direct the biosynthesis of the corresponding encoded proteins, polypeptides, fragments and variants as recombinant or heterologous gene products, (b) as probes for detection and quantification of the nucleic acids disclosed herein, (c) as sequence templates for preparing antisense molecules, and the like. Such uses are described more fully in the following disclosure.

Furthermore, the proteins and polypeptides described herein, and fragments and variants thereof, may be used, in ways that include (a) serving as an immunogen to stimulate the production of an anti-MCP-1 antibody, (b) a capture antigen in an immunogenic assay for such an antibody, (c) as a target for screening for substances that bind to a MCP-1 polypeptide described herein, and (d) a target for a MCP-1 specific antibody such that treatment with the antibody affects the molecular and/or cellular function mediated by the target.

In view of its strong effects in modulating cell growth, an increase of MCP-1 polypeptide expression or activity can be used to promote cell survival. Conversely, a decrease in MCP-1 polypeptide expression can be used to induce cell death.

Further embodiments, features, and the like regarding the antibodies of the invention are provided in additional detail below.

Sequence Listing

The heavy chain and light chain variable region nucleotide and amino acid sequences of representative human anti-MCP-1 antibodies are provided in the sequence listing, the contents of which are summarized in Table 1 below.

TABLE 1

| mAb ID No.: | Sequence | SEQ ID NO: |
|---|---|---|
| 1.1.1 | Nucleotide sequence encoding the variable region of the heavy chain | 1 |
| | Amino acid sequence encoding the variable region of the heavy chain | 2 |
| | Nucleotide sequence encoding the variable region of the light chain | 3 |
| | Amino acid sequence encoding the variable region of the light chain | 4 |

TABLE 1-continued

| mAb ID No.: | Sequence | SEQ ID NO: |
|---|---|---|
| 1.10.1 | Nucleotide sequence encoding the variable region of the heavy chain | 5 |
| | Amino acid sequence encoding the variable region of the heavy chain | 6 |
| | Nucleotide sequence encoding the variable region of the light chain | 7 |
| | Amino acid sequence encoding the variable region of the light chain | 8 |
| 1.12.1 | Nucleotide sequence encoding the variable region of the heavy chain | 9 |
| | Amino acid sequence encoding the variable region of the heavy chain | 10 |
| | Nucleotide sequence encoding the variable region of the light chain | 11 |
| | Amino acid sequence encoding the variable region of the light chain | 12 |
| 1.13.1 | Nucleotide sequence encoding the variable region of the heavy chain | 13 |
| | Amino acid sequence encoding the variable region of the heavy chain | 14 |
| | Nucleotide sequence encoding the variable region of the light chain | 15 |
| | Amino acid sequence encoding the variable region of the light chain | 16 |
| 1.18.1 | Nucleotide sequence encoding the variable region of the heavy chain | 17 |
| | Amino acid sequence encoding the variable region of the heavy chain | 18 |
| | Nucleotide sequence encoding the variable region of the light chain | 19 |
| | Amino acid sequence encoding the variable region of the light chain | 20 |
| 1.2.1 | Nucleotide sequence encoding the variable region of the heavy chain | 21 |
| | Amino acid sequence encoding the variable region of the heavy chain | 22 |
| | Nucleotide sequence encoding the variable region of the light chain | 23 |
| | Amino acid sequence encoding the variable region of the light chain | 24 |
| 1.3.1 | Nucleotide sequence encoding the variable region of the heavy chain | 25 |
| | Amino acid sequence encoding the variable region of the heavy chain | 26 |
| | Nucleotide sequence encoding the variable region of the light chain | 27 |
| | Amino acid sequence encoding the variable region of the light chain | 28 |
| 1.5.1 | Nucleotide sequence encoding the variable region of the heavy chain | 29 |
| | Amino acid sequence encoding the variable region of the heavy chain | 30 |
| | Nucleotide sequence encoding the variable region of the light chain | 31 |
| | Amino acid sequence encoding the variable region of the light chain | 32 |
| 1.6.1 | Nucleotide sequence encoding the variable region of the heavy chain | 33 |
| | Amino acid sequence encoding the variable region of the heavy chain | 34 |
| | Nucleotide sequence encoding the variable region of the light chain | 35 |
| | Amino acid sequence encoding the variable region of the light chain | 36 |
| 1.7.1 | Nucleotide sequence encoding the variable region of the heavy chain | 37 |
| | Amino acid sequence encoding the variable region of the heavy chain | 38 |
| | Nucleotide sequence encoding the variable region of the light chain | 39 |
| | Amino acid sequence encoding the variable region of the light chain | 40 |
| 1.8.1 | Nucleotide sequence encoding the variable region of the heavy chain | 41 |
| | Amino acid sequence encoding the variable region of the heavy chain | 42 |
| | Nucleotide sequence encoding the variable region of the light chain | 43 |
| | Amino acid sequence encoding the variable region of the light chain | 44 |
| 1.9.1 | Nucleotide sequence encoding the variable region of the heavy chain | 45 |
| | Amino acid sequence encoding the variable region of the heavy chain | 46 |
| | Nucleotide sequence encoding the variable region of the light chain | 47 |
| | Amino acid sequence encoding the variable region of the light chain | 48 |
| 2.3.1 | Nucleotide sequence encoding the variable region of the heavy chain | 49 |
| | Amino acid sequence encoding the variable region of the heavy chain | 50 |
| | Nucleotide sequence encoding the variable region of the light chain | 51 |
| | Amino acid sequence encoding the variable region of the light chain | 52 |
| 2.4.1 | Nucleotide sequence encoding the variable region of the heavy chain | 53 |
| | Amino acid sequence encoding the variable region of the heavy chain | 54 |
| | Nucleotide sequence encoding the variable region of the light chain | 55 |
| | Amino acid sequence encoding the variable region of the light chain | 56 |
| 3.10.1 | Nucleotide sequence encoding the variable region of the heavy chain | 57 |
| | Amino acid sequence encoding the variable region of the heavy chain | 58 |
| | Nucleotide sequence encoding the variable region of the light chain | 59 |
| | Amino acid sequence encoding the variable region of the light chain | 60 |
| 3.11.1 | Nucleotide sequence encoding the variable region of the heavy chain | 61 |
| | Amino acid sequence encoding the variable region of the heavy chain | 62 |
| | Nucleotide sequence encoding the variable region of the light chain | 63 |
| | Amino acid sequence encoding the variable region of the light chain | 64 |
| 3.15.1 | Nucleotide sequence encoding the variable region of the heavy chain | 65 |
| | Amino acid sequence encoding the variable region of the heavy chain | 66 |
| | Nucleotide sequence encoding the variable region of the light chain | 67 |
| | Amino acid sequence encoding the variable region of the light chain | 68 |
| 3.16.1 | Nucleotide sequence encoding the variable region of the heavy chain | 69 |
| | Amino acid sequence encoding the variable region of the heavy chain | 70 |
| | Nucleotide sequence encoding the variable region of the light chain | 71 |
| | Amino acid sequence encoding the variable region of the light chain | 72 |
| 3.2 | Nucleotide sequence encoding the variable region of the heavy chain | 73 |
| | Amino acid sequence encoding the variable region of the heavy chain | 74 |
| | Nucleotide sequence encoding the variable region of the light chain | 75 |
| | Amino acid sequence encoding the variable region of the light chain | 76 |
| 3.4.1 | Nucleotide sequence encoding the variable region of the heavy chain | 77 |
| | Amino acid sequence encoding the variable region of the heavy chain | 78 |
| | Nucleotide sequence encoding the variable region of the light chain | 79 |
| | Amino acid sequence encoding the variable region of the light chain | 80 |

TABLE 1-continued

| mAb ID No.: | Sequence | SEQ ID NO: |
|---|---|---|
| 3.5.1 | Nucleotide sequence encoding the variable region of the heavy chain | 81 |
| | Amino acid sequence encoding the variable region of the heavy chain | 82 |
| | Nucleotide sequence encoding the variable region of the light chain | 83 |
| | Amino acid sequence encoding the variable region of the light chain | 84 |
| 3.6.1 | Nucleotide sequence encoding the variable region of the heavy chain | 85 |
| | Amino acid sequence encoding the variable region of the heavy chain | 86 |
| | Nucleotide sequence encoding the variable region of the light chain | 87 |
| | Amino acid sequence encoding the variable region of the light chain | 88 |
| 3.7.1 | Nucleotide sequence encoding the variable region of the heavy chain | 89 |
| | Amino acid sequence encoding the variable region of the heavy chain | 90 |
| | Nucleotide sequence encoding the variable region of the light chain | 91 |
| | Amino acid sequence encoding the variable region of the light chain | 92 |
| 3.9 | Nucleotide sequence encoding the variable region of the heavy chain | 93 |
| | Amino acid sequence encoding the variable region of the heavy chain | 94 |
| | Nucleotide sequence encoding the variable region of the light chain | 95 |
| | Amino acid sequence encoding the variable region of the light chain | 96 |
| 4.4 | Nucleotide sequence encoding the variable region of the heavy chain | 97 |
| | Amino acid sequence encoding the variable region of the heavy chain | 98 |
| | Nucleotide sequence encoding the variable region of the light chain | 99 |
| | Amino acid sequence encoding the variable region of the light chain | 100 |
| 4.5.1 | Nucleotide sequence encoding the variable region of the heavy chain | 101 |
| | Amino acid sequence encoding the variable region of the heavy chain | 102 |
| | Nucleotide sequence encoding the variable region of the light chain | 103 |
| | Amino acid sequence encoding the variable region of the light chain | 104 |
| 4.6.1 | Nucleotide sequence encoding the variable region of the heavy chain | 105 |
| | Amino acid sequence encoding the variable region of the heavy chain | 106 |
| | Nucleotide sequence encoding the variable region of the light chain | 107 |
| | Amino acid sequence encoding the variable region of the light chain | 108 |
| 4.7.1 | Nucleotide sequence encoding the variable region of the heavy chain | 109 |
| | Amino acid sequence encoding the variable region of the heavy chain | 110 |
| | Nucleotide sequence encoding the variable region of the light chain | 111 |
| | Amino acid sequence encoding the variable region of the light chain | 112 |
| 5.3.1 | Nucleotide sequence encoding the variable region of the heavy chain | 113 |
| | Amino acid sequence encoding the variable region of the heavy chain | 114 |
| | Nucleotide sequence encoding the variable region of the light chain | 115 |
| | Amino acid sequence encoding the variable region of the light chain | 116 |
| 3.1 | Nucleotide sequence encoding the variable region of the heavy chain | 117 |
| | Amino acid sequence encoding the variable region of the heavy chain | 118 |
| | Nucleotide sequence encoding the variable region of the light chain | 119 |
| | Amino acid sequence encoding the variable region of the light chain | 120 |
| 1.11.1 | Nucleotide sequence encoding the variable region of the heavy chain | 121 |
| | Amino acid sequence encoding the variable region of the heavy chain | 122 |
| | Nucleotide sequence encoding the variable region of the light chain | 123 |
| | Amino acid sequence encoding the variable region of the light chain | 124 |
| 1.14.1 | Nucleotide sequence encoding the variable region of the heavy chain | 125 |
| | Amino acid sequence encoding the variable region of the heavy chain | 126 |
| | Nucleotide sequence encoding the variable region of the light chain | 127 |
| | Amino acid sequence encoding the variable region of the light chain | 128 |
| 1.4.1 | Nucleotide sequence encoding the variable region of the heavy chain | 129 |
| | Amino acid sequence encoding the variable region of the heavy chain | 130 |
| | Nucleotide sequence encoding the variable region of the light chain | 131 |
| | Amino acid sequence encoding the variable region of the light chain | 132 |
| 3.14.1 | Nucleotide sequence encoding the variable region of the heavy chain | 133 |
| | Amino acid sequence encoding the variable region of the heavy chain | 134 |
| | Nucleotide sequence encoding the variable region of the light chain | 135 |
| | Amino acid sequence encoding the variable region of the light chain | 136 |
| 3.8 | Nucleotide sequence encoding the variable region of the heavy chain | 137 |
| | Amino acid sequence encoding the variable region of the heavy chain | 138 |
| | Nucleotide sequence encoding the variable region of the light chain | 139 |
| | Amino acid sequence encoding the variable region of the light chain | 140 |
| 4.8.1 | Nucleotide sequence encoding the variable region of the heavy chain | 141 |
| | Amino acid sequence encoding the variable region of the heavy chain | 142 |
| | Nucleotide sequence encoding the variable region of the light chain | 143 |
| | Amino acid sequence encoding the variable region of the light chain | 144 |
| 5.1 | Nucleotide sequence encoding the variable region of the heavy chain | 145 |
| | Amino acid sequence encoding the variable region of the heavy chain | 146 |
| | Nucleotide sequence encoding the variable region of the light chain | 147 |
| | Amino acid sequence encoding the variable region of the light chain | 148 |

Definitions

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the instant application. See, e.g., Sambrook et al., *Molecular Cloning: A Laboratory Manual* (2d ed., Cold Spring Harbor Laboratory Press, Cold Spring Harbor, N.Y. 1989), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the embodiments provided herein, the following terms, unless otherwise indicated, shall be understood to have the following meanings:

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa light chain immunoglobulin molecules, and vice versa, as well as fragments and analogs thereof.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See M. O. Dayhoff, in *Atlas of Protein Sequence and Structure*, Vol. 5, 101-110 and Supplement 2 to Vol. 5, 1-10 (National Biomedical Research Foundation 1972). The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a "GTATA".

The following terms are used to describe the sequence relationships between two or more polynucleotide or amino acid sequences: "reference sequence," "comparison window," "sequence identity," "percentage of sequence identity," and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window," as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* (2d ed., Golub, E. S. and Gren, D. R. eds., Sinauer Associates, Sunderland, Mass. 1991), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the invention described herein. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the invention described herein, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al., *Science* 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally occurring peptide sequence. For example, single or multiple amino acid substitutions (preferably conservative amino acid substitutions) may be made in the naturally occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, ed., W. H. Freeman and Company, New York 1984); *Introduction to Protein Structure* (Branden, C. and Tooze, J. eds., Garland Publishing, New York, N.Y. 1991); and Thornton et al., *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to a MCP-1, under suitable binding conditions, (2) ability to block appropriate MCP-1 binding, or (3) ability to inhibit MCP-1 expressing cell growth in vitro or in vivo. Typically, polypeptide analogs comprise a conservative amino acid substitution (or addition or deletion) with respect to the naturally occurring sequence. Analogs typically are at least 20 amino acids long, preferably at least 50 amino acids long or longer, and can often be as long as a full-length naturally occurring polypeptide.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.* 15:29 (1986); Veber and Freidinger, *TINS* p. 392 (1985); and Evans et al., *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, —CH(OH) CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is said to specifically bind an antigen when the dissociation constant is $\leq 1$ µM, preferably $\leq 100$ nM and most preferably $\leq 10$ nM.

The term "agent" is used herein to denote a chemical compound, a mixture of chemical compounds, a biological macromolecule, or an extract made from biological materials.

"Active" or "activity" for the purposes herein refers to form(s) of MCP-1 polypeptide which retain a biological and/or an immunological activity of native or naturally occurring MCP-1 polypeptides, wherein "biological" activity refers to a biological function (either inhibitory or stimulatory) caused by a native or naturally occurring MCP-1 polypeptide other than the ability to induce the production of an antibody against an antigenic epitope possessed by a native or naturally occurring MCP-1 polypeptide and an "immunological" activity refers to the ability to induce the production of an antibody against an antigenic epitope possessed by a native or naturally occurring MCP-1 polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Mammal" refers to any animal classified as a mammal, including humans, other primates, such as monkeys, chimpanzees and gorillas, domestic and farm animals, and zoo, sports, laboratory, or pet animals, such as dogs, cats, cattle, horses, sheep, pigs, goats, rabbits, rodents, etc. For purposes of treatment, the mammal is preferably human.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an "F(ab')$_2$" fragment that has two antigen-combining sites and is still capable of cross-linking antigen.

"Fv" is the minimum antibody fragment that contains a complete antigen-recognition and binding site of the antibody. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, for example, even a single variable domain (e.g., the VH or VL portion of the Fv dimer or half of an Fv comprising only three CDRs specific for an antigen) may have the ability to recognize and bind antigen, although, possibly, at a lower affinity than the entire binding site.

A Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. F(ab')$_2$ antibody fragments originally were produced as pairs of Fab' fragments which have hinge cysteines between them. Other chemical couplings of antibody fragments are also known.

"Solid phase" means a non-aqueous matrix to which the antibodies described herein can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phases can comprise the well of an assay plate; in others it is a purification column (e.g., an affinity chromatography column). This term also includes a discontinuous solid phase of discrete particles, such as those described in U.S. Pat. No. 4,275,149.

The term "liposome" is used herein to denote a small vesicle composed of various types of lipids, phospholipids and/or surfactant which is useful for delivery of a drug (such as a MCP-1 polypeptide or antibody thereto) to a mammal. The components of the liposomes are commonly arranged in a bilayer formation, similar to the lipid arrangement of biological membranes.

The term "small molecule" is used herein to describe a molecule with a molecular weight below about 500 Daltons.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

Antibody Structure

The basic antibody structural unit is known to comprise a tetramer. Each tetramer is composed of two identical pairs of polypeptide chains, each pair having one "light" (about 25 kDa) and one "heavy" chain (about 50 to 70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody-binding site. Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md. 1991) (1987), or Chothia and Lesk, *J. Mol. Biol.* 196:901-17 (1987); Chothia et al., *Nature* 342:878-83 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin. Exp. Immunol.* 79: 315-21 (1990); Kostelny et al., *J. Immunol.* 148:1547-53 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies and Humanization of Antibodies

Human antibodies avoid certain of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of human antibody function into a rodent so that the rodent produces fully human antibodies.

Human Antibodies

One method for generating fully human antibodies is through the use of XenoMouse® strains of mice that have been engineered to contain human heavy chain and light chain genes within their genome. For example, a XenoMouse® mouse containing 245 kb and 190 kb-sized germline configuration fragments of the human heavy chain locus and kappa light chain locus is described in Green et al., *Nature Genetics* 7:13-21 (1994). The work of Green et al. was extended to the introduction of greater than approximately 80% of the human antibody repertoire through utilization of megabase-sized, germline configuration YAC fragments of the human heavy chain loci and kappa light chain loci, respectively. See Mendez et al., *Nature Genetics* 15:146-56 (1997) and U.S. patent application Ser. No. 08/759,620, filed Dec. 3, 1996, the disclosures of which are hereby incorporated by reference. Further, XenoMouse® mice have been generated that contain the entire lambda light chain locus (U.S. Patent Application Ser. No. 60/334,508, filed Nov. 30, 2001). And, XenoMouse® mice have been generated that produce multiple isotypes (see, e.g., WO 00/76310). XenoMouse® strains are available from Abgenix, Inc. (Fremont, Calif.).

The production of XenoMouse® mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. *Nature Genetics* 15:146-156 (1997) and Green and Jakobovits *J. Exp. Med.*, 188:483-495 (1998). See also European Patent No., EP 463,151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661, 016, 5,770,429, 5,789,650, 5,814,318, 5,877,397, 5,874,299, and 6,255,458 each to Lonberg and Kay, U.S. Pat. Nos. 5,591, 669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053, 131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 546,073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., (1992), Chen et al., (1993), Tuaillon et al., (1993), Choi et al., (1993), Lonberg et al., (1994), Taylor et al., (1994), and Tuaillon et al., (1995), Fishwild et al., (1996), the disclosures of which are hereby incorporated by reference in their entirety.

Kirin has demonstrated the generation of human antibodies from mice in which, through microcell fusion, large pieces of chromosomes, or entire chromosomes, have been introduced. See European Patent Application Nos. 773,288 and 843,961, the disclosures of which are hereby incorporated by reference.

Lidak Pharmaceuticals (now Xenorex) has also demonstrated the generation of human antibodies in SCID mice modified by injection of non-malignant mature peripheral leukocytes from a human donor. The modified mice exhibit an immune response characteristic of the human donor upon stimulation with an immunogen, which consists of the production of human antibodies. See U.S. Pat. Nos. 5,476,996 and 5,698,767, the disclosures of which are herein incorporated by reference.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against MCP-1 in order to vitiate concerns and/or effects of HAMA or HACA response.

Humanization and Display Technologies

As discussed above in connection with human antibody generation, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art. See e.g., Winter and Harris, *Immunol Today* 14:43-46 (1993) and Wright et al., *Crit. Reviews in Immunol.* 12:125-168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693, 761, 5,693,792, 5,714,350, and 5,777,085). Also, the use of Ig cDNA for construction of chimeric immunoglobulin genes is known in the art (Liu et al., *P.N.A.S.* 84:3439 (1987) and *J. Immunol.* 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al., "Sequences of Proteins of Immunological Interest," N.I.H. publication no. 91-3242 (1991). Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab').sub.2 and Fab may be prepared by cleavage of the intact protein, e.g., by protease or chemical cleavage. Alternatively, a truncated gene is designed. For example, a chimeric gene encoding a portion of the $F(ab')_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al., *Mol. Cell. Bio.* 3:280 (1983)), Rous sarcoma virus LTR (Gorman et al., *P.N.A.S.* 79:6777 (1982)), and moloney murine leukemia virus LTR (Grosschedl et al., *Cell* 41:885 (1985)). Also, as will be appreciated, native Ig promoters and the like may be used.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau, *PNAS USA* 94:4937-4942 (1997) (ribosomal display), Parmley and Smith, *Gene* 73:305-318 (1988) (phage display), Scott, *TIBS* 17:241-245 (1992), Cwirla et al., *PNAS USA* 87:6378-6382 (1990), Russel et al., *Nucl. Acids Res.* 21:1081-1085 (1993), Hoganboom et al., *Immunol. Reviews* 130:43-68 (1992), Chiswell and McCafferty, *TIBTECH* 10:80-84 (1992), and U.S. Pat. No. 5,733,743. If display technologies are utilized to produce antibodies that are not human, such antibodies can be humanized as described above.

Using these techniques, antibodies can be generated against MCP-1 expressing cells, MCP-1 itself, forms of MCP-1, epitopes or peptides thereof, and expression libraries thereto (see, e.g., U.S. Pat. No. 5,703,057) which can thereafter be screened as described above for the activities described above.

Preparation of Antibodies

Antibodies in accordance with the invention were prepared through the utilization of the XenoMouse® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the Background, herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al., *Nature Genetics* 15:146-156 (1997), the disclosure of which is hereby incorporated by reference.

Antibodies, as described herein, are neutralizing high affinity antibodies to human MCP-1. Further, in some embodiments, the antibodies cross react with rat MCP-1. Several different methods have been used historically to generate monoclonal antibodies or polyclonal antibodies against the N-terminus of human MCP-1. These approaches have included immunizing with full length human MCP-1 (hMCP-1) or bovine MCP-1 (bMCP-1) (Vieira et al., *Braz. J. Med. Biol. Res.* 21:1005-1011 (1988)), synthetic peptides of human MCP-1 (1-34 or 1-37) (Visser et al., *Acta Endocrinol.* 90:90-102 (1979)); Logue et al., *J. Immunol. Methods* 137:159-66 (1991)), and multiple antigenic peptides (MAP) of hMCP-1 (1-10), hMCP-1 (9-18) and hMCP-1 (24-37) (Magerlein et al., *Drug Res.* 48:783-87 (1998)). These approaches did not produce antibodies suitable for human therapeutics. (See section entitled "Therapeutic Administration and Formulation" herein for therapeutic criteria.) High affinity antibodies to hMCP-1 are difficult to make because of B cell tolerance to the peptide. However, Bradwell et al., (1999) have demonstrated that immunization with a mixture of human MCP-1 (1-34) and bovine MCP-1 (1-34) MAPs followed by a mixture of human and bovine MAPs targeting the hMCP-1(51-84) and bMCP-1(51-86) was effective in breaking B-cell tolerance to MCP-1 in a human patient with an inoperable parathyroid tumor.

The approach described herein was designed to overcome B-cell tolerance to hMCP-1 as well as to produce a fully human monoclonal antibody suitable for therapeutic and diagnostic use. XenoMouse® animals were immunized with synthetic peptides of MCP-1 (hMCP-1(1-34) and rMCP-1(1-34)), because synthetic peptides have been successfully used to generate antibodies specific to endogenous human MCP-1 (Visser et al., (1979)). Furthermore, because the N-terminus of murine MCP-1 is highly conserved with human MCP-1 (85% identity) and rat MCP-1 (91%), the combination of peptides was used as an immunogen to break B-cell tolerance to murine MCP-1 through molecular mimicry, thereby allowing the generation of high affinity human anti-human MCP-1 antibodies. These peptides were both coupled to keyhole limpet hemocyanin and emulsified in complete Freund's adjuvant or incomplete Freund's adjuvant to enhance the immunogenicity of these proteins.

After immunization, lymphatic cells (such as B cells) were recovered from the mice that expressed antibodies, and such recovered cell lines fused with a myeloid-type cell line to prepare immortal hybridoma cell lines. Such hybridoma cell lines were screened and selected to identify hybridoma cell lines that produced antibodies specific to the antigen of interest. Herein, the production of multiple hybridoma cell lines that produce antibodies specific to MCP-1 is described. Further, a characterization of the antibodies produced by such cell lines is provided, including nucleotide and amino acid sequence analyses of the heavy and light chains of such antibodies.

Embodiments of the invention provide for the production of multiple hybridoma cell lines that produce antibodies specific to MCP-1. Further embodiments relate to antibodies that bind to and neutralize the activity of the MCP-1 family members including MCP-2, MCP-3, and MCP-4. The supernatants are also screened for immunoreactivity against fragments of MCP-1 to further epitope map the different antibodies against related human chemokines and against rat MCP-1 and the mouse ortholog of MCP-1, JE, to determine species cross-reactivity. Further embodiments provide a characterization of the antibodies produced by such cell lines, including nucleotide and amino acid sequence analyses of the heavy and light chains of such antibodies.

Alternatively, instead of being fused to myeloma cells to generate hybridomas, B cells may be directly assayed. For example, CD19+B cells may be isolated from hyperimmune XenoMouse® mice and allowed to proliferate and differentiate into antibody-secreting plasma cells. Antibodies from the cell supernatants are then screened by ELISA for reactivity against the MCP-1 immunogen. The supernatants are also screened for immunoreactivity against fragments of MCP-1 to further epitope map the different antibodies against related human chemokines and against rat MCP-1 and the mouse ortholog of MCP-1, JE, to determine species cross-reactivity. Single plasma cells secreting antibodies with the desired specificities are then isolated using a MCP-1-specific hemolytic plaque assay (Babcook et al., *Proc. Natl. Acad. Sci. USA*, 93:7843-7848 (1996)). Cells targeted for lysis are preferably sheep red blood cells (SRBCs) coated with the MCP-1 antigen. In the presence of a B cell culture containing plasma cells secreting the immunoglobulin of interest and complement, the formation of a plaque indicates specific MCP-1-mediated lysis of the sheep red blood cells surrounding the plasma cell of interest. The single antigen-specific plasma cell in the center of the plaque can be isolated and the genetic information that encodes the specificity of the antibody is isolated from the single plasma cell. Using reverse-transcriptase PCR, the DNA encoding the heavy and light chain variable regions of the antibody can be cloned. Such cloned DNA can then be further inserted into a suitable expression vector, preferably a vector cassette such as a pcDNA, more preferably such a pcDNA vector containing the constant domains of immunoglobulin heavy and light chain. The generated vector can then be transfected into host cells, preferably CHO cells, and cultured in conventional nutrient media modified as appropriate for inducing promoters, selecting transformants, or amplifying the genes encoding the desired sequences. The isolation of multiple single plasma cells that produce antibodies specific to MCP-1 is described below. Further, the genetic material that encodes the specificity of the anti-MCP-1 antibody can be isolated, introduced into a suitable expression vector that can then be transfected into host cells.

In general, antibodies produced by the fused hybridomas were human IgG2 heavy chains with fully human kappa or lambda light chains. In some embodiments, antibodies possess human IgG4 heavy chains as well as IgG2 heavy chains. Antibodies may also be of other human isotypes, including IgG1. The antibodies possessed high affinities, typically possessing a $K_D$ of from about $10^{-6}$ through about $10^{-12}$ M or below, when measured by either solid phase and solution phase. Antibodies possessing a $K_D$ of at least $10^{-11}$ M are preferred to inhibit the activity of MCP-1.

Regarding the importance of affinity to therapeutic utility of anti-MCP-1 antibodies, it will be understood that one can generate anti-MCP-1 antibodies, for example, combinatorially, and assess such antibodies for binding affinity. One approach that can be utilized is to take the heavy chain cDNA from an antibody, prepared as described above and found to have good affinity to MCP-1, and combine it with the light chain cDNA from a second antibody, prepared as described above and also found to have good affinity to MCP-1, to produce a third antibody. The affinities of the resulting third antibodies can be measured as described herein and those with desirable dissociation constants isolated and characterized. Alternatively, the light chain of any of the antibodies described above can be used as a tool to aid in the generation of a heavy chain that when paired with the light chain will exhibit a high affinity for MCP-1, or vice versa. These heavy chain variable regions in this library could be isolated from naïve animals, isolated from hyperimmune animals, generated artificially from libraries containing variable heavy chain sequences that differ in the CDR regions, or generated by any other methods that produce diversity within the CDR regions of any heavy chain variable region gene (such as random or directed mutagenesis). These CDR regions, and in particular CDR3, may be a significantly different length or sequence identity from the heavy chain initially paired with the original antibody. The resulting library could then be screened for high affinity binding to MCP-1 to generate a therapeutically relevant antibody molecule with similar properties as the original antibody (high affinity and neutralization). A similar process using the heavy chain or the heavy chain variable region can be used to generate a therapeutically relevant antibody molecule with a unique light chain variable region. Furthermore, the novel heavy chain variable region, or light chain variable region, can then be used in a similar fashion as described above to identify a novel light chain variable region, or heavy chain variable region, that allows the generation of a novel antibody molecule.

Another combinatorial approach that can be utilized is to perform mutagenesis on germ line heavy and/or light chains that are demonstrated to be utilized in the antibodies in accordance with the invention described herein, particularly in the complementarity determining regions (CDRs). The affinities of the resulting antibodies can be measured as described herein and those with desirable dissociation constants isolated and characterized. Upon selection of a preferred binder, the sequence or sequences encoding the same may be used to generate recombinant antibodies as described above. Appropriate methods of performing mutagenesis on an oligonucleotide are known to those skilled in the art and include chemical mutagenesis, for example, with sodium bisulfite, enzymatic misincorporation, and exposure to radiation. It is understood that the invention described herein encompasses antibodies with substantial identity, as defined herein, to the antibodies explicitly set forth herein, whether produced by mutagenesis or by any other means. Further, antibodies with conservative or non-conservative amino acid substitutions, as defined herein, made in the antibodies explicitly set forth herein, are included in embodiments of the invention described herein.

Another combinatorial approach that can be used is to express the CDR regions, and in particular CDR3, of the antibodies described above in the context of framework regions derived from other variable region genes. For example, CDR1, CDR2, and CDR3 of the heavy chain of one anti-MCP-1 antibody could be expressed in the context of the framework regions of other heavy chain variable genes. Similarly, CDR1, CDR2, and CDR3 of the light chain of an anti-MCP-1 antibody could be expressed in the context of the framework regions of other light chain variable genes. In addition, the germline sequences of these CDR regions could be expressed in the context of other heavy or light chain variable region genes. The resulting antibodies can be assayed for specificity and affinity and may allow the generation of a novel antibody molecule.

As will be appreciated, antibodies prepared in accordance with the invention described herein can be expressed in various cell lines. Sequences encoding particular antibodies can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive MCP-1 binding properties.

Additional Criteria for Antibody Therapeutics

As discussed herein, the function of the MCP-1 antibody appears important to at least a portion of its mode of operation. The anti-MCP-1 antibodies of the instant invention may be made capable of effector function, including complement-dependent cytotoxicity (CDC) and antibody-dependent cellular cytotoxicity (ADCC). There are a number of isotypes of antibodies that are capable of the same, including, without limitation, the following: murine IgM, murine IgG2a, murine IgG2b, murine IgG3, human IgM, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see, e.g., U.S. Pat. No. 4,816,397 and U.S. Pat. No. 6,331,415), cell-cell fusion techniques (see, e.g., U.S. Pat. Nos. 5,916,771 and 6,207,418), among others.

In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

By way of example, the MCP-1 antibodies discussed herein are human anti-MCP-1 IgG2 and IgG4 antibodies. If such antibody possessed desired binding to the MCP-1 molecule, it could be readily isotype switched to generate a human IgM, human IgG1, or human IgG3, IgA1 or IgGA2 isotypes, while still possessing the same variable region (which defines the antibody's specificity and some of its affinity). Such molecule would then be capable of fixing complement and participating in CDC.

Accordingly, as antibody candidates are generated that meet desired "structural" attributes as discussed above, they can generally be provided with at least certain of the desired "functional" attributes through isotype switching.

Epitope Mapping

Immunoblot Analysis

The binding of the antibodies described herein to MCP-1 can be examined by a number of methods. For example, MCP-1 may be subjected to SDS-PAGE and analyzed by immunoblotting. The SDS-PAGE may be performed either in the absence or presence of a reduction agent. Such chemical modifications may result in the methylation of cysteine residues. Accordingly, it is possible to determine whether the anti-MCP-1 antibodies described herein bind to a linear epitope on MCP-1.

Surface-Enhanced Laser Desorption/Ionization (SELDI)

Epitope mapping of the epitope for the MCP-1 antibodies described herein can also be performed using SELDI. SELDI ProteinChip® arrays are used to define sites of protein-protein interaction. Antigens are specifically captured on antibodies covalently immobilized onto the Protein Chip array surface by an initial incubation and wash. The bound antigens can be detected by a laser-induced desorption process and analyzed directly to determine their mass. Such fragments of the antigen that bind are designated as the "epitope" of a protein.

The SELDI process enables individual components within complex molecular compositions to be detected directly and mapped quantitatively relative to other components in a rapid, highly-sensitive and scalable manner. SELDI utilizes a diverse array of surface chemistries to capture and present large numbers of individual protein molecules for detection by a laser-induced desorption process. The success of the SELDI process is defined in part by the miniaturization and integration of multiple functions, each dependent on different technologies, on a surface ("chip"). SELDI BioChips and other types of SELDI probes are surfaces "enhanced" such that they become active participants in the capture, purification (separation), presentation, detection, and characterization of individual target molecules (e.g., proteins) or population of molecules to be evaluated.

A single SELDI protein BioChip, loaded with only the original sample, can be read thousands of times. The SELDI protein BioChips from LumiCyte hold as many as 10,000 addressable protein docking locations per 1 square centimeter. Each location may reveal the presence of dozens of individual proteins. When the protein composition information from each location is compared and unique information sets combined, the resulting composition map reveals an image with sets of features that are used collectively to define specific patterns or molecular "fingerprints." Different fingerprints may be associated with various stages of health, the onset of disease, or the regression of disease associated with the administration of appropriate therapeutics.

The SELDI process may be described in further detail in four parts. Initially, one or more proteins of interest are captured or "docked" on the ProteinChip Array, directly from the original source material, without sample preparation and without sample labeling. In a second step, the "signal-to-noise" ratio is enhanced by reducing the chemical and biomolecular "noise." Such "noise" is reduced through selective retention of target on the chip by washing away undesired materials. Further, one or more of the target protein(s) that are captured are read by a rapid, sensitive, laser-induced process (SELDI) that provides direct information about the target (molecular weight). Lastly, the target protein at any one or more locations within the array may be characterized in situ by performing one or more on-the-chip binding or modification reactions to characterize protein structure and function.

Phage Display

The epitope for the anti-MCP-1 antibodies described herein can be determined by exposing the ProteinChip Array to a combinatorial library of random peptide 12-mer displayed on Filamentous phage (New England Biolabs).

Phage display describes a selection technique in which a peptide is expressed as a fusion with a coat protein of a bacteriophage, resulting in display of the fused protein on the surface of the virion. Panning is carried out by incubation of a library of phage displayed peptide with a plate or tube coated with the target, washing away the unbound phage, and eluting the specifically bound phage. The eluted phage is then amplified and taken through additional binding and amplification cycles to enrich the pool in favor of binding sequences. After three or four rounds, individual clones binding are further tested for binding by phage ELISA assays performed on antibody-coated wells and characterized by specific DNA sequencing of positive clones.

After multiple rounds of such panning against the anti-MCP-1 antibodies described herein, the bound phage may be eluted and subjected to further studies for the identification and characterization of the bound peptide.

Monoclonal antibodies of the invention were shown to bind important residues in the core domain of MCP-1. The neutralizing monoclonal antibodies studied discriminate two functionally important sites in human MCP-1, involved with two residues that were previously shown to be required for binding to the receptor. One site was recognized by all tested antibodies, which competed with the receptor protein for MCP-1 binding and involved Arg 24. The second site was detected by the group of six antibodies that bound the conformational epitope, and their binding site appeared to involve Arg24 and Lys35, which are held in close proximity to the N-terminus by virtue of a disulfide bond between C11 and C36.

The MCP-1 variants described herein have been analyzed before with respect to biological activity, physical receptor binding and structural integrity (Jamagin et al., (1999) *Biochemistry* 38: 16167-16177; Hemmerich et al, (1999) *Biochemistry* 38: 13013-13025) and provided valuable tools in determining the binding epitopes of the antibodies as described below.

Anti MCP-1 antibody 3.11.1 recognizes a conformational epitope and differs from other antibodies by its unique sequence of heavy and light chain, and its ability to cross-react with, and to cross-neutralize, other members of the MCP family, such as MCP-2, MCP-3 and MCP-4. As shown by the mutagenesis experiments, the binding site of mAb 3.11.1 was affected by the change R24A but not by K35A. These data are confirmed by the Lyc-C on chip digest result with SELDI, which delimits the binding epitope to be between residues 20-35 of MCP-1.

Determination that the epitope for 3.11.1 is between residues 20-35 was also supported by sequence alignment showing that R24, but not K35, was conserved across other members of the MCP family, specifically MCP-2, MCP-3 and MCP-4. Binding analyses by means of SPOTs peptide synthesized on membrane (Sigma-Genosys, The Woodlands, Tex.) revealed that binding site for at least eight mAbs with linear epitopes involved residues 20-25, and included R24. Given the similarities in the results in these binding studies and the significant homology between the variable gene structures for all the mAbs binding to linear epitopes on MCP-1, it appears that the antibodies all bind to this neutralizing epitope.

The cluster of the epitope around R24 and K35 explains the neutralizing activity of all 36 antibodies. The recognized epitope on MCP-1 does not appear to extend to the N-terminal residues up to Pro9. This residue appears to affect receptor signaling, but not binding affinity.

Diagnostic Use

Antibodies prepared in accordance with embodiments of the invention described herein are useful for assays, particularly in vitro diagnostic assays, for example, for use in determining the level of MCP-1 and all MCP-1 family members in patient samples. The patient samples can be, for example, bodily fluids, preferably blood, more preferably blood serum, synoival fluid, tissue lysates, and extracts prepared from diseased tissues. Examples of diagnostic assays include measuring the level of MCP family chemokines in, for example, human serum, synovial fluid and tissue lysates. Monitoring the level of specific MCP family members may be used as a surrogate measure of patient response to treatment and as a method of monitoring the severity of the disease in a patient. Elevated levels of MCP-1 compared to levels of other soluble markers would indicate the presence of inflammation. The concentration of the MCP-1 antigen present in patient samples is determined using a method that specifically determines the amount of the antigen that is present. Such a method includes an ELISA method in which, for example, antibodies of the invention may be conveniently immobilized on an insoluble matrix, such as a polymer matrix. Using a population of samples that provides statistically significant results for each stage of progression or therapy, a range of concentrations of the antigen that may be considered characteristic of each stage of disease can be designated.

In order to determine the degree of inflammation in a subject under study, or to characterize the response of the subject to a course of therapy, a sample of blood is taken from the subject and the concentration of the MCP-1 antigen present in the sample is determined. The concentration so obtained is used to identify in which range of concentrations the value falls. The range so identified correlates with a stage of disease progression or a stage of therapy identified in the various populations of diagnosed subjects, thereby providing a stage in the subject under study.

Gene amplification and/or expression may be measured in a sample directly, for example, by conventional Southern blotting, Northern blotting to quantitate the transcription of mRNA (Thomas, *Proc. Natl. Acad. Sci. USA*, 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay can be carried out where the duplex is bound to a surface, so that upon the formation of duplex on the surface, the presence of antibody bound to the duplex can be detected.

For example, antibodies, including antibody fragments, can be used to qualitatively or quantitatively detect the expression of MCP-1 proteins. As noted above, the antibody preferably is equipped with a detectable, e.g., fluorescent label, and binding can be monitored by light microscopy, flow cytometry, fluorimetry, or other techniques known in the art. These techniques are particularly suitable if the amplified gene encodes a cell surface protein, e.g., a growth factor. Such binding assays are performed as known in the art.

In situ detection of antibody binding to the MCP-1 protein can be performed, for example, by immunofluorescence or immunoelectron microscopy. For this purpose, a tissue specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

One of the most sensitive and most flexible quantitative methods for quantitating differential gene expression is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step in this process is the isolation of mRNA from a target sample. The starting material is typically total RNA isolated from a disease tissue and corresponding normal tissues, respectively. Thus, mRNA can be extracted, for example, from frozen or archived paraffin-embedded and fixed (e.g. formalin-fixed) samples of diseased tissue for comparison with normal tissue of the same type. Methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.*, 56:A67 (1987), and De Andrés et al., *BioTechniques*, 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Total RNA from tissue samples can be isolated using RNA Stat-60 (Tel-Test).

As RNA cannot serve as a template for PCR, the first step in differential gene expression analysis by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' endonuclease activity. Thus, TaqMan PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicontypical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan RT-PCR can be performed using commercially available equipments, such as, for example, ABI PRIZM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRIZM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct). The $\Delta$Ct values are used as quantitative measurement of the relative number of starting copies of a particular target sequence in a nucleic acid sample when comparing the expression of RNA in a cell from a diseased tissue with that from a normal cell.

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and $\beta$-actin.

Differential gene expression can also be identified, or confirmed using the microarray technique. In this method, nucleotide sequences of interest are plated, or arrayed, on a microchip substrate. The arrayed sequences are then hybridized with specific DNA probes from cells or tissues of interest.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip selectively hybridize to each spot of DNA on the array. After stringent washing to remove non-specifically bound probes, the chip is scanned by confocal laser microscopy. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA*, 93(20)L106-49). The methodology of hybridization of nucleic acids and microarray technology is well known in the art.

MCP-1 Agonists and Antagonists

Embodiments of the invention described herein also pertain to variants of a MCP-1 protein that function as either MCP-1 agonists (mimetics) or as MCP-1 antagonists. Variants of a MCP-1 protein can be generated by mutagenesis, e.g., discrete point mutation or truncation of the MCP-1 protein. An agonist of the MCP-1 protein can retain substantially the same, or a subset of, the biological activities of the naturally occurring form of the MCP-1 protein. An antagonist of the MCP-1 protein can inhibit one or more of the activities of the naturally occurring form of the MCP-1 protein by, for example, competitively binding to a downstream or upstream member of a cellular signaling cascade which includes the MCP-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the MCP-1 protein.

Variants of the MCP-1 protein that function as either MCP-1 agonists (mimetics) or as MCP-1 antagonists can be identified by screening combinatorial libraries of mutants, e.g., truncation mutants, of the MCP-1 protein for protein agonist or antagonist activity. In one embodiment, a variegated library of MCP-1 variants is generated by combinatorial mutagenesis at the nucleic acid level and is encoded by a variegated gene library. A variegated library of MCP-1 variants can be produced by, for example, enzymatically ligating a mixture of synthetic oligonucleotides into gene sequences such that a degenerate set of potential MCP-1 sequences is expressible as individual polypeptides, or alternatively, as a set of larger fusion proteins (e.g., for phage display) containing the set of MCP-1 sequences therein. There are a variety of methods which can be used to produce libraries of potential MCP-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential MCP-1 variant sequences. Methods for synthesizing degenerate oligonucleotides are known in the art (see, e.g., Narang, *Tetrahedron* 39:3 (1983); Itakura et al., *Annu. Rev. Biochem.* 53:323 (1984); Itakura et al., *Science* 198:1056 (1984); Ike et al., *Nucl. Acid Res.* 11:477 (1983).

Design and Generation of Other Therapeutics

In accordance with embodiments of the invention described herein and based on the activity of the antibodies that are produced and characterized herein with respect to MCP-1, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

In connection with the generation of advanced antibody therapeutics, where complement fixation is a desirable attribute, it may be possible to sidestep the dependence on complement for cell killing through the use of bispecifics, immunotoxins, or radiolabels, for example.

For example, in connection with bispecific antibodies, bispecific antibodies can be generated that comprise (i) two antibodies one with a specificity to MCP-1 and another to a second molecule that are conjugated together, (ii) a single antibody that has one chain specific to MCP-1 and a second chain specific to a second molecule, or (iii) a single chain antibody that has specificity to MCP-1 and the other molecule. Such bispecific antibodies can be generated using techniques that are well known for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer (Suppl.)* 7:51-52 (1992). In each case, the second specificity can be made to the heavy chain activation receptors, including, without limitation, CD16 or CD64 (see e.g., Deo et al. 18:127 (1997)) or CD89 (see e.g., Valerius et al. *Blood* 90:4485-4492 (1997)).

In connection with immunotoxins, antibodies can be modified to act as immunotoxins utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), U.S. Pat. Nos. 5,648,471, and 5,697,902.

Therapeutic Administration and Formulations

Biologically active anti-MCP-1 antibodies prepared in accordance with the invention described herein may be used in a sterile pharmaceutical preparation or formulation to neutralize the activity of MCP-1 produced in diseased and inflamed tissues, thereby preventing the further infiltration of mononuclear cells into tissues. Such diseased and inflamed tissues occur in many types of human cancer, including breast, ovarian and lung cancer, and in conditions such as glomerulonephritis, artheriosclerosis, and multiple sclerosis. The biologically active anti-MCP-1 antibody of the instant invention may be employed alone or in combination with other therapeutic agents. For cancer, the anti-MCP-1 antibodies may be combined with traditional modes of chemotherapy such as taxol, doxorubicin, cis-platinum, 5-fluorouracil and other novel inhibitors of the angiogenic process. For treating inflammatory disease, the MCP-1 antibodies may be combined with steroids or antibodies to other cytokines and chemokines that contribute to the disease state.

When used for in vivo administration, the antibody formulation may be sterile. This can be readily accomplished by filtration through sterile filtration membranes, prior to or following lyophilization and reconstitution. The antibody ordinarily will be stored in lyophilized form or in solution. Therapeutic antibody compositions generally are placed into a container having a sterile access port, for example, an intravenous solution bag or vial having a stopper pierceable by a hypodermic injection needle.

The route of antibody administration can be in accord with known methods, e.g., injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

The antibodies of the invention may be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systematically, the therapeutic composition should be sterile, pyrogen-free and in a parenterally acceptable solution having due regard for pH, isotonicity, and stability. These conditions are known to those skilled in the art. Briefly, dosage formulations of the compounds of embodiments of the invention described herein are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington's Pharmaceutical Sciences* (18$^{th}$ ed, Mack Publishing Company, Easton, Pa. (1990)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, 15:167-277 (1981) and Langer, Chem. Tech., 12:98-105 (1982) or poly(vinylalcohol)), polylactides (U.S. Pat. No. 3,773,919, EP 58,481), copolymers of L-glutamic acid and gamma ethyl-L-glutamate (Sidman et al., *Biopolymers*, 22:547-556 (1983)), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-release compositions also include liposomally entrapped antibodies of the invention. Liposomes containing such antibodies are prepared by methods known per se: U.S. Pat. No. DE 3,218,121; Epstein et al., *Proc. Natl. Acad. Sci. USA*, 82:3688-3692 (1985); Hwang et al., *Proc. Natl. Acad. Sci. USA*, 77:4030-4034 (1980); EP 52,322; EP 36,676; EP 88,046; EP 143,949; 142,641; Japanese patent application 83-118008; U.S. Pat. Nos. 4,485,045 and 4,544,545; and EP 102,324. The dosage of the antibody will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibody of the invention to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 0.001 mg/kg to up to 100 mg/kg or more, depending on the factors mentioned above. Desirable dosage concentrations include 0.001 mg/kg, 0.005 mg/kg, 0.01 mg/kg, 0.05 mg/kg, 0.1 mg/kg, 0.5 mg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, and 100 mg/kg or more. Typically, the clinician will administer the therapeutic antibody until a dosage is reached that achieves the desired effect. The progress of this therapy is easily monitored by conventional assays or as described herein.

EXAMPLES

The following examples, including the experiments conducted and results achieved are provided for illustrative purposes only and are not to be construed as limiting upon the embodiments of the invention described herein.

Example 1

MCP-1 Antigen Preparation

The human MCP-1 peptide used as the antigen in these studies had the following amino acid sequence:

```
QPDAINAPVTCCYNFTNRKISVQRLASYRRITSS  (SEQ ID NO: 149)
KCPKEAVIFKTIVAKEICADPKQKWVQDSMDHLD
KQTQTPKT
```

This peptide was expressed recombinantly in *E. coli* and purchased from Prepro Tech (Rocky Hill, N.J.).

Example 2

Anti-MCP-1 Antibodies

Antibody Generation

Immunization and selection of animals for harvesting by ELISA. Monoclonal antibodies against MCP-1 were developed by sequentially immunizing XenoMouse® mice (XenoMouse® strains XMG2, XMG4 (3C-1 strain), and a hybrid strain produced through the crossing of XMG2 with an XMG4 (3C-1 strain) mouse, Abgenix, Inc. Fremont, Calif.) according to the schedule shown in Table 2. For instance, the initial immunization was with 10 µg antigen admixed 1:1 v/v with TiterMax Gold. Subsequent boosts were made with 5 or 10 µg antigen admixed 1:1 v/v with 100 µg alum gel in pyrogen-free D-PBS. Some boosts were done with 50% TiterMax Gold, followed by three injections with 10 µg antigen admixed 1:1 v/v with 10 µg MCP-1 antigen in alum gel, and then a final boost of 10 µg antigen in PBS. In particular, each mouse was immunized in the footpad by subcutaneous injection. The animals were immunized on days 0, 4, 7, 10, 14, 18, 27, 31, 35 and 42. The animals were bled on days 13 and 26 to obtain sera for harvest selection as described below.

TABLE 2

| Group | Strain | # of mice | 1st injection | 2nd boost | 3rd boost | 4th boost | Bleed | 5th boost | 6th boost |
|---|---|---|---|---|---|---|---|---|---|
| 1 | xmg2 | 7 | 10 µg/ mouse | 5 µg// mouse | 5 µg/ mouse | 5 µg/ mouse | | 5 µg/ mouse | 5 µg/ mouse |
| 2 | 3C-1 | 7 | 10 µg// mouse | 5 ug/ mouse | 5 µg/ mouse | 5 µg/ mouse | | 5 µg/ mouse | 5 µg/ mouse |
| 3 | (3C-1) × xmg2 | 7 | 10 µg/ mouse TiterMax | 5 ug/ mouse Alum Gel | 5 µg/ mouse Alum Gel | 5 µg/ mouse Alum Gel | | 5 µg/ mouse Alum Gel | 5 µg/ mouse TiterMax |
| Day | | | 0 | 4 | 7 | 10 | 13 | 14 | 18 |

| Group | Strain | # of mice | | Bleed | 7th boost | 8th boost | 9th boost | 10th boost | Fusion |
|---|---|---|---|---|---|---|---|---|---|
| 1 | xmg2 | 7 | | | 10 µg/ mouse | 10 µg/ mouse | 10 µg/ mouse | 10 µg/ mouse | |
| 2 | 3C-1 | 7 | | | 10 µg/ mouse | 10 µg/ mouse | 10 µg/ mouse | 10 µg/ mouse | |
| 3 | (3C-1) × xmg2 | 7 | | | 10 µg/ mouse Alum Gel | 10 µg// mouse Alum Gel | 10 µg/ mouse Alum Gel | 10 µg/ mouse D-PBS | |
| Day | | | | 26 | 27 | 31 | 35 | 42 | 46 |

Similarly, other XenoMouse® mice (XenoMouse® strains XMG2 and XMG2L3) were sequentially immunized according to the schedule shown in Table 3.

TABLE 3

| Group | Strain | # of mice | 1st injection | 2nd boost | 3rd boost | 4th boost | Bleed | 5th boost | 6th boost | Fusion |
|---|---|---|---|---|---|---|---|---|---|---|
| 4 | xmg2 | 4 | 10 µg/ mouse | 10 µg/ mouse | 10 µg/ mouse | 10 µg/ mouse | | 10 µg/ mouse | 10 µg/ mouse | |
| 5 | xmg2L3 | 4 | 10 µg/ mouse TiterMax | 10 µg/ mouse Alum Gel | 10 µg/ mouse Alum Gel | 10 µg/ mouse Alum Gel | | 10 µg/ mouse Alum Gel | 10 µg/ mouse Alum Gel | |
| Day | | | 0 | 3 | 6 | 10 | 13 | 14 | 17 | 21 |

Anti-MCP-1 antibody titers were determined by indirect ELISA. The titer value the reciprocal of the greatest dilution of sera with an OD reading two-fold that of background. Briefly, MCP-1 (84mer; 1 µg/mL) was coated onto Costar Labcoat Universal Binding Polystyrene 96 well plates overnight at four degrees. The solution containing unbound MCP-1 was removed and the plates were treated with UV light (365 nm) for 4 minutes (4000 microjoules). The plates were washed five times with dH$_2$O. XenoMouse® sera from the MCP-1 immunized animals, or naïve XenoMouse® animals, were titrated in 2% milk/PBS at 1:2 dilutions in duplicate from a 1:100 initial dilution. The last well was left blank. The plates were washed five times with dH$_2$O.

A goat anti-human IgG Fc-specific HRP-conjugated antibody was added at a final concentration of 1 µg/mL for 1 hour at room temperature. The plates were washed five times with dH$_2$O. The plates were developed with the addition of TMB for 30 minutes and the ELISA was stopped by the addition of 1 M phosphoric acid. The specific titer of individual XenoMouse® animals was determined from the optical density at 450 nm and is shown in Tables 4, 5, 6, 7, and 8. The titer represents the reciprocal dilution of the serum and therefore the higher the number the greater the humoral immune response to MCP-1. Lymph nodes from all immunized XenoMouse® animals were harvested for fusion.

TABLE 4

Group 1, footpad, xmg2, 7 mice

| Mouse ID | bleed of Day 13 After 4 injections Reactivity to MCP-1 Titers via hIgG | bleed of Day 26 After 6 injections | fusion of Day 46 After 10 injections |
|---|---|---|---|
| N160-1 | 1,000 | 73,000 | 300,000 |
| N160-2 | 6,500 | 600,000 | 600,000 |
| N160-3 | 2,300 | 250,000 | 125,000 |
| N160-4 | 1,400 | 125,000 | 75,000 |
| N160-5 | 4,000 | 200,000 | 225,000 |
| N160-6 | 250 | 2,400 | 18,000 |
| N160-7 | 60 | 1,600 | 35,000 |
| NC | 175 | <100 | 200 |

TABLE 5

Group 2, footpad, 3c-1, 7 mice

| Mouse ID | bleed of Day 13 After 6 injections Reactivity to MCP-1 Titers via hIgG | fusion of Day 46 After 10 injections |
|---|---|---|
| M724-1 | 35,000 | 24,000 |
| M724-3 | 8,000 | 7,500 |
| M724-5 | 8,000 | 20,000 |
| N600-4 | 9,000 | 7,500 |
| N600-5 | 1,800 | 75,000 |
| N600-6 | 2,200 | 20,000 |
| N600-7 | 800 | 25,000 |
| NC | <100 | <100 |

TABLE 6

Group 3, footpad, 3c-1/xmg2 (F1), 7 mice

| Mouse ID | bleed of Day 13 After 4 injections Reactivity to MCP-1 Titers via hIgG | bleed of Day 26 After 6 injections | fusion of Day 46 After 10 injections |
|---|---|---|---|
| M219-1 | 50 | 2,200 | 8,000 |
| M219-2 | <100 | 9,000 | 18,000 |
| M246-3 | 800 | 7,000 | 18,000 |
| M246-5 | 850 | 18,000 | 65,000 |
| M246-9 | <100 | 18,000 | 55,000 |
| M344-6 | <100 | 800 | 12,000 |
| M344-10 | <100 | 6,000 | 25,000 |
| NC | 200 | 225 | 175 |

TABLE 7

Group 4, XMG2, footpad, 4 mice

Capture:

| | bleed of Day 13 after 4 injections | | bleed of Day 21 after 6 injections | |
|---|---|---|---|---|
| Mouse ID | Human MCP-1 Reactivity to MCP-1 Titers via hIgG | Human MCP-1 Reactivity to MCP-1 Titers via hL | Human MCP-1 Reactivity to MCP-1 Titers via hIgG | Human MCP-1 Reactivity to MCP-1 Titers via hL |
| N493-1 | <100 | <100 | 2,500 | <100 |
| N493-2 | <100 | <100 | 1,000 | <100 |
| N493-3 | 300 | <100 | 4,500 | <100 |
| N493-4 | 800 | <100 | 10,000 | <100 |
| NC | 900 | 100 | 600 | <100 |
| *PC | 8,000 | | 3,000 | |

TABLE 8

Group 5, XMG2L3, footpad, 4 mice

Capture:

| | bleed after 4 injections | | bleed of after 6 injections | |
|---|---|---|---|---|
| Mouse ID | Human MCP-1 Reactivity to MCP-1 Titers via hIgG | Human MCP-1 Reactivity to MCP-1 Titers via hL | Human MCP-1 Reactivity to MCP-1 Titers via hIgG | Human MCP-1 Reactivity to MCP-1 Titers via hL |
| N259-12 | 300 | 300 | 2,000 | 700 |
| N259-14 | 100 | 400 | 2,500 | 650 |
| N269-2 | 700 | 200 | 2,800 | 500 |
| N263-3 | 900 | 900 | 24,000 | 8,000 |

TABLE 8-continued

Group 5, XMG2L3, footpad, 4 mice

| | Capture: | | | |
|---|---|---|---|---|
| | bleed after 4 injections | | bleed of after 6 injections | |
| Mouse ID | Human MCP-1 Reactivity to MCP-1 Titers via hIgG | Human MCP-1 Reactivity to MCP-1 Titers via hL | Human MCP-1 Reactivity to MCP-1 Titers via hIgG | Human MCP-1 Reactivity to MCP-1 Titers via hL |
| NC | 900 | 100 | 600 | <100 |
| *PC | 8,000 | | 3,000 | |

*For Tables 4-8, NC (negative control) = XMG2 KLH group 1, footpad L627-6 PC (positive control) = XMG2 MCP-1 group 1, footpad N160-1

Recovery of lymphocytes, B-cell isolations, fusions and generation of hybridomas. Immunized mice were sacrificed by cervical dislocation, and the lymph nodes harvested and pooled from each cohort. The lymphoid cells were dissociated by grinding in DMEM to release the cells from the tissues and the cells were suspended in DMEM. The cells were counted, and 0.9 mL DMEM per 100 million lymphocytes added to the cell pellet to resuspend the cells gently but completely. Using 100 μL of CD90$^+$ magnetic beads per 100 million cells, the cells were labeled by incubating the cells with the magnetic beads at 4° C. for 15 minutes. The magnetically labeled cell suspension containing up to $10^8$ positive cells (or up to $2 \times 10^9$ total cells) was loaded onto a LS$^+$ column and the column washed with DMEM. The total effluent was collected as the CD90-negative fraction (most of these cells are B cells).

P3 myeloma cells and B cell-enriched lymph node cells were combined in a ratio of 1:1 (myeloma:lymph nodes) into a 50 mL conical tube in DMEM. The combined cells were centrifuged at 800×g (2000 rpm) for 5-7 minutes and the supernatant immediately removed from the resulting pellet. Two to four mL of Pronase solution (CalBiochem, Cat. #53702; 0.5 mg/mL in PBS) was added to the cells to resuspend the cell pellet gently. The enzyme treatment was allowed to proceed for no more than two minutes and the reaction stopped by the addition of 3-5 mL of FBS. Enough ECF solution was added to bring the total volume to 40 mL and the mixture was centrifuged at 800×g (2000 rpm) for 5-7 minutes. The supernatant was removed and the cell pellet gently resuspended with a small volume of ECF solution, followed by enough ECF solution to make a total volume of 40 mL. The cells were mixed well and counted, then centrifuged at 800×g (2000 rpm) for 5-7 minutes. The supernatant was removed and the cells resuspended in a small volume of ECF solution. Enough additional ECF solution was added to adjust the concentration to $2 \times 10^6$ cells/mL.

The cells were then placed in an Electro-Cell-Fusion (ECF) generator (Model ECM2001, Genetronic, Inc., San Diego, Calif.) and fused according to the manufacturer's instructions. After ECF, the cell suspensions were carefully removed from the fusion chamber under sterile conditions and transferred into a sterile tube containing the same volume of Hybridoma Medium in DMEM. The cells were incubated for 15-30 minutes at 37° C., then centrifuged at 400×g (1000 rpm) for five minutes. The cells were gently resuspended in a small volume of ½ HA medium (1 bottle of 50× HA from Sigma, Cat. #A9666 and 1 liter of Hybridoma Medium) and the volume adjusted appropriately with more ½ medium (based on $5 \times 10^6$ B cells per 96-well plate and 200 μL per well). The cells were mixed well and pipetted into 96-well plates and allowed to grow. On day 7 or 10, one-half the medium was removed, and the cells re-fed with ½ medium.

Selection of candidate antibodies for ELISA. After 14 days of culture, hybridoma supernatants were screened for MCP-1-specific monoclonal antibodies. The ELISA plates (Fisher, Cat. No. 12-565-136) were coated with 50 μl/well of MCP-1 (2 μg/mL) in Coating Buffer (0.1 M Carbonate Buffer, pH 9.6, NaHCO$_3$ 8.4 g/L), then incubated at 4° C. overnight. After incubation, the plates were washed with Washing Buffer (0.05% Tween 20 in PBS) three times. 200 μl/well Blocking Buffer (0.5% BSA, 0.1% Tween 20, 0.01% Thimerosal in 1×PBS) were added and the plates incubated at room temperature for 1 hour. After incubation, the plates were washed with Washing Buffer three times. 50 μL/well of hybridoma supernatants, and positive and negative controls were added and the plates incubated at room temperature for 2 hours.

The positive control used throughout was XMG2 MCP-1 Group 1, footpad N160-7 and the negative control was XMG2 KLH Group 1, footpad L627-6. After incubation, the plates were washed three times with Washing Buffer. 100 μL/well of detection antibody goat anti-hulgGfc-HRP (Caltag, Cat. #H10507), (and goat anti-hIgkappa-HRP (Southern Biotechnology, Cat. #2060-05) and goat anti-hIglambda (Southern Biotechnology, Cat. #2070-05) in secondary screening) were added and the plates incubated at room temperature for 1 hour. In the secondary screen, three sets of samples (positives in first screening) were screened, one set for hIgG detection, one set for hKappa detection, and one set for hlambda detection. After incubation, the plates were washed three times with Washing Buffer. 100 μL/well of TMB (BioFX Lab. Cat. #TMSK-0100-01) were added and the plates allowed to develop for about 10 minutes (until negative control wells barely started to show color), then 50 μL/well stop solution (TMB Stop Solution (BioFX Lab. Cat. #STPR-0100-01) were added and the plates read on an ELISA plate reader at wavelength 450 nm. The OD readings from the positive wells are presented in Table 9.

TABLE 9

| mAb Clone | ELISA OD-MCP-1 | IC50 Ca++ Flux (μg/mL) | IC50 Chemotaxis (μg/mL) | Affinity (pMol) | Cross-Reactivity |
|---|---|---|---|---|---|
| 1.1.1 | 3.638 | 0.24 + 0.034 | 0.27 + 0.034 | 2.7 | |
| 1.2.1 | 3.466 | 0.18 + 0.008 | 0.24 + 0.034 | 77 | |
| 1.3.1 | 4 | 0.12 + 0.012 | 0.24 + 0.059 | 55 | |
| 1.4.1 | 4 | 0.11 + 0.005 | 0.51 + 0.035 | 96 | |
| 1.5.1 | 0.51 | 0.21 + 0.027 | 0.34 + 0.054 | 4.2 | |
| 1.6.1 | 3.918 | 1 + 0.24 | 12 + 5.8 | 228 | |
| 1.7.1 | 3.521 | 0.11 + 0.013 | 0.35 + 0.064 | 4.9 | |
| 1.8.1 | 3.472 | 0.26 + 0.076 | 0.88 + 0.21 | 4 | |
| 1.9.1 | 3.6561 | 1.2 + 0.38 | 35 + 54 | 96 | |

TABLE 9-continued

| mAb Clone | ELISA OD-MCP-1 | IC50 Ca++ Flux (µg/mL) | IC50 Chemotaxis (µg/mL) | Affinity (pMol) | Cross-Reactivity |
|---|---|---|---|---|---|
| 1.10.1 | 3.845 | 0.18 + 0.11 | 1.2 + 0.55 | 9.6 | |
| 1.11.1 | 3.905 | 0.098 + 0.008 | 0.81 + 0.24 | 4.2 | |
| 1.12.1 | 4 | 0.13 + 0.02 | 0.35 + 0.039 | 13 | |
| 1.13.1 | 4 | 0.11 + 0.015 | 0.5 + 0.091 | 71 | |
| 1.14.1 | 2.064 | 0.41 + 0.1 | 0.58 + 0.18 | 6 | |
| 1.18.1 | 0.9984 | 0.18 + 0.055 | 0.29 + 0.07 | 3.8 | |
| 2.3.1 | 3.876 | 0.14 + 0.021 | 0.58 + 0.085 | 96 | |
| 2.4.1 | 3.892 | 0.26 + 0.18 | >5 | 14 | mouse JE |
| 3.2 | 3.96 | | | ND | MCP-2, MCP-3, eotaxin |
| 3.4.1 | 3.86 | 0.24 + 0.019 | 0.51 + 0.1 | 45 | |
| 3.5.1 | 3.765 | 0.58 + 0.29 | 3.1 + 1.1 | 100 | |
| 3.6.1 | 3.593 | 0.17 + 0.04 | 0.52 + 0.18 | 15 | |
| 3.7.1 | 4 | 0.094 + 0.023 | 0.98 + 0.019 | 4.8 | |
| 3.8.1 | 3.603 | 0.27 + 0.028 | 0.7 + 0.19 | 3.4 | |
| 3.10.1 | 3.634 | 0.3 + 0.1 | 0.25 + 0.1 | 90 | MCP-2, MCP-3, eotaxin |
| 3.11.1 | 4 | 0.092 + 0.023 | 0.33 + 0.47 | 3.3 | MCP-2, MCP-3, MCP-4 eotaxin |
| 3.14.1 | 4 | 1.3 + 0.3 | 1.4 + 0.47 | ND | |
| 3.15.1 | 4 | 0.12 + 0.034 | 0.89 + 0.1 | 3.4 | |
| 3.16.1 | 3.921 | 0.16 + 0.08 | 0.4 + 0.081 | 25 | |
| 4.5.1 | 3.38 | 0.27 + 0.074 | 0.75 + 0.18 | 61 | |
| 4.6.1 | 3.51 | 0.31 + 0.06 | 0.4 + 0.056 | 330 | |
| 4.7.1 | 3.843 | 0.39 + 0.063 | 0.45 + 0.11 | 280 | |
| 4.8.1 | 4 | 0.22 + 0.77 | 0.29 + 0.032 | 102 | |
| 4.9.1 | 3.415 | 0.083 + .0094 | 0.21 + 0.035 | ND | |
| 5.1 | 4 | 3.5 + 2.1 | 1.3 + 1.2 | 1610 | |
| 5.2.1 | 3.714 | 2.5 + 0.66 | 2.1 + 1.7 | 319 | Rantes |
| 5.3.1 | 4 | 1.8 + 0.56 | 2.6 + 0.31 | 450 | |

ND = not done

Characterization of Anti-MCP-1 Antibodies for Biologic Activity.

Neutralization of MCP-1 bioactivity with anti-MCP-1 antibodies—FLIPR assay. DMSO and Pluronic Acid (20% DMSO solution) were added to a vial of Fluo-4 (Molecular Probes) to yield a final concentration of 5 mM Fluo4. THP-1 cells were resuspended in prewarmed (37° C.) loading buffer at 3×10e6/mL and 1 µL of Fluo-4 dye per ml of cells was added to give a final concentration of dye at 5 µM. The cells were incubated in the dark at 37° C. for 45-50 minutes. After incubation, the cells were centrifuged at 1000 RPM for 5-10 min. The cells were resuspended in loading buffer and the centrifugation was repeated. The cells were resuspended at 1.667 e6/mL. At a concentration of 200,000 cells/well, the cells were added to a 96-well plate and centrifuged gently. After taking a baseline reading, a second reading was taken upon subsequent addition of 3.5 nM MCP-1 in the presence or absence of varying concentrations of anti-MCP-1 antibodies. Addition of MCP-1 to the THP-1 cells resulted in a rise of intracellular calcium leading to enhancement of fluorescence intensity of Fluo-4 dye. Upon addition of increasing concentrations of neutralizing antibody, the fluorescent dye intensity within the cells was decreased, thus indicating that the antibody tested was neutralizing. The concentration of antibody that yielded a 50% decrease in MCP-1 induced fluorescence intensity is presented in Table 9.

Neutralization of MCP-1-induced cell migration. An automated 96-well chemotaxis assay was developed using THP-1 cells and a Beckman Biomek F/X robotic system. Using a specially designed 96-well plate, a framed filter with the filter membrane bonded to a rigid frame, the chemotaxis assay was run in a NeuroProbe 96-well disposable microplate with a well volume of either 30 µl or 300 µl and pore diameter ranging from 2-14 µm. The Neuroprobe 96-well plate provides bottom wells for placing the MCP-1 chemoattractant and other reagents such as anti-MCP-1 antibodies in cell-migration assays. No top wells were required because the framed filter was coated with a hydrophobic mask that confines each cell-suspension sample to its site on top of the filter.

The optimum conditions for this assay were: 100,000 cells/well with 90 min incubation at 37° C. Suspensions of THP-1 cells that had bee pre-loaded with dye from Molecular Probes were pipetted directly onto the sites on the upper side of the filter and incubated at 37° C. for 1-2 hours. After incubation, the cells that had migrated to the bottom of the filter and into the microplate were counted by placing the microplate into an FMAT purchased from Applied Biosystems.

MCP-1 induced cell migration for THP-1 cells and the maximal cell migration was reached at 1 nM with a signal to noise ratio of 10-15 fold. Using either hybridoma supernatants or fresh hybridoma media, MCP-1-dependent migration was detected. The variability of the assay was minimal (C.V~15). The number of cells migrating to the bottom of the filters was decreased in a dose dependent manner when antibodies to MCP-1 were included with the chemoattractant.

Determination of anti-MCP-1 antibody affinity using Biacore analysis. The antibody/MCP-1 interaction analysis was performed at 25° C. using two CM5 chips docked in Biacore 3000 optical biosensors. Individual flow cells on each chip were activated with a 7-minute injection of NHS/EDC, carbohydrazide was coupled through the NHS ester using a 7-minute injection, and the residual activated groups were blocked with a 7-minute injection of ethanolamine. The monosaccharide residues of each antibody were oxidized using 1 mM sodium metaperiodate in 100 mM sodium acetate, pH 5.5 at 4° C. for 30 minutes. The oxidized antibody was desalted into 10 mM sodium acetate, pH 5.0, to couple the antibody to the carbohydrazide-modified surface. The mAb surfaces were stabilized by reducing the hydrazone bond with 0.1 M sodium cyanoborohydride. The antigen/antibody interaction was tested by injecting 0, 0.049, 0.15, 0.4, 1.3, 4 and 12 nM of MCP-1 (Peprotech, N.J.) in running buffer (10 mM HEPES, 150 mM NaCl, 0.005% surfactant, 200 µg/ml BSA, pH 7.4). The surfaces were regenerated with a 12-second pulse of 15 mM $H_3PO_4$. The antigen/antibody interaction was tested by injecting duplicate antigen samples diluted in running buffer (10 mM HEPES, 150 mM NaCl, 0.005% surfactant, 200 µg/mL BSA, pH 7.4), in a 300-fold concentration range. The surfaces were regenerated with a 12-second pulse of 15 mM $H_3PO_4$. To determine the kinetics of each interaction, the data sets were fit globally to a 1:1 interaction model that included a parameter for mass transport. The calculated affinities of interaction are reported in Table 9.

Determining cross-reactivity of anti-MCP-1 antibodies with other chemokines. ELISA plates (Fisher Cat. No. 12-565-136) were coated with 50 µl/well of MCP-1, MCP-2, MCP-3, MCP-4, RANTES, GRO-alpha, MIP-1 alpha, eotaxin, rat MCP-1 and mouse JE (2 µg/ml) in coating buffer (0.1 M carbonate buffer, pH 9.6, $NaHCO_3$ 8.4 g/L, then incubated at 4° C. overnight. After incubation, the plates were washed with washing buffer (0.05% Tween 20 in PBS) three times. 200 µL/well blocking buffer (0.5% BSA, 0.1% Tween 20, 0.01% Thimerosal in 1×PBS) were added and the plates incubated at room temperature for 1 hour. After incubation, the plates were washed with washing buffer three times. 50 µL/well of hybridoma supernatants, and positive and negative controls (positive control was anti-MCP-1 antibody purchased from R&D Sciences, and negative control was an antibody to Keyhole Limpet Hemocyanin produced at Abgenix) were added and the plates incubated at room temperature for 2 hours. After incubation, the plates were washed three times with washing buffer. 100 μL/well of detection antibody goat anti-huIgGfc-HRP (Caltag, Cat. #H10507), (goat anti-hIgkappa-HRP (Southern Biotechnology, Cat. #2060-05) and goat anti-hIglambda (Southern Biotechnology, Cat. #2070-05) in secondary screening) were added and the plates incubated at room temperature for 1 hour. After incubation, the plates were washed three times with washing buffer and 100 μL/well of TMB (BioFX Lab. Cat. #TMSK-0100-01) was added and the plates allowed to develop for about 10 minutes. At this time, 50 μL/well stop solution (TMB Stop Solution (BioFX Lab. Cat. #STPR-0100-01) were added and the plates read on an ELISA plate reader at wavelength 450 nm. The results presented in Table 10 demonstrate that several of the anti-MCP-1 antibodies cross-reacted with related chemokines.

TABLE 10

| mAb | rmJE/MCP-1 2 μg/mL | rat MCP-1 1 μg/mL | rhMCP-2 2 μg/mL | rhMCP-3 2 μg/mL | rhMCP-4 2 μg/mL |
|---|---|---|---|---|---|
| 1.1.1 | 0.045 | 0.051 | 0.051 | 0.064 | 0.052 |
| 1.2.1 | 0.041 | 0.044 | 0.056 | 0.048 | 0.055 |
| 1.3.1 | 0.046 | 0.048 | 0.065 | 0.052 | 0.048 |
| 1.4.1 | 0.042 | 0.05 | 0.046 | 0.049 | 0.045 |
| 1.5.1 | 0.043 | 0.045 | 0.047 | 0.069 | 0.05 |
| 1.6.1 | 0.042 | 0.062 | 0.042 | 0.046 | 0.044 |
| 1.7.1 | 0.041 | 0.042 | 0.044 | 0.053 | 0.041 |
| 1.8.1 | 0.045 | 0.049 | 0.048 | 0.054 | 0.046 |
| 1.9.1 | 0.053 | 0.065 | 0.04 | 0.044 | 0.042 |
| 1.10.1 | 0.041 | 0.059 | 0.04 | 0.047 | 0.052 |
| 1.11.1 | 0.041 | 0.052 | 0.041 | 0.043 | 0.043 |
| 1.12.1 | 0.042 | 0.062 | 0.042 | 0.046 | 0.044 |
| 1.13.1 | 0.043 | 0.06 | 0.046 | 0.047 | 0.045 |
| 1.14.1 | 0.042 | 0.062 | 0.042 | 0.046 | 0.044 |
| 1.18.1 | 0.044 | 0.058 | 0.04 | 0.045 | 0.045 |
| 2.3.1 | 0.054 | 0.058 | 0.052 | 0.059 | 0.064 |
| 2.4.1 | 0.129 | 0.077 | 0.045 | 0.066 | 0.06 |
| 3.4.1 | 0.044 | 0.053 | 0.042 | 0.05 | 0.047 |
| 3.5.1 | 0.042 | 0.053 | 0.042 | 0.045 | 0.044 |
| 3.6.1 | 0.047 | 0.046 | 0.052 | 0.045 | 0.048 |
| 3.7.1 | 0.046 | 0.048 | 0.043 | 0.048 | 0.048 |
| 3.8 | 0.042 | 0.062 | 0.042 | 0.046 | 0.044 |
| 3.10.1 | 0.054 | 0.045 | 0.845 | 0.167 | 0.042 |
| 3.11.1 | 0.063 | 0.057 | 0.336 | 1.317 | 0.981 |
| 3.14.1 | 0.044 | 0.046 | 0.045 | 0.05 | 0.045 |
| 3.15.1 | 0.041 | 0.05 | 0.043 | 0.046 | 0.051 |
| 3.16.1 | 0.042 | 0.046 | 0.049 | 0.043 | 0.043 |
| 4.5.1 | 0.049 | 0.055 | 0.042 | 0.046 | 0.046 |
| 4.6.1 | 0.049 | 0.05 | 0.047 | 0.05 | 0.047 |
| 4.7.1 | 0.042 | 0.062 | 0.042 | 0.046 | 0.044 |
| 4.8.1 | 0.042 | 0.091 | 0.041 | 0.043 | 0.039 |
| 4.9.1 | 0.05 | 0.05 | 0.046 | 0.049 | 0.05 |
| 5.1 | 0.044 | 0.054 | 0.051 | 0.05 | 0.043 |
| 5.2.1 | 0.04 | 0.054 | 0.041 | 0.048 | 0.041 |
| 5.3.1 | 0.05 | 0.047 | 0.043 | 0.045 | 0.043 |
| 3.2 (neat) | 0.059 | 0.07 | 0.535 | 0.449 | 0.041 |
| nc | 0.042 | 0.134 | 0.045 | 0.084 | 0.074 |
| pc | 0.263 | ND | ND | 1.084 | 0.215 |

| mAb | hGRO/MGSA 1 μg/mL | hMIP-1-alpha 1 μg/mL | hRANTES 1 μg/mL | hEotaxin 1 μg/mL | Positive control hMCP-1(MCAF) 2 μg/mL |
|---|---|---|---|---|---|
| 1.1.1 | 0.047 | 0.044 | 0.044 | 0.042 | 0.944 |
| 1.2.1 | 0.044 | 0.04 | 0.04 | 0.044 | 1.159 |
| 1.3.1 | 0.051 | 0.049 | 0.049 | 0.046 | 1.158 |
| 1.4.1 | 0.044 | 0.041 | 0.046 | 0.043 | 0.738 |
| 1.5.1 | 0.048 | 0.041 | 0.049 | 0.043 | 1.178 |
| 1.6.1 | 0.046 | 0.046 | 0.046 | 0.042 | 0.375 |
| 1.7.1 | 0.041 | 0.04 | 0.039 | 0.04 | 1.17 |
| 1.8.1 | 0.06 | 0.045 | 0.045 | 0.047 | 1.159 |
| 1.9.1 | 0.043 | 0.044 | 0.042 | 0.042 | 0.446 |
| 1.10.1 | 0.043 | 0.043 | 0.042 | 0.05 | 1.259 |
| 1.11.1 | 0.042 | 0.042 | 0.042 | 0.049 | 1.336 |
| 1.12.1 | 0.046 | 0.046 | 0.046 | 0.044 | 0.933 |
| 1.13.1 | 0.046 | 0.042 | 0.046 | 0.044 | 1.16 |
| 1.14.1 | 0.046 | 0.046 | 0.046 | 0.042 | 1.129 |
| 1.18.1 | 0.049 | 0.043 | 0.04 | 0.043 | 1.228 |
| 2.3.1 | 0.062 | 0.067 | 0.055 | 0.045 | 0.087 |
| 2.4.1 | 0.048 | 0.061 | 0.046 | 0.084 | 0.462 |
| 3.4.1 | 0.065 | 0.055 | 0.046 | 0.048 | 1.153 |
| 3.5.1 | 0.048 | 0.047 | 0.044 | 0.043 | 0.194 |
| 3.6.1 | 0.047 | 0.047 | 0.043 | 0.043 | 0.342 |
| 3.7.1 | 0.045 | 0.049 | 0.067 | 0.043 | 1.276 |
| 3.8 | 0.046 | 0.046 | 0.046 | 0.042 | 0.275 |
| 3.10.1 | 0.042 | 0.043 | 0.04 | 0.306 | 0.71 |
| 3.11.1 | 0.054 | 0.053 | 0.064 | 0.339 | 0.803 |
| 3.14.1 | 0.046 | 0.046 | 0.045 | 0.043 | 0.549 |
| 3.15.1 | 0.044 | 0.045 | 0.049 | 0.045 | 0.948 |
| 3.16.1 | 0.043 | 0.043 | 0.042 | 0.043 | 0.633 |
| 4.5.1 | 0.045 | 0.046 | 0.049 | 0.041 | 0.957 |
| 4.6.1 | 0.046 | 0.055 | 0.053 | 0.049 | 0.686 |
| 4.7.1 | 0.046 | 0.046 | 0.046 | 0.042 | 0.744 |
| 4.8.1 | 0.042 | 0.041 | 0.044 | 0.043 | 1.136 |
| 4.9.1 | 0.043 | 0.049 | 0.057 | 0.045 | 0.822 |
| 5.1 | 0.044 | 0.043 | 0.043 | 0.042 | 0.521 |
| 5.2.1 | 0.045 | 0.043 | 0.262 | 0.043 | 0.663 |
| 5.3.1 | 0.045 | 0.042 | 0.045 | 0.042 | 0.272 |
| 3.2 (neat) | 0.042 | 0.041 | 0.043 | 0.194 | 0.235 |
| nc | 0.357 | 0.065 | 0.072 | 0.063 | 0.042 |
| pc | 1.075 | 0.794 | 1.219 | 0.221 | 0.281 |

Figure 2:
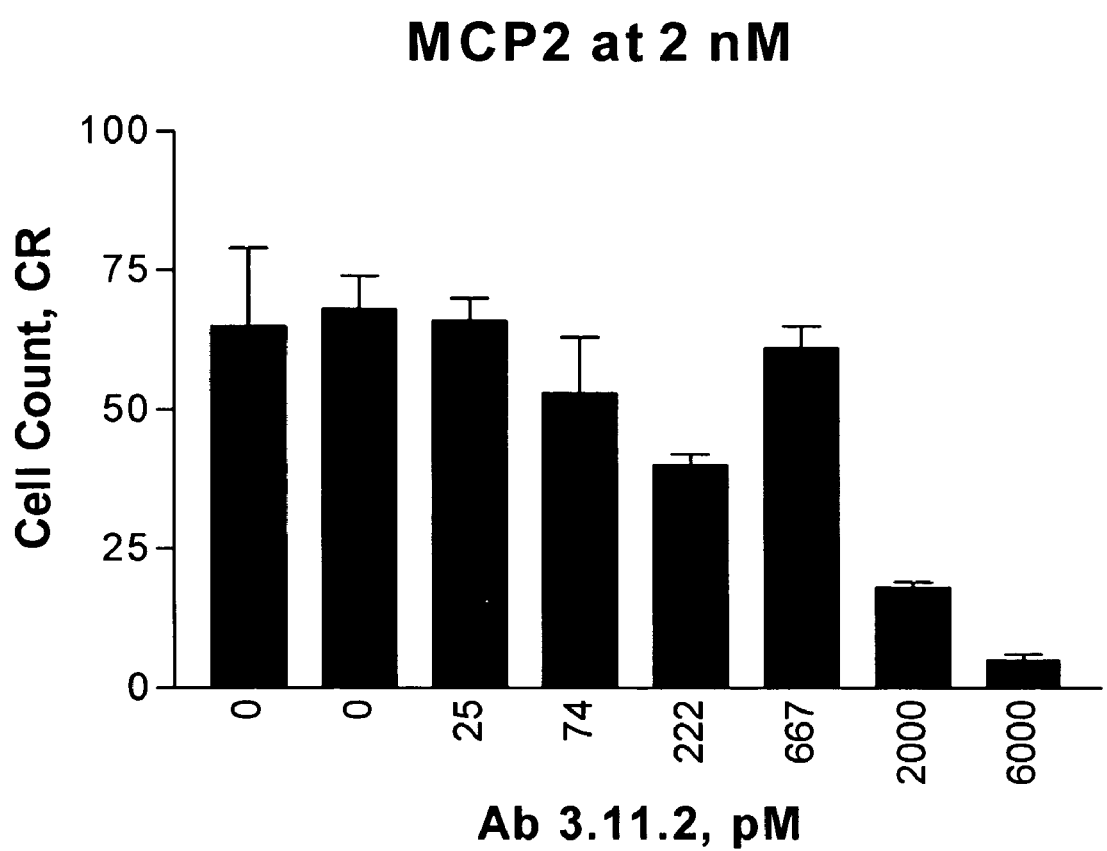
FIG. 2 shows inhibition by antibody 3.11.2 in a dose-dependent manner of the migration ability of THP-1 cells in response to MCP-2.
Figure 3:
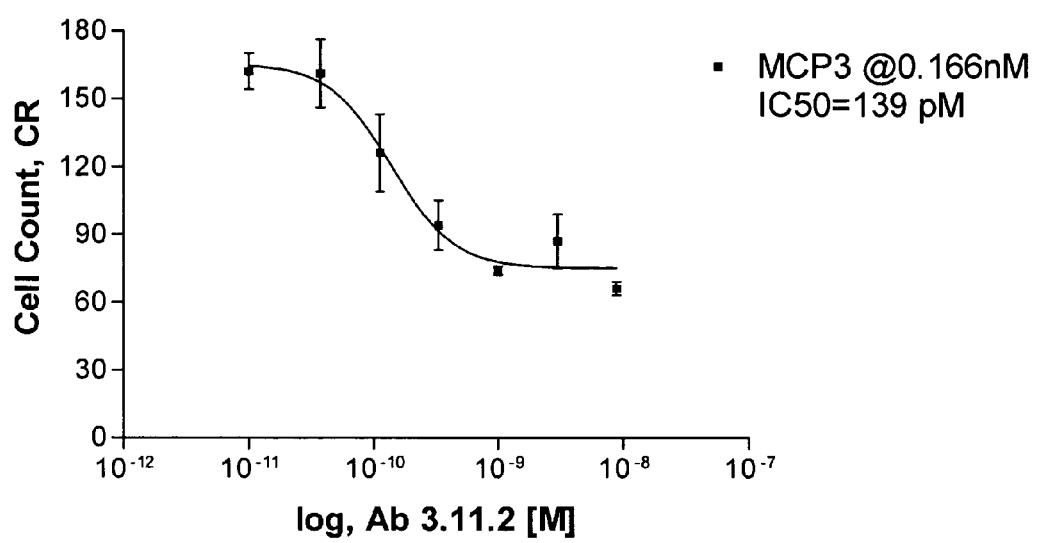
FIG. 3 shows inhibition by antibody 3.11.2 in a dose-dependent manner of the migration ability of THP-1 cells in response to MCP-3.

Coat: Ag @ 2 μg/mL or 1 μg/mL; O/N
Ab: MCP-1 purified clones 1:50
pc: 1 μg/mL; nc: D39.2 IL8 @1 μg/mL
Detect samples with gxhG-Fc HRP 1:2K; controls with mix xmIgG1, 2a, 2b, 3 1:1K To determine whether anti-MCP-1 antibody 3.11.2 could block the function of other MCP family members, migration assays as described above were performed. First, the ability of THP-1 monocytes to migrate in response to MCP-1, MCP-2, MCP-3, and MCP-4 was determined. MCP-1, -2 and -3 effectively induced migration of THP-1 cells, but MCP-4 was not active in this assay (see FIG. 1). When antibody 3.11.2 was added to the bottom side of the well at varying concentrations, the ability of the THP-1 cells to migrate in response to MCP-2 and MCP-3 was inhibited in a dose dependent manner (FIGS. 2 and 3).

Example 3

Epitope Mapping of MCP-1

Monocyte chemo-attractant protein-1 (MCP-1) is a member of the beta chemokine family that acts through a specific seven-transmembrane receptor to recruit monocytes, basophils, and T lymphocytes to the site of inflammation. The antigen, a 76-amino-acid residue is nonglycosylated and has a predicted molecular mass of 8.7 kD. Human MCP-1, expressed in E. coli, was purchased from R&D #279MC/CF. Monkey MCP was expressed in 293F cells, and three monkey MCP-1 variants were used to analyze how defined amino-acid replacements affect binding affinity for each individual mAb.

Sequence analysis showed that the antibodies fell into five classes. The largest class included 28 antibodies highly related by their use of VH1-24, of which, 24 also use Vk gene B3. A class comprised of three antibodies use the VH6-1 gene, two of which use Vk B3. Three other classes are represented by one antibody each, using VH1-2, VH3-33 and VH4-31, of which two of these mAbs use the Vk08 gene. It should be noted that antibody names beginning with 1, 2, 3, or 4 represent different hybridoma fusions from independent cohorts of XenoMouse® mice. Therefore, these monoclonal antibodies arose from independent lineages of B cells maturing during independent primary and secondary immune responses in XenoMouse® mice. Because of their independence, the similarity in nucleotide and amino acid sequence of the antibody VH and Vk genes likely represents a convergent evolution and selection for a similar variable region structure that can bind to and potently neutralize MCP-1 (see Table 11).

TABLE 11

| Samples | Iso-type | VH | DH | JH | VK | JK | Epitope |
|---|---|---|---|---|---|---|---|
| 1.1.1 | γ2/κ | VH1-24 | D3-3(17) | JH4b | VK-B3 | JK1 | Conf. |
| 1.2.1 | γ2/κ | VH1-24 | D3-3(17) | JH4b | VK-L5 | JK1 | Linear |
| 1.3.1 | γ2/κ | VH1-24 | D3-3(15) | JH4b | VK-B3 | JK1 | Conf. |
| 1.4.1 | γ2/κ | VH6-1 | D1-26 | JH4b | VK-A2 | JH4 | linear |
| 1.5.1 | γ2/κ | VH1-24 | D3-3(17) | JH4b | VK-B3 | JK1 | Linear |
| 1.6.1 | γ2/κ | VH1-24 | D1-26(18) | JH3b | VK-A10 | JK4 | Conf. |
| 1.7.1 | γ2/κ | VH1-24 | D3-3(17) | JH4b | VK-B3 | JK1 | Conf. |
| 1.8.1 | γ2/κ | VH1-24 | D3-3(17) | JH4b | VK-B3 | JK1 | Linear |
| 1.9.1 | γ2/κ | VH1-24 | D5-12(13) | JH4b | VK-B3 | JK1 | no binding |
| 1.10.1 | γ2/κ | VH1-24 | D3-3(17) | JH4b | VK-B3 | JK1 | Linear |
| 1.11.1 | γ2/κ | VH1-24 | D3-3 | JH4B | VK-B3 | JK1 | Linear |
| 1.12.1 | γ2/κ | VH1-24 | D3-3(16) | JH4b | VK-B3 | JK1 | Conf. |
| 1.13.1 | γ2/κ | VH1-24 | D3-3(17) | JH4b | VK-B3 | JK1 | Linear |
| 1.14.1 | γ2/κ | VH6-1 | D1-26 | JH6b | VK-B3 | JK1 | Linear |
| 1.18.1 | γ2/κ | VH1-24 | D3-3(15) | JH4b | VK-B3 | JK4 | Linear |
| 2.3.1 | γ4/κ | VH1-24 | D3-3(16) | JH4b | VK-B3 | JK2 | no binding |
| 3.2 | γ2/κ | VH1-24 | D3-3(17) | JH4b | VK-L16 | JK4 | Conf. |
| 2.4.1 | γ4/κ | VH1-2 | D6-13(15) | JH4b | VK-08 | JK5 | no binding |
| 3.4.1 | γ2/κ | VH1-24 | D3-3(16) | JH4b | VK-B3 | JK1 | Linear |
| 3.5.1 | γ4/κ | VH1-24 | D3-3(17) | JH4b | VK-B3 | JK1 | no binding |
| 3.6.1 | γ4/κ | VH1-24 | D3-3(17) | JH4b | VK-B3 | JK1 | no binding |
| 3.7.1 | γ2/κ | VH1-24 | D3-3(16) | JH4b | VK-B3 | JK1 | Conf. |
| 3.8 | γ4/κ | VH1-24 | D3-3 | JH4B | VK-B3 | JK1 | no binding |
| 3.10.1 | γ4/κ | VH1-24 | D3-9(12) | JH6b | VK-A30 | JK3 | Conf. |
| 3.11.1 | γ4/κ | VH4-31 | D2-21(10) | JH3b | VK-08 | JK2 | Conf. |
| 3.14.1 | γ4/κ | VH6-1 | D1-26 | JH6B | VK-B3 | JK1 | Conf. |
| 3.15.1 | γ4/κ | VH1-24 | D5-12(13) | JH4b | VK-B3 | JK1 | Linear |
| 3.16.1 | γ4/κ | VH1-24 | D3-3(17) | JH4b | VK-B3 | JK1 | Conf. |
| 4.5.1 | γ2/κ | VH1-24 | D3-3(16) | JH4b | VK-B3 | JK1 | Conf. |
| 4.6.1 | γ2/κ | VH1-24 | D3-3 | JH3B | VK-B3 | JK1 | ND |
| 4.7.1 | γ2/κ | VH1-24 | D3-3(16) | JH4b | VK-B3 | JK1 | Conf. |
| 4.8.1 | γ2/κ | VH1-24 | D3-3 | JH4b | VK-B3 | JK1 | Conf. |
| 4.9.1 | γ2/κ | ND | ND | ND | ND | ND | Conf. |
| 5.1 | γ2/λ | VH3-33 | D6-6(15) | JH6B | V1-22 | JK2 | ND |
| 5.3.1 | γ2/κ | VH1-24 | D5-12(13) | JH4b | VK-B3 | JK1 | no binding |

Conf. = conformational
ND = Not Done
No binding = No binding on western blot.

Whether each antibody bound to a linear or conformational epitope was determined by Western blot analysis. To determine whether disruption of the intramolecular bonds by a reducing agent changed the reactivity of selected anti-MCP-1 antibodies, purified MCP-1 was loaded on SDS/PAGE (4-20% gel) under non-reducing (NR) or reducing (R) conditions. SDS/PAGE was performed by the method of Laemmli, using a mini-gel system. Separated proteins were transferred onto nitrocellulose membrane. Membranes were blocked using PBS containing 5% (w/v) non-fat dried milk for at least 1 hour before developing, and probed for 1 hour with each antibody. Anti-MCP-1 antibodies were detected using HRP-conjugated goat anti-human immunoglobulins (1:8,000 dilution; Sigma Catalog No. A-8667). Membranes were developed by using enhanced Chemiluminescence (ECL®; Amersham Bioscience) according to the manufacturer's instructions.

Antibody-MCP-1 complexes were analyzed by three methods: (1) Surface Enhanced Laser Desorption Ionization (SELDI) (Protein chip technology) for linear and conformational epitopes; (2) Site Directed Mutagensis for linear and conformational epitopes; and (3) SPOTs Peptide Array for linear epitopes. SELDI is a recently developed method for accurate, rapid and sensitive determination of the molecular weights of peptides and proteins. Linear and conformational epitopes were mapped based on the mass of the bound fragment to immobilized antibody by SELDI protein chip technology. Mapping of linear epitopes by SELDI was carried out in three steps. In the first step, MCP-1 was digested by highly specific proteolytic enzymes to generate sets of peptide fragments. In the second step, peptide fragments containing the linear epitopes were selected by their specific binding to the immobilized antibody on the protein chip. In this step, peptides that contain the epitope form complexes with the antibody, while other peptides that do not bind the antibody were removed by stringency wash. In the final step, the identity of the antibody-binding peptide was determined by its molecular weight by SELDI and the known digestion sites of the specific protease.

Antibodies 1.4.1, 1.8.1, 1.14.1, 1.18.1 reacted equally with native and denatured MCP-1 on the Western blot, indicating that these have a linear epitope. Their epitope was mapped by SELDI. The experiments were carried out by carboxymethylation of MCP-1 antigen to prevent the formation of disulfide bonds between cysteine residues in the protein. Methylated MCP-1 was digested with Glu-C, an endoproteinase that specifically cleaves peptide bonds on the carboxy-terminal side of glutamic acid (E) residues. mAbs were covalently coupled to the Protein chip array, PS20. The chip surface was blocked with 1M ethanolamine and washed with PBS, 0.5% Triton. Glu-C fragments of methylated MCP-1 antigen were bound to the immobilized antibody. Unbound fragments were washed off with detergent (PBS, 0.1% Tween). Bound Glu-C fragments (epitope) were analyzed and identified by SELDI based on their mass. Table 12 summarizes the expected mass of each peptide generated from complete digest of methylated MCP-1 with Glu-C. MCP-1 was completely digested into three fragments. The theoretical pI was: 9.39/Mw (average mass): 8685.03/Mw (monoisotopic mass): 8679.44. After the wash, the fragment with the mass 4635, corresponding to the residues 1-39, remained bound to the antibody, indicating that the epitope of all these antibodies lies in the first 39 residues as same pattern was seen with each of these antibodies.

TABLE 12

| Mass | Position in SEQ ID NO: 149 | #MC | Artif. modification(s) | Peptide sequence |
|---|---|---|---|---|
| 4458.2591 | 1-39 | 0 | Cys_CM: 11, 12, 36 4632.2755 | QPDAINAPVTCCYNFTNRKI SVQRLASYRRITSSKCPKE (SEQ ID NO: 151) |
| 3041.4819 | 51-76 | 0 | Cys_CM: 52 3099.4873 | ICADPKQKWVQDSMDHLDKQ TQTPKT (SEQ ID NO: 152) |
| 1218.7456 | 40-50 | 0 | | AVIFKTIVAKE (SEQ ID NO: 153) |

The SELDI approach was also used to map conformational epitopes. In this case, the protein A covalently bound to PS2 Protein chip arrays (Ciphergen Biosystems) was used to capture the mAbs, and subsequently incubated with MCP-1. After removal of unbound material, the complexes were digested with high concentration of specific proteases. MCP-1 antibodies (1.7.2, 3.11.2 and 3.7.2) do not bind to the reduced, denatured antigen on Western blots, indicating that the epitope is likely to be conformational. Antibodies 1.7.2 and 3.7.2 were first covalently coupled to the PS20 chip. Native MCP-1 was bound to the antibody and then digested with an endoproteinase (Lys-C in one experiment and Asp-N in the other). Unbound fragments were washed off with PBS+, 0.2% Triton followed with PBS and HPLC water wash. The epitope was determined by SELDI and identified by the mass of the fragment. Both these antibodies 1.7.2 and 3.7.2 had a fragment of mass 5712 corresponding to the residues 3-53 (Table 13; Theoretical pI: 9.39/Mw (average mass): 8685.03/Mw (monoisotopic mass): 8679.44) bound to it after the wash, indicating that the epitope lies in the 3 to 53 amino acid residues of the native MCP-1 antigen.

TABLE 13

| Mass | Position in SEQ ID NO: 149 | #MC | Peptide sequence |
|---|---|---|---|
| 5720.0059 | 3-53 | 0 | DAINAPVTCCYNFTNRKISV QRLASYRRITSSKCPKEAVI FKTIVAKEICA (SEQ ID NO: 154) |
| 1046.5476 | 68-76 | 0 | DKQTQTPKT (SEQ ID NO: 155) |
| 1028.5523 | 54-61 | 0 | DPKQKWVQ (SEQ ID NO: 156) |

For mapping the epitope of the antibody 3.11.2, the size of the binding domain was minimized by using a different protease. Protein A (Calbiochem, 539202) was immobilized covalently to a PS20 chip. Residual binding sites were blocked with ethanolamine, pH 8.0. Antibody 3.11.2 was bound to protein A. The chip was washed with PBS and then with 50 mM Hepes, pH 7.5. MCP-1 antigen was bound to the antibody. Unbound antigen was removed by washing with 0.1% Tween in PBS, followed by 50 mM Hepes, pH 7.5, and 100 mM ammonium bicarbonate. One chip digestion of MCP-1 was carried out with the endoproteinase, Lys-C. The chip was washed with 0.1% Triton in PBS to remove the unbound fragments. The bound fragment was analyzed based on its mass on SELDI. Only one peak of mass 1861.8 was bound to the antibody, representing a 15-amino-acid sequence, located at residues 20 to 35 (Table 14; Theoretical pI: 9.39/Mw (average mass): 8685.03/Mw (monoisotopic mass): 8679.44) of MCP-1, with the mass of 1865 and the sequence ISVQRLASYRRITSSK (Position 20-35 of SEQ ID NO.: 149) was identified as the most tightly bound fragment.

TABLE 14

| Mass | Position in SEQ ID NO: 149 | #MC | Peptide sequence |
|---|---|---|---|
| 2155.0059 | 1-19 | 0 | QPDAINAPVTCCYNFTNRK (SEQ ID NO: 158) |
| 1865.0715 | 20-35 | 0 | ISVQRLASYRRITSSK (SEQ ID NO: 150) |
| 1373.6154 | 59-69 | 0 | WVQDSMDHLDK (SEQ ID NO: 159) |
| 775.3654 | 50-56 | 0 | EICADPK (SEQ ID NO: 160) |
| 706.4134 | 39-44 | 0 | EAVIFK (SEQ ID NO: 161) |
| 702.3781 | 70-75 | 0 | QTQTPK (SEQ ID NO: 162) |

TABLE 14-continued

| Mass | Position in SEQ ID NO: 149 | #MC | Peptide sequence |
|---|---|---|---|
| 531.3500 | 45-49 | 0 | TIVAK (SEQ ID NO: 163) |

Mutagenesis of MCP-1. It was previously shown that two clusters of primarily basic residues (R24, K35, K38, K49, and Y13) appear to make the largest contributions to the interaction between MCP-1 and its receptor (Hemmerich et al., (1999) *Biochemistry* 38, 13013-13025). Binding data reveled that the N-terminal residues contribute little to binding activity and that two important residues are important for signaling activity of the MCP-1: K35 and R24. K35 is the most functionally important residue, because K35A mutation has a significant effect on binding and activity, as well as alanine mutants of R24 (Hemmerich et al., (1999) *Biochemistry* 38, 13013-13025). Arg24 is conserved across different species of MCP-1 as well as in human MCP-2-4, but varies widely in other CC chemokines and therefore maybe involved in receptor specificity. To identify individual residues within the first 39 residues of MCP-1, representing the Glu-C digest, that were important for antibody binding, three MCP-1 mutants were generated: the three basic residues, R24, K35, and K38, were mutated by site-directed mutagenesis and mutant protein was further analyzed for binding to all 36 neutralizing antibodies by ELISA. Arg24 was mutated to alanine (R24A) and glutamic acid (R24E). Lys35 and K38 were mutated to alanine (K35A, K38A respectively). All mutations were MCP-1 to MCP-1 antibodies was detected with HRP conjugated goat anti-human IgG (Fc specific, Caltag Catalog No. H10507). ELISA results have shown that changing K38 did not have any effect of binding activity of all 36 antibodies. Binding of all antibodies to R24E and R24A MCP-1 mutant antigen was completely abolished (see Table 15). However, the K35A mutation inhibited the binding of only six antibodies (1.6.1, 1.9.1, 3.6.1, 3.10.1). All of these antibodies appear to have a conformational epitope, binding to which is affected by mutation of either Arg24 or Lys35. These data suggest that these four antibodies recognize a conformational epitope different, but overlapping with, the other antibodies.

TABLE 15

| mAb | Epitope | Glu-C digest | Lys-C | Asp-N digest | Peptide | Residues | R24A/E | K35A |
|---|---|---|---|---|---|---|---|---|
| 1.1.1 | Conf. | ND | ND | ND | ND | ND | Inhibition | Inhibition |
| 1.2.1 | Linear | ND | ND | ND | 7__11 | 21-25 | Inhibition | No Inhibition |
| 1.3.1 | Conf. | ND | ND | ND | ND | ND | Inhibiton | No Inhibition |
| 1.4.1 | Linear | 1__39 | ND | ND | 7__11 | 21-25 | Inhibition | No Inhibition |
| 1.5.1 | Linear | ND | ND | ND | 7__11 | 21-25 | Inhibition | No Inhibition |
| 1.6.1 | Conf. | ND | ND | ND | ND | ND | Inhibition | Inhibition |
| 1.7.1 | Conf. | ND | ND | 3-53/5712 | ND | ND | Inhibition | No Inhibition |
| 1.8.1 | Linear | 1__39 | ND | ND | 7__11 | 21-25 | Inhibition | No Inhibition |
| 1.9.1 | no binding | ND | ND | ND | ND | ND | Inhibition | Inhibition |
| 1.10.1 | Linear | ND | ND | ND | 7__11 | 21-25 | Inhibition | No Inhibition |
| 1.11.1 | Linear | ND | ND | ND | ND | ND | Inhibition | No Inhibition |
| 1.12.1 | Conf. | ND | ND | ND | ND | ND | Inhibition | No Inhibition |
| 1.13.1 | Linear | ND | ND | ND | 7__11 | 21-25 | Inhibition | No Inhibition |
| 1.14.1 | Linear | 1__39 | ND | ND | 7__11 | 21-25 | Inhibition | No Inhibition |
| 1.18.1 | Linear | 1__39 | ND | ND | 7__11 | 21-25 | Inhibition | No Inhibition |
| 2.3.1 | no binding | ND | ND | ND | ND | ND | Inhibition | No Inhibition |
| 3.2 | Conf. | ND | ND | ND | ND | ND | Inhibition | No Inhibition |
| 2.4.1 | no binding | ND | ND | ND | ND | ND | Inhibition | No Inhibition |
| 3.4.1 | Linear | ND | ND | ND | ND | ND | Inhibition | No Inhibition |
| 3.5.1 | no binding | ND | ND | ND | ND | ND | Inhibition | No Inhibition |
| 3.6.1 | no binding | ND | ND | ND | ND | ND | Inhibition | Inhibition |
| 3.7.1 | Conf. | ND | ND | 3-53/5712 | ND | ND | Inhibition | No Inhibition |
| 3.8 | no binding | ND | ND | ND | ND | ND | Inhibition | Inhibition |
| 3.10.1 | Conf. | ND | ND | ND | ND | ND | Inhibition | Inhibition |
| 3.11.1 | Conf. | ND | 20-35(1864) | ND | ND | ND | Inhibition | No Inhibition |
| 3.14.1 | Conf. | ND | ND | ND | ND | ND | Inhibition | No Inhibition |
| 3.15.1 | Linear | ND | ND | ND | 7__11 | 21-25 | Inhibition | No Inhibition |
| 3.16.1 | Conf. | ND | ND | ND | ND | ND | Inhibition | No Inhibition |
| 4.5.1 | Conf. | ND | ND | ND | ND | ND | Inhibition | No Inhibition |
| 4.6.1 | ND | ND | ND | ND | ND | ND | Inhibition | No Inhibition |
| 4.7.1 | Conf. | ND | ND | ND | ND | ND | Inhibition | No Inhibition |
| 4.8.1 | Conf. | ND | ND | ND | ND | ND | Inhibition | No Inhibition |
| 5.1 | ND | ND | ND | ND | ND | ND | Inhibition | No Inhibition |
| 5.3.1 | no binding | ND | ND | ND | ND | ND | Inhibition | No Inhibition |

ND = Not Done
No binding = No binding on Western blot.

introduced in Monkey MCP-1 background. The monkey MCP-1 construct was generated recovered by performing RT-PCR on RNA isolated from monkey peripheral blood lymphocytes (cynomologus MCP-1PCR3.1 bidirectional). Protein sequence alignment between human and Monkey MCP-1 reveled 99% homology with two amino-acids changes at the C-terminal (positions 71 and 76). The C-terminal residues 59-76 are not involved in interaction with the receptor and did not affect the binding of all 36 antibodies.

ELISA assays were performed using supernatant from 293 cells transfected with different MCP-1 mutated constructs. ELISA plates were coated with anti-human MCP-1 goat IgG Polyclonal antibody (R&D catalog No. AF279NA) diluted to 1 μg/mL in ELISA plate coating buffer. Expression of mutant MCP-1 constructs in 293 cells was confirmed by detection with biotinylated goat anti-human MCP-1 (R&D catalog No. BAF279) followed by streptavidin HRP. Binding of mutant For those antibodies binding to a linear epitope, their binding to a peptide epitope was studied in detail using the SPOTs technology. SPOTs is a technology that allows the solid-phase synthesis of hundreds of peptides in a format suitable for the systematic analysis of antibody epitopes. The system is simple, extremely rapid and economic in its use of reagents. A custom-made peptide array was obtained from Sigma-Genosys (The Woodlands, Tex.). A series of 32, 13-mer peptides were synthesized spanning residues 1-76 of the MCP-1 sequence. Each consecutive peptide was offset by two amino acids from the previous one, yielding a nested, overlapping library. The membrane carrying the 32 peptides was probed with eight MCP-1 antibodies (1 μg/mL), detected with HRP-conjugated secondary antibody and followed by enhanced chemiluminescence (ECL). Reaction was observed with five consecutive peptide spots (7 to 11) corresponding to amino acids 21 to 25 of MCP-1. From these results, it appears that the core of the epitope for all of the tested MCP-1 antibodies binding to a linear epitope is SVQRL (21-25) (SEQ ID NO:157). The MCP-1 sequence is:

```
QPDAINAPVTCCYNFTNRKISVQRLASYRRITSS (SEQ ID NO: 149)
KCPKEAVIFKTIVAKEICADPKQKWVQDSMDHLD
KQTQTPKT
```

Eight antibodies, which recognized a linear epitope, reacted with the same SPOTs: 1.2.1, 1.4.1, 1.5.1, 1.8.1, 1.10.1, 1.13.1, 1.14.1, and 1.18.1.

Example 4

Affinity Determination of Cross-Reacting Antibodies by High-Resolution Biacore Analysis The interaction analysis was performed at 25° C. using two CM5 chips docked in Biacore 2000 optical biosensors. Individual flow cells on each chip were activated with a 7-minute injection of NHS/EDC, carbohydrazide was coupled through the NHS ester using a 7-minute injection, and the residual activated groups were blocked with a 7-minute injection of ethanolamine. The monosaccharide residues of mAb 3.11.2, diluted 1/50, were oxidized using 1 mM sodium metaperiodate in 100 mM sodium acetate, pH 5.5 at 4° C. for 30 minutes. The oxidized antibody was desalted into 10 mM sodium acetate, pH 5.0, to couple the antibody to the carbohydrazide-modified surface. A surface density of 250 RU mAb 3.11.2 was used to measure the reported interactions of MCP-1 and MCP-4, while a surface of 110 RU was used to measure the interactions of antigens MCP-2 and MCP-3 with mAb 3.11.2. The mAb surfaces were stabilized by reducing the hydrazone bond with 0.1 M sodium cyanoborohydride. The antigen/antibody interaction was tested by injecting duplicate antigen samples diluted in running buffer (10 mM HEPES, 150 mM NaCl, 0.005% surfactant, 200 μg/mL BSA, pH 7.4), in a 300-fold concentration range. The surfaces were regenerated with a 12-second pulse of 15 mM $H_3PO_4$.

To determine the kinetics of each interaction, the data sets were fit globally to a 1:1 interaction model that included a parameter for mass transport. The estimated rate constants and the calculated affinities of interaction for antibody 3.11.2 are reported in Table 16. The data for all the other antibodies are presented in Table 8.

TABLE 16

| Ag | $k_a$ (M$^{-1}$ s$^{-1}$) | $K_d$ (s$^{-1}$) | $K_D$ (pM) |
|---|---|---|---|
| MCP-1 | $3.0 \times 10^8$ | $1.0 \times 10^{-3}$ | 3.3 |
| MCP-2 | $2.6 \times 10^8$ | $1.2 \times 10^{-2}$ | 46 |
| MCP-3 | $1.5 \times 10^8$ | $7.4 \times 10^{-3}$ | 49 |
| MCP-4 | $1.5 \times 10^8$ | $5.5 \times 10^{-4}$ | 3.7 |

Example 5

Prevention of Angiogenesis with Antibodies to MCP-1

Angiogenesis was induced in a mouse model by admixing Matrigel with human bFGF (10 ng/mL), human VEGF165 (100 ng/mL) and 10 μg/mL heparin or MCP-1 (250 ng/mL) and MCP-3 (100 ng/mL). About 0.5 mL of the suspension was subcutaneously injected into the right flank of 6-8 week-old, athymic, female, nude mice. Five mice were used for each dose of MCP-1 and MCP-3. In addition, as a negative control, Matrigel alone (no growth factors) was included. The Matrigel implants solidified in situ and were left undisturbed for 7 days. At the end of 7 days, the mice were anesthetized, and the Matrigel plugs were removed carefully using microsurgical instruments. Gels were photographed under transillumination. One part of the plugs was processed for paraffin embedded sectioning. Sections were cut at two different levels and stained with H/E. Another part of the gel was snap frozen in liquid nitrogen and subjected to immunocytochemical staining with rat monoclonal antibody directed against mouse CD31 antigen conjugated with phycoerythrin. H+E stained slides were elevated for the formation of the distinct, endothelial lined vessels. Anti-CD31-PE stained slides were observed under Fluorescence microscope (red filter) attached to a Spot Camera. Images were captured digitally using Metamorph software program. Microvessel density was determined by the method published by Wild et al. (2000).

Both MCP-1 and MCP-3 were found to show equivalent angiogenesis as the well-characterized angiogenic factors VEGF and bFGF. In addition, angiogenesis induced by MCP-1 or MCP-3 in animals, and by inference in human tumors or diseased tissue, can be prevented by treating with antibodies to MCP-1 or an antibody such as 3.11.2, which neutralizes the activity of all MCP family members. Accordingly, one would inject the anti-MCP antibodies into animals at different doses ranging from approximately 0.1 to 0.5 mg per animal to obtain a dose-response relationship for treatment.

Example 6

MCP-1 Production by Tumor Cells

To determine whether tumor cells produced MCP-1 in cell culture, a panel of cell lines was examined for their ability to secrete MCP-1 into the culture medium. Cells were cultured in Dulbecco's Modified Eagles Medium (DMEM) containing 10% fetal bovine serum or an equivalent until confluent. The supernatant was removed and an aliquot tested for reactivity to MCP-1 using a commercially available ELISA kit from R & D Sciences. Table 17 shows a series of cancer cell lines that constitutively secrete MCP-1 and their respective MCP-1 levels as determined by ELISA.

TABLE 17

| | | Cell Line | MCP-1 (pg/mL) |
|---|---|---|---|
| 1 | Colon Carcinoma | COLO-205 | <10 |
| 2 | Colon Carcinoma | HCT-15 | 60 |
| 3 | Colon Carcinoma | HCT-116 | 122 |
| 4 | Colon Carcinoma | HT-29 | 102 |
| 5 | Cervical Cancer | HT-3 | 127 |
| 6 | Colon Carcinoma | SW707 | 31 |
| 7 | Colon Carcinoma | SW948 | 13 |
| 8 | Colon Carcinoma | KM-12 | 6 |
| 9 | Colon Carcinoma | HCC-2998 | 39 |
| 10 | Gastric Carcinoma | NCI-N87 | 37 |
| 11 | Gastric Carcinoma | NCI-SNU-1 4 | 0 |
| 12 | Gastric Carcinoma | NCI-SNU-5 | <10 |
| 13 | CNS Carcinoma | SF-268 | 94 |
| 14 | CNS Carcinoma | SF-295 | 223 |
| 15 | CNS Carcinoma | SF-593 | >2500 |
| 16 | CNS Carcinoma | SNB-19 | >2500 |
| 17 | CNS Carcinoma | SNB-75 | >2500 |
| 18 | CNS Carcinoma | U251 | >2500 |
| 63 | CNS | XF-498(Curg) | >2500 |
| 61 | Glioblastoma | SF-295(Curg) | >2500 |
| 21 | Medulloblastoma | TE 671 (u) | >2500 |
| 25 | Leukemia | SR | 25 |
| 26 | Leukemia | A 673 | >2501 |

TABLE 17-continued

| | | Cell Line | MCP-1 (pg/mL) |
|---|---|---|---|
| 27 | Leukemia | K562 | 287 |
| 28 | Leukemia | RPMI-8226 | 528 |
| 29 | Leukemia | Jurkats | 184 |
| 30 | Leukemia | THP-1 | 113 |
| 31 | Leukemia | HUT 78 | 35 |
| 32 | Leukemia | JY | 0 |
| 33 | Leukemia | CEM | 0 |
| 34 | Lung Carcinoma | MV 522 | 74 |
| 35 | Lung adenocarcinoma | EKVX | >2500 |
| 36 | Lung adenocarcinoma | HOP-62 | >2500 |
| 37 | Lung Carcinoma NSC | HOP-92 | 897 |
| 38 | Lung Carcinoma NSC | NCI-H1299 | 384 |
| 39 | Lung Carcinoma NSC | NCI-H2126 | 107 |
| 55 | Lung adenocarcinoma | NCI-H522 | 0 |
| 42 | Lung adenocarcinoma | NCI-H322M | 0 |
| 40 | IPF Lung fibroblasts | A 549 | >2501 |
| 57 | Lung adenocarcinoma | NCI-H292 | 245 |
| 43 | Lung Carcinoma NSC | NCI-H460 | 118 |
| 45 | Lung Squamous NSC | Skmes-1 | 410 |
| 44 | Lung Carcinoma Small Cell | SHP-77 | 1663 |
| 58 | Lung Carcinoma Small Cell | NCI-H510A | >2500 |
| 56 | Lung Carcinoma Small Cell | NCI-H69 | |
| 53 | Mammary Gland Carcinoma | HCC-2218 | 129 |
| 54 | Mammary Gland Carcinoma | HCC-1954 | 113 |
| 46 | Mammary Gland Carcinoma | ZR-75-30 | 357 |
| 47 | Mammary Gland Carcinoma | MCF-7 | 0 |
| 48 | Mammary Gland Carcinoma | MDA-MB-453 | 40 |
| 49 | Mammary Gland Carcinoma | MDA-MB-231 | >2501 |
| 50 | Mammary Gland Carcinoma | MDA-MB-468 | 9 |
| 51 | Mammary Gland Carcinoma | NCI/ADR | 0 |
| 52 | Mammary Gland Carcinoma | T47D | 61 |
| 22 | Mammary Gland Carcinoma | SK-BR-3 | 475 |
| 20 | Mammary Gland Carcinoma | Hs 605T | >2500 |
| 53 | Melanoma | A431 | 56 |
| 54 | Melanoma | LOX IMVI | 105 |
| 55 | Melanoma | M14 | 786 |
| 56 | Melanoma | RPMI 7591 | >2501 |
| 57 | Melanoma | SK-MEL-28 | 29 |
| 58 | Melanoma | UACC-62 | 119 |
| 59 | Melanoma | UACC-257 | 265 |
| 41 | Melanoma | Hs 936.T | 15 |
| 24 | Melanoma | SK-mel-5 | 38 |
| 25 | Melanoma | Hs 940.T | >2500 |
| 26 | Melanoma | A375 | 136 |
| 6 | Melanoma | WM.266.4 | >2500 |
| 27 | Pancreatic Carcinoma | HPAC | 73 |
| 29 | Pancreatic Carcinoma | HPAF II | 47 |
| 41 | Pancreatic Carcinoma | CAPAN-1 | >2500 |
| 60 | Pancreatic Carcinoma | Panc-1 | >2500 |
| 30 | Ovarian Carcinoma | ES2 | 322 |
| 31 | Ovarian Carcinoma | IGROV1 | 199 |
| 32 | Ovarian Carcinoma | MDAH2774 | 314 |
| 33 | Ovarian Carcinoma | SK-OV-3 | 86 |
| 34 | Ovarian Carcinoma | OVCAR-3 | 126 |
| 36 | Ovarian Carcinoma | OVCAR-5 | 336 |
| 37 | Ovarian Carcinoma | OVCAR-8 | 36 |
| 38 | Prostate Carcinoma | 22Rv1 | 55 |
| 39 | Prostate Carcinoma | LNCaP | >2500 |
| 40 | Prostate Carcinoma | DU150 | >2500 |
| 42 | Prostate Carcinoma | PC-3 | 163 |
| 28 | Prostate Carcinoma | DU145 | 68 |
| 43 | Renal Carcinoma | A498 | >2500 |
| 44 | Renal Carcinoma | 786-0(35h) | >2500 |
| 45 | Renal Carcinoma | SK-RC-01 | >2500 |
| 46 | Renal Carcinoma | SK-RC-10 | >2500 |
| 47 | Renal Carcinoma | Caki-1 | 115 |
| 48 | Renal Carcinoma | Caki-2 | >2500 |
| 49 | Renal Carcinoma | RXF-393 | >2500 |
| 50 | Renal Carcinoma | SK-RC-52 | >2500 |
| 51 | Renal Carcinoma | SN12C | >2500 |
| 52 | Renal Carcinoma | TK-10 | 533 |
| 62 | Renal Carcinoma | 769-P | 512 |
| 23 | Liver Carcinoma | C3A | 0 |
| 59 | Liver Carcinoma | HepG2 | >2500 |
| 19 | Cervical Cancer Epidermoid | MS 751 | >2500 |
| 35 | Cervical Cancer | Hela | >2501 |
| | Cervical | C-33A | 20 |
| 1 | Cervical | Ca Ski | 32 |
| 2 | Cervical | ME-180 | 54 |
| 3 | Uterus | KLE | >2500 |
| 4 | Uterus | RL95-2 | 28 |
| 5 | Uterus | HEC-1-A | 47 |
| | | | MCP-1 |

Example 7

Effect of Anti-MCP-1 Antibodies in Mouse Tumor Model

Figure 4:
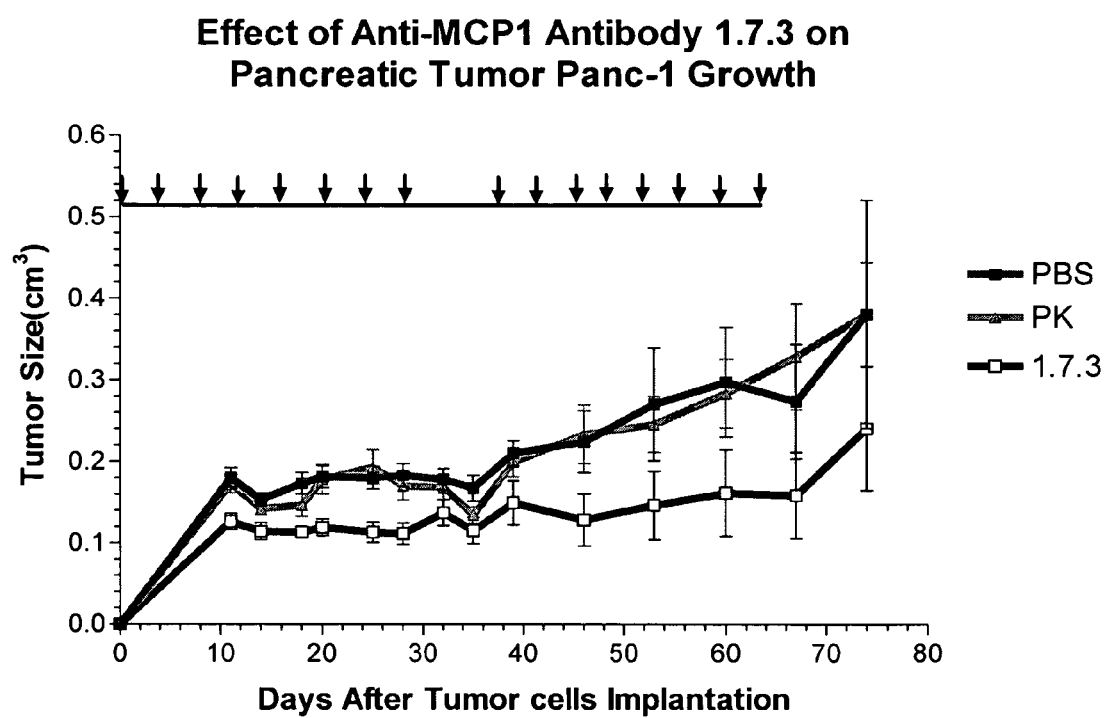
FIG. 4 shows the effect of anti-MCP-1 antibody 1.7.3 on pancreatic tumor Panc-1 growth.

To evaluate the effect of anti-MCP-1 antibodies on the growth of a subcutaneous tumor, exponentially growing Panc-1 cells were harvested and resuspended in 0.2 mL of Hank's Balanced Salt solution (HBSS). Tumors were produced following the injection of $5 \times 10^6$ Panc-1 cells admixed with Growth factor reduced Matrigel into the flanks of female BALB/c nude mice. Beginning on the day of implantation, animals were treated with 0.5 mg of anti-MCP-1 antibody 1.7.3, and antibody PK, which was directed to KLH or PBS at the times indicated on the graph. Tumor growth was monitored weekly and the results presented as mean±SD (FIG. 4). The difference between the control and treated animals was statistically significant when compared using the student T test ($P<0.002$). Accordingly, anti-MCP-1 antibodies provide an effective treatment for reducing tumor growth in vivo.

Example 8

Software-Assisted Analysis of MCP-1 Antibodies

Figure 5:
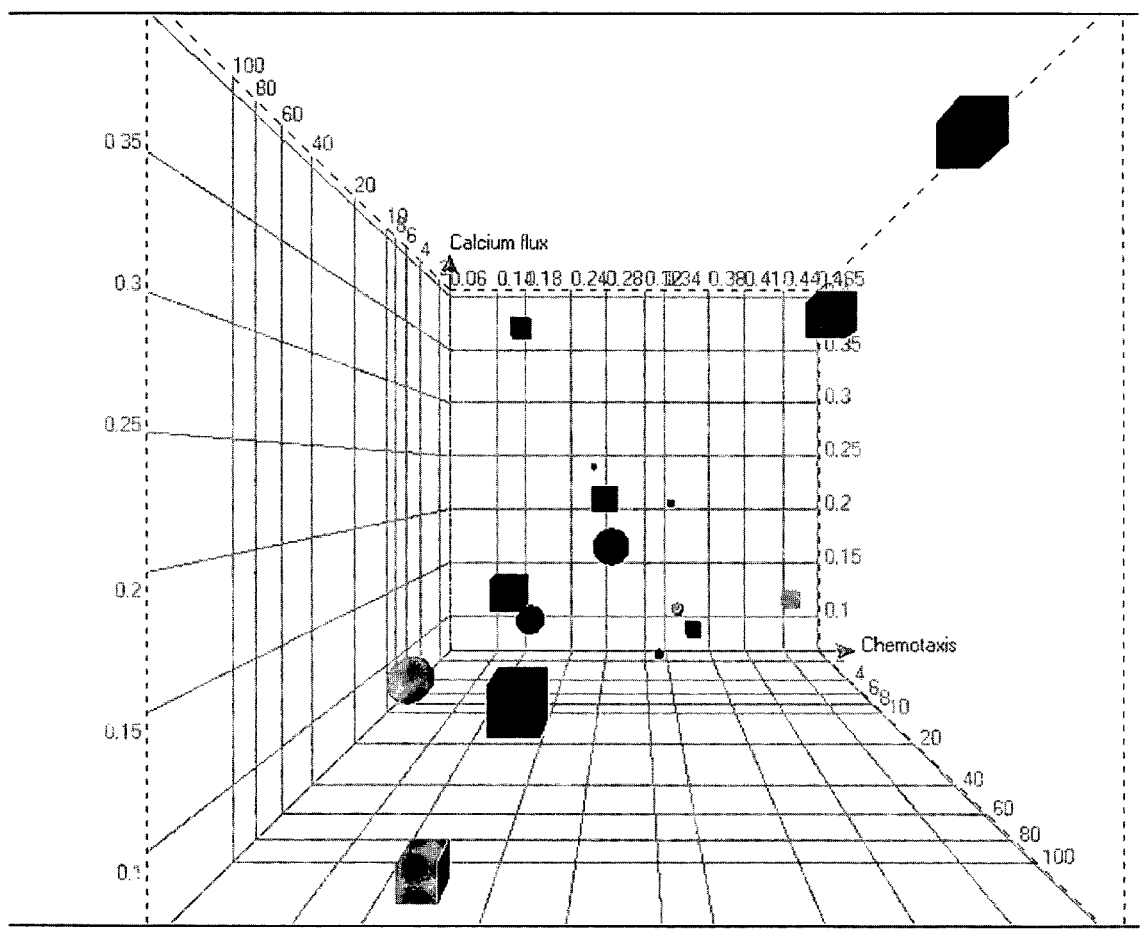
FIG. 5 shows a 3-dimensional scatter plot of calcium flux, chemotaxis and affinity data for the MCP-1 antibodies.
Figure 6:
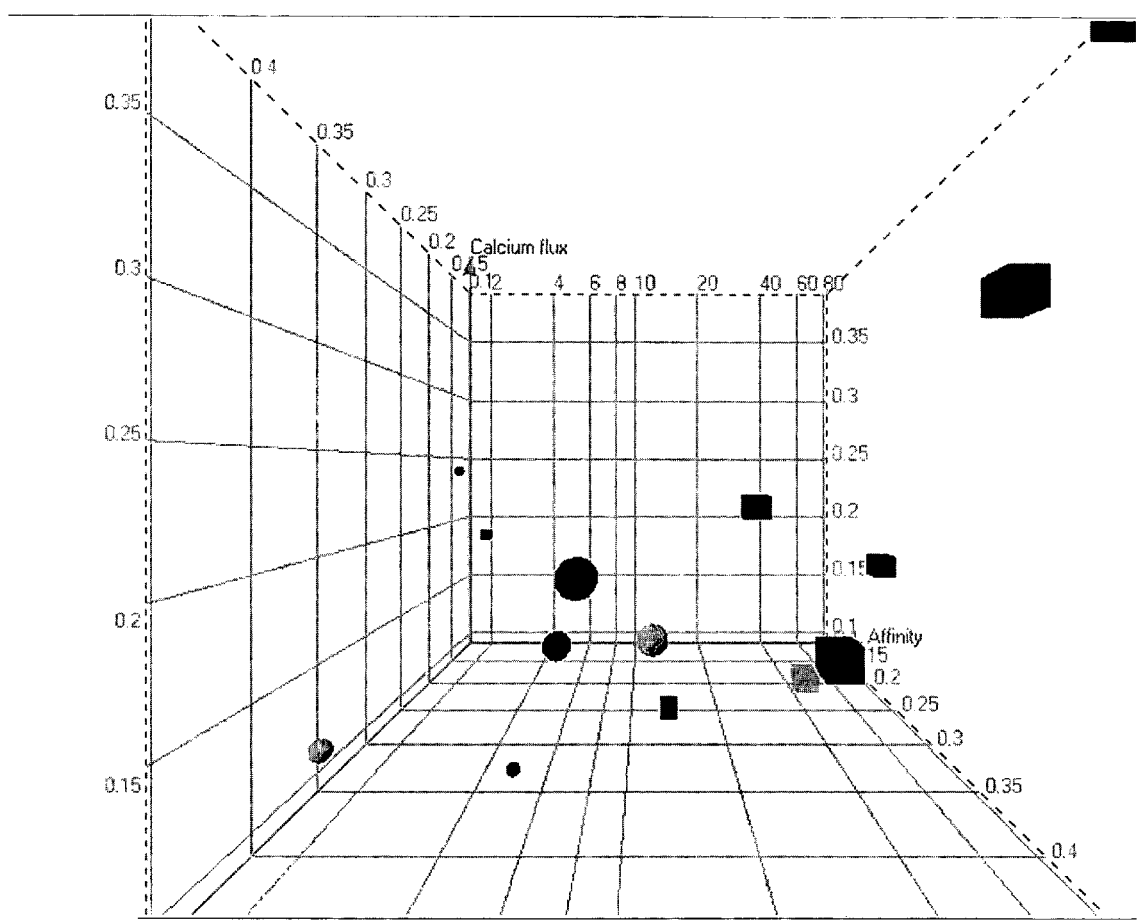
FIG. 6 shows another orientation of a 3-dimensional scatter plot of calcium flux, chemotaxis and affinity data for the MCP-1 antibodies.

The above-described calcium flux, chemotaxis and affinity data for the MCP-1 antibodies were analyzed using Guided Analytic software available from Spotfire, Inc., Somerville, Mass. The results are shown in FIGS. 5 and 6.

Example 9

Structural Analysis of Anti-MCP-1 Antibodies

The variable heavy chains and the variable light chains for the antibodies shown in Table 1 were sequenced to determine their DNA sequences. The complete sequence information for all anti-MCP-1 antibodies are shown in the sequence listing with nucleotide and amino acid sequences for each gamma and kappa chain combination.

Figure 7B:
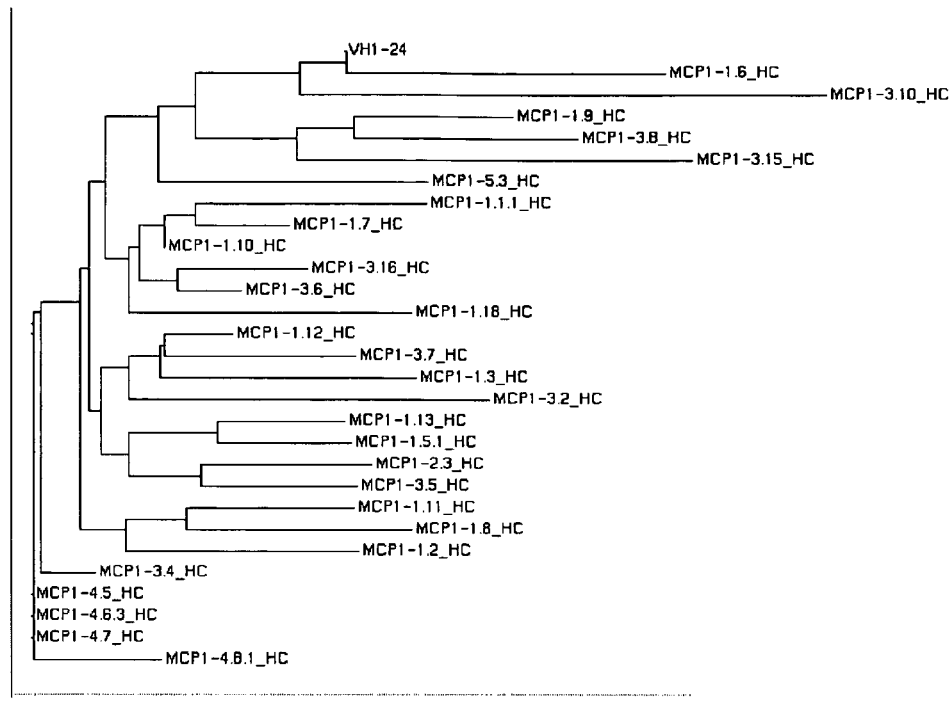
FIG. 7A shows a Clustal W comparison of anti-MCP-1 sequences using VH1-24, indicating the CDR1, CDR2, and CDR3 regions, and the associated dendrogram (FIG. 7B).
Figure 8B:
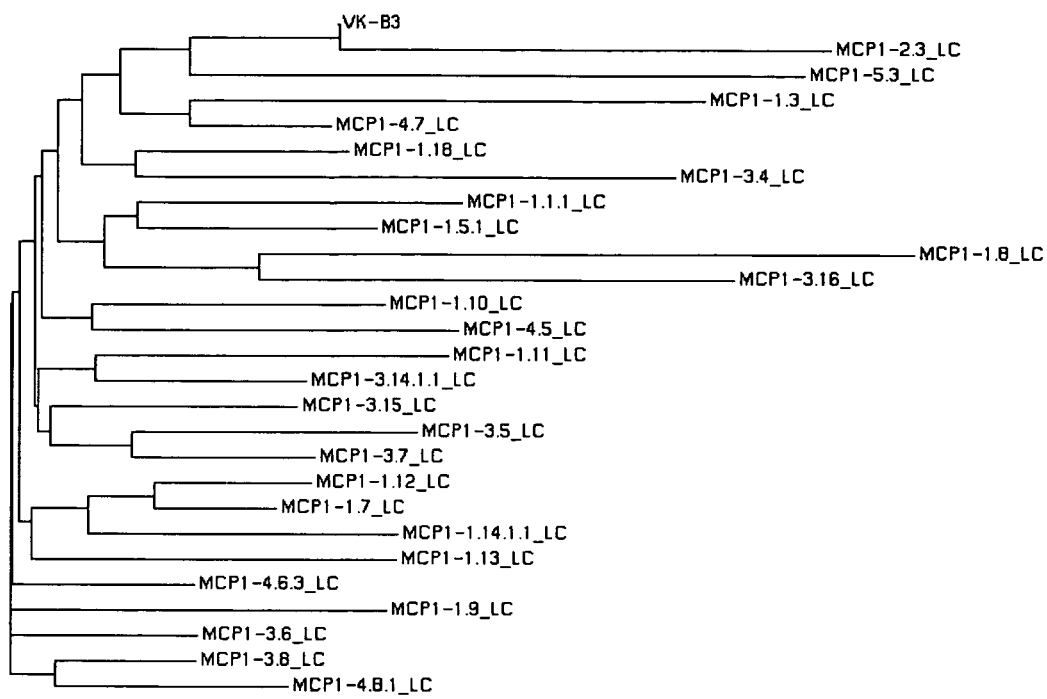
FIG. 8A shows a Clustal W comparison of anti-MCP-1 sequences using VK-B3, indicating the CDR1, CDR2, and CDR3 regions, and the associated dendrogram (FIG. 8B).

The variable heavy sequences were analyzed to determine the VH family, the D-region sequence and the J-region sequence. The sequences were then translated to determine the primary amino acid sequence and compared to the germline VH, D and J-region sequences to assess somatic hypermutations. FIG. 7 shows a Clustal W comparison of anti-MCP-1 sequences using VH1-24, indicating the CD, CDR1, CDR2, and CDR3 regions, and the associated dendrogram. FIG. 8 shows a Clustal W comparison of anti-MCP-1 sequences using VK-B3, indicating the CD, CDR1, CDR2, and CDR3 regions, and the associated dendrogram. FIG. 9 shows a Clustal W comparison of anti-MCP-1 sequences using VK-08, indicating the CD, CDR1, CDR2, and CDR3 regions, and the associated dendrogram. FIG. 10 shows a Clustal W comparison of anti-MCP-1 sequences using VH6-1, indicating the CD, CDR1, CDR2, and CDR3 regions, and the associated dendrogram.

Example 10

Use of Anti-MCP-1 Antibodies as a Diagnostic Agent

A. Detection of MCP-1 Antigen in a Sample

An Enzyme-Linked Immunosorbent Assay (ELISA) for the detection of MCP-1 antigen in a sample is developed. In the assay, wells of a microtiter plate, such as a 96-well microtiter plate or a 384-well microtiter plate, are adsorbed for several hours with a first fully human monoclonal antibody directed against the antigen. The immobilized antibody serves as a capture antibody for any of the antigen that may be present in a test sample. The wells are rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample may be, for example, a serum sample from a subject suspected of having levels of circulating antigen considered to be diagnostic of pathology.

After rinsing away the test sample or standard, the wells are treated with a second fully human monoclonal anti-MCP-1 antibody that is labeled by conjugation with biotin. The labeled anti-MCP-1 antibody serves as a detecting antibody. After rinsing away excess second antibody, the wells are treated with avidin-conjugated horseradish peroxidase (HRP) and a suitable chromogenic substrate. The concentration of the antigen in the test samples is determined by comparison with a standard curve developed from the standard samples.

This ELISA assay provides a highly specific and very sensitive assay for the detection of the MCP-1 antigen in a test sample.

B. Determination of MCP-1 Concentration in Patient Samples

A sandwich ELISA is developed to quantify MCP-1 levels in human serum. The two anti-MCP-1 antibodies used in the sandwich ELISA, preferably recognize different epitopes on the MCP-1 molecule (data not shown). The ELISA is performed as follows: 50 µl of capture anti-MCP-1 antibody in coating buffer (0.1 M $NaHCO_3$, pH 9.6) at a concentration of 2 µg/mL is coated on ELISA plates (Fisher). After incubation at 4° C. overnight, the plates are treated with 200 µl of blocking buffer (0.5% BSA, 0.1% Tween 20, 0.01% Thimerosal in PBS) for 1 hr at 25° C. The plates are washed (3×) using 0.05% Tween 20 in PBS (washing buffer, WB). Normal or patient sera (Clinomics, Bioreclaimation) are diluted in blocking buffer containing 50% human serum. The plates are incubated with serum samples overnight at 4° C., washed with WB, and then incubated with 100 µl/well of biotinylated detection anti-MCP-1 antibody for 1 hr at 25° C. After washing, the plates are incubated with HRP-Streptavidin for 15 min, washed as before, and then treated with 100 µl/well of o-phenylenediamine in $H_2O_2$ (Sigma developing solution) for color generation. The reaction is stopped with 50 µl/well of $H_2SO_4$ (2M) and analyzed using an ELISA plate reader at 492 nm. Concentration of PRO antigen in serum samples is calculated by comparison to dilutions of purified MCP-1 antigen using a four-parameter curve-fitting program.

C. Staging of Cancer in a Patient

It will be appreciated that based on the results set forth and discussed in Examples 10A-10B, through use of embodiments of the invention described herein, it is possible to stage a cancer in a subject based on expression levels of the MCP-1 antigen. For a given type of cancer, samples of blood are taken from subjects diagnosed as being at various stages in the progression of the disease, and/or at various points in the therapeutic treatment of the cancer. The concentration of the MCP-1 antigen present in the blood samples is determined using a method that specifically determines the amount of the antigen that is present. Such a method includes an ELISA method, such as the method described in Examples 10A-10B. Using a population of samples that provides statistically significant results for each stage of progression or therapy, a range of concentrations of the antigen that may be considered characteristic of each stage is designated.

In order to stage the progression of the cancer in a subject under study, or to characterize the response of the subject to a course of therapy, a sample of blood is taken from the subject and the concentration of the MCP-1 antigen present in the sample is determined. The concentration so obtained is used to identify in which range of concentrations the value falls. The range so identified correlates with a stage of progression or a stage of therapy identified in the various populations of diagnosed subjects, thereby providing a stage in the subject under study.

Example 11

Uses of Anti-MCP-1 Antibodies for Tumor Treatment

To determine the in vivo effects of anti-MCP-1 antibody treatment in human patients with tumors, such human patients are injected over a certain amount of time with an effective amount of anti-MCP-1 antibody. At periodic times during the treatment, the human patients are monitored to determine whether their tumors progress, in particular, whether the tumors grow and metastasize.

A tumor patient treated with anti-MCP-1 antibodies has a lower level of tumor growth and metastasis compared to the level of tumor growth and metastasis of tumors in tumor patients treated with control antibodies. Control antibodies that may be used include antibodies of the same isotype as the anti-MCP-1 antibodies tested and further, may not have the ability to bind to MCP-1 tumor antigen.

The foregoing written specification is considered to be sufficient to enable one skilled in the art to practice the invention. The embodiments of the invention described herein are not to be limited in scope by the construct deposited, since the deposited embodiment is intended as a single illustration of certain aspects of the invention and any constructs that are functionally equivalent are within the scope of this invention.

All references cited herein, including patents, patent applications, papers, text books, and the like, and the references cited therein, to the extent that they are not already, are hereby incorporated herein by reference in their entirety.

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. An isolated human monoclonal antibody that binds to MCP-1 and comprises a heavy chain polypeptide having the sequence of SEQ ID NO: 18.

2. The antibody of claim 1, further comprising a light chain polypeptide having the sequence of SEQ ID NO: 20.

3. An isolated antibody immobilized on an insoluble matrix, wherein the antibody is the antibody of claim 2.

4. A composition, comprising the antibody of claim 1, and a pharmaceutically acceptable carrier.

5. An isolated human monoclonal antibody that cross-competes for binding to MCP-1, wherein said antibody comprises a heavy chain polypeptide having the sequence of SEQ ID NO: 18.

6. The antibody of claim 5, wherein said antibody further comprises a light chain polypeptide having the sequence of SEQ ID NO: 20.

7. The antibody of claim 1, wherein said antibody is conjugated to a therapeutic agent.

8. The antibody of claim 7, wherein said therapeutic agent is a toxin.

9. The antibody of claim 8, wherein said toxin is an immunotoxin.

10. The antibody of claim 7, wherein said therapeutic agent is a chemotherapeutic agent.

11. The antibody of claim 10, wherein said chemotherapeutic agent is selected from the group consisting of taxol, doxorubicin, cis-platinum, and 5-fluorouracil.

12. The antibody of claim 7, wherein said therapeutic agent is a radioisotope.

13. The antibody of claim 12, wherein said radioisotope is selected from the group consisting of $^{3}H$, $^{14}C$, $^{15}N$, $^{35}S$, $^{90}Y$, $^{99}Tc$, $^{111}In$, $^{125}I$, and $^{131}I$.

14. An isolated human monoclonal antigen binding fragment that binds to MCP-1 and comprises a heavy chain polypeptide having the sequence of SEQ ID NO: 18.

15. The antigen binding fragment of claim 14, further comprising a light chain polypeptide having the sequence of SEQ ID NO: 20.

16. The antigen binding fragment of claim 14, wherein said binding fragment is selected from the group consisting of Fab, Fab', F(ab')$_2$, and Fv.

17. The antigen binding fragment of claim 16, wherein said fragment is conjugated to a therapeutic agent.

18. An isolated fully human monoclonal antibody or antigen binding fragment thereof that binds to an epitope comprising the amino acid sequence SVQRL (SEQ ID NO:157).

19. The antibody of claim 1, wherein the antibody is fully human.

20. An isolated human monoclonal antibody that binds to MCP-1 and comprises a heavy chain polypeptide having CDR1, CDR2 and CDR3 of SEQ ID NO:18.

21. The antibody of claim 20, further comprising a light chain polypeptide having the CDRs of SEQ ID NO:20.

22. An isolated human monoclonal antigen binding fragment that binds to MCP-1 and comprises a heavy chain polypeptide having CDR1, CDR2 and CDR3 of SEQ ID NO:18.

23. The antigen binding fragment of claim 22, further comprising a light chain polypeptide having CDR1, CDR2 and CDR3 of SEQ ID NO:20.

24. A composition comprising the antibody of claim 20 or the antigen binding fragment of claim 22 and a pharmaceutically acceptable carrier.

25. A method for assaying the level of monocyte chemoattractant protein-1 (MCP-1) in a patient sample, comprising:
contacting the anti-MCP-1 antibody of claim 2 with the patient sample, and
detecting the level of MCP-1 in the patient sample.

26. A method according to claim 25 wherein the patient sample is blood.

27. A method of treating a neoplastic disease, comprising:
selecting an animal in need of treatment for a neoplastic disease; and
administering to said animal a therapeutically effective dose of the human monoclonal antibody of claim 1.

28. The method of claim 27, wherein said neoplastic disease is selected from the group consisting of: breast cancer, ovarian cancer, bladder cancer, lung cancer, glioblastoma, stomach cancer, endometrial cancer, kidney cancer, colon cancer, pancreatic cancer, and prostate cancer.

29. A method of treating inflammatory conditions, comprising:
selecting an animal in need of treatment for an inflammatory condition; and
administering to said animal a therapeutically effective dose of the fully human monoclonal antibody of claim 1.

30. The method of claim 29, wherein said inflammatory condition is selected from the group consisting of: rheumatoid arthritis, glomerulonephritis, atherosclerosis, psoriasis, restenosis, autoimmune disease, and multiple sclerosis.

31. A method of treating a neoplastic disease, comprising:
selecting an animal in need of treatment for a neoplastic disease; and
administering to said animal a therapeutically effective dose of the antibody of claim 20 or the antigen binding fragment of claim 22.

32. The method of claim 31, wherein said neoplastic disease is selected from the group consisting of: breast cancer, ovarian cancer, bladder cancer, lung cancer, glioblastoma, stomach cancer, endometrial cancer, kidney cancer, colon cancer, pancreatic cancer, and prostate cancer.

33. A method of manufacturing the antibody of claim 1, comprising:
immunizing a mammal with a synthetic peptide of MCP-1;
recovering lymphatic cell that expresses the antibody of claim 1 from the immunized mammal; and
fusing the lymphatic cell with a myeloid-type cell to prepare a hybridoma cell that produces the antibody of claim 1.

* * * * *

SEQUENCE LISTING

<160> NUMBER OF SEQ ID NOS: 163

<210> SEQ ID NO 1
<211> LENGTH: 1335
<212> TYPE: DNA
<213> ORGANISM: Homo sapiens

<400> SEQUENCE: 1

```
caggtccagc tggtacagtc tggggctgag gtgaagaagc ctggggcctc agtgaaggtc      60
tcctgcaagg tttccggata cacCctcact gaattatcca tgcactgggt gcgacaggct     120
cctggaaatg ggcttgagtg gatgggaggt tttgatcctg aagatggtga gacaatctac     180
gcacagaggt tccagggcag agtcgtcatg accgaggacc catctacaga cacagcctac     240
atggagctga gcagcctgag atctgaggac acggccgtgt attactgtgc aaccaacgag     300
ttttggagtg gttattttga ctactggggc cagggaaccc tggtcaccgt ctcctcagcc     360
tccaccaagg gcccatcggt cttccccctg gcgccctgct ccaggagcac ctccgagagc     420
acagcggccc tgggctgcct ggtcaaggac tacttccccg aaccggtgac ggtgtcgtgg     480
aactcaggcg ctctgaccag cggcgtgcac accttccag ctgtcctaca gtcctcagga     540
ctctactccc tcagcagcgt ggtgaccgtg ccctccagca acttcggcac ccagacctac     600
acctgcaacg tagatcacaa gcccagcaac accaaggtgg acaagacagt tgagcgcaaa     660
tgttgtgtcg agtgcccacc gtgcccagca ccacctgtgg caggaccgtc agtcttcctc     720
ttccccccaa aacccaagga caccctcatg atctcccgga cccctgaggt cacgtgcgtg     780
gtggtggacg tgagccacga agaccccgag gtccagttca actggtacgt ggacggcgtg     840
gaggtgcata atgccaagac aaagccacgg gaggagcagt tcaacagcac gttccgtgtg     900
gtcagcgtcc tcaccgttgt gcaccaggac tggctgaacg gcaaggagta caagtgcaag     960
gtctccaaca aaggcctccc agcccccatc gagaaaacca tctccaaaac caaagggcag    1020
ccccgagaac cacaggtgta caccctgccc ccatcccggg aggagatgac caagaaccag    1080
gtcagcctga cctgcctggt caaaggcttc taccccagcg acatcgccgt ggagtgggag    1140
agcaatgggc agccggagaa caactacaag accacacctc ccatgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                    1335
```

<210> SEQ ID NO 2
<211> LENGTH: 445
<212> TYPE: PRT
<213> ORGANISM: Homo sapiens

<400> SEQUENCE: 2

```
Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
            20                  25                  30

Ser Met His Trp Val Arg Gln Ala Pro Gly Asn Gly Leu Glu Trp Met
        35                  40                  45

Gly Gly Phe Asp Pro Glu Asp Gly Glu Thr Ile Tyr Ala Gln Arg Phe
    50                  55                  60

Gln Gly Arg Val Val Met Thr Glu Asp Pro Ser Thr Asp Thr Ala Tyr
```

```
                65                  70                  75                  80
        Met Glu Leu Ser Ser Leu Arg Ser Glu Asp Thr Ala Val Tyr Tyr Cys
                            85                  90                  95

Ala Thr Asn Glu Phe Trp Ser Gly Tyr Phe Asp Tyr Trp Gly Gln Gly
                        100                 105                 110

Thr Leu Val Thr Val Ser Ser Ala Ser Thr Lys Gly Pro Ser Val Phe
                    115                 120                 125

Pro Leu Ala Pro Cys Ser Arg Ser Thr Ser Glu Ser Thr Ala Ala Leu
                130                 135                 140

Gly Cys Leu Val Lys Asp Tyr Phe Pro Glu Pro Val Thr Val Ser Trp
        145                 150                 155                 160

Asn Ser Gly Ala Leu Thr Ser Gly Val His Thr Phe Pro Ala Val Leu
                        165                 170                 175

Gln Ser Ser Gly Leu Tyr Ser Leu Ser Ser Val Val Thr Val Pro Ser
                    180                 185                 190

Ser Asn Phe Gly Thr Gln Thr Tyr Thr Cys Asn Val Asp His Lys Pro
                195                 200                 205

Ser Asn Thr Lys Val Asp Lys Thr Val Glu Arg Lys Cys Cys Val Glu
            210                 215                 220

Cys Pro Pro Cys Pro Ala Pro Pro Val Ala Gly Pro Ser Val Phe Leu
        225                 230                 235                 240

Phe Pro Pro Lys Pro Lys Asp Thr Leu Met Ile Ser Arg Thr Pro Glu
                        245                 250                 255

Val Thr Cys Val Val Val Asp Val Ser His Glu Asp Pro Glu Val Gln
                    260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Phe Arg Val Val Ser Val Leu
            290                 295                 300

Thr Val Val His Gln Asp Trp Leu Asn Gly Lys Glu Tyr Lys Cys Lys
        305                 310                 315                 320

Val Ser Asn Lys Gly Leu Pro Ala Pro Ile Glu Lys Thr Ile Ser Lys
                        325                 330                 335

Thr Lys Gly Gln Pro Arg Glu Pro Gln Val Tyr Thr Leu Pro Pro Ser
                    340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
        385                 390                 395                 400

Ser Phe Phe Leu Tyr Ser Lys Leu Thr Val Asp Lys Ser Arg Trp Gln
                        405                 410                 415

Gln Gly Asn Val Phe Ser Cys Ser Val Met His Glu Ala Leu His Asn
                    420                 425                 430

His Tyr Thr Gln Lys Ser Leu Ser Leu Ser Pro Gly Lys
                435                 440                 445

<210> SEQ ID NO 3
<211> LENGTH: 660
<212> TYPE: DNA
<213> ORGANISM: Homo sapiens

<400> SEQUENCE: 3
```

```
gacatcgtga tgacccagtc tccagactcc ctggctatgt ctctgggcga gagggccacc    60
atcaactgta agtccagcca gagtgtttta tacagctcca acaataagaa ctacttagtt   120
tggtaccagc agaaaccagg acagcctcct aaactgctca tttactgggc atctatccgg   180
gaatccgggg tccctgaccg attcagttcc agcgggtctg agacagattt cactctcacc   240
atcagcagcc tgcaggctga agatgtggca gtttattact gtcagcaata ttttagtagt   300
ccgtggacgt tcggccaagg gaccaaggtg gaaatcaaac gaactgtggc tgcaccatct   360
gtcttcatct tcccgccatc tgatgagcag ttgaaatctg gaactgcctc tgttgtgtgc   420
ctgctgaata acttctatcc cagagaggcc aagtacagt  ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
```

```
<210> SEQ ID NO 4
<211> LENGTH: 220
<212> TYPE: PRT
<213> ORGANISM: Homo sapiens

<400> SEQUENCE: 4
```

Asp Ile Val Met Thr Gln Ser Pro Asp Ser Leu Ala Met Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Ser Gly Ser Glu Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

```
<210> SEQ ID NO 5
<211> LENGTH: 475
<212> TYPE: DNA
<213> ORGANISM: Homo sapiens

<400> SEQUENCE: 5
```

```
caggtccagc tggtacagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcctg aagatggtga acaatctac     180 gcacagaagt tccagggcag agtcaccatg accgaggaca catctacaga cacagcctac     240
atggagctga gcagcctgag atctgaggac acggccgtgt attattgtgc aaccaacgaa     300
ttttggagtg gttattttga ctactggggc cagggaaccc tggtcaccgt ctcctcagcc     360
tccaccaagg gcccatcggt cttccccctg gcgccctgct ccaggagcac tacttccccc     420
ggcgtgcaca ccttcccagc tgtcctacag tcctcaggac tctactccct cagca          475
```

<210> SEQ ID NO 6
<211> LENGTH: 158
<212> TYPE: PRT
<213> ORGANISM: Homo sapiens

<400> SEQUENCE: 6

```
Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asn Glu Phe Trp Ser Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Thr Ser Pro Gly Val His Thr
    130                 135                 140

Phe Pro Ala Val Leu Gln Ser Ser Gly Leu Tyr Ser Leu Ser
145                 150                 155
```

<210> SEQ ID NO 7
<211> LENGTH: 477
<212> TYPE: DNA
<213> ORGANISM: Homo sapiens

<400> SEQUENCE: 7

```
gacatcgtga tgacccagtc tccagcctcc ctggctgagt ctctgggcga gagggccacc      60
atcaattgca agtccagcca gagtgtttta tatagctcca acaataagaa ctacttagtt     120
tggtaccagc agaaactagg acagccccct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcaacaata ttatcgtagt     300
ccgtggacgt tcggccaagg gaccaaggtg gaaatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgcc       477
```

<210> SEQ ID NO 8
<211> LENGTH: 159
<212> TYPE: PRT
<213> ORGANISM: Homo sapiens

<400> SEQUENCE: 8

```
Asp Ile Val Met Thr Gln Ser Pro Ala Ser Leu Ala Glu Ser Leu Gly
 1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Val Trp Tyr Gln Gln Lys Leu Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Arg Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala
145                 150                 155
```

<210> SEQ ID NO 9
<211> LENGTH: 556
<212> TYPE: PRT
<213> ORGANISM: Homo sapiens

<400> SEQUENCE: 9

```
Cys Ala Gly Gly Thr Cys Cys Ala Gly Cys Thr Gly Gly Thr Ala Cys
 1               5                  10                  15

Ala Gly Thr Cys Thr Gly Gly Gly Gly Cys Thr Gly Ala Gly Gly Thr
             20                  25                  30

Gly Ala Ala Gly Ala Ala Gly Cys Cys Thr Gly Gly Gly Gly Cys Cys
         35                  40                  45

Thr Cys Ala Gly Thr Gly Ala Ala Gly Gly Thr Cys Thr Cys Cys Thr
 50                  55                  60

Gly Cys Ala Ala Gly Gly Thr Thr Cys Cys Gly Gly Ala Thr Ala Cys
 65                  70                  75                  80

Cys Ala Cys Cys Cys Thr Cys Ala Cys Thr Gly Ala Ala Thr Thr Ala
                 85                  90                  95

Thr Cys Cys Ala Thr Gly Cys Ala Cys Thr Gly Gly Gly Thr Gly Cys
            100                 105                 110

Gly Ala Cys Ala Gly Gly Cys Thr Cys Cys Thr Gly Gly Ala Ala Ala
        115                 120                 125

Ala Gly Gly Gly Cys Thr Thr Gly Ala Gly Thr Gly Gly Ala Thr Gly
130                 135                 140

Gly Gly Ala Gly Gly Thr Thr Thr Thr Ala Thr Cys Cys Thr Cys Gly
145                 150                 155                 160

Ala Ala Gly Ala Thr Gly Gly Thr Gly Ala Ala Cys Ala Ala Thr
            165                 170                 175
```

```
Cys Thr Ala Cys Gly Cys Ala Cys Ala Gly Ala Ala Gly Thr Thr Cys
            180                 185                 190
Cys Ala Gly Gly Gly Cys Ala Gly Ala Gly Thr Cys Ala Cys Cys Ala
            195                 200                 205
Thr Gly Ala Cys Cys Gly Ala Gly Gly Ala Cys Ala Cys Ala Thr Cys
            210                 215                 220
Thr Ala Cys Ala Gly Ala Cys Ala Cys Ala Gly Cys Cys Thr Ala Cys
225                 230                 235                 240
Ala Thr Gly Gly Ala Gly Cys Thr Gly Ala Gly Cys Ala Gly Cys Cys
                245                 250                 255
Thr Gly Ala Gly Ala Thr Cys Thr Gly Ala Gly Gly Ala Cys Ala Cys
            260                 265                 270
Gly Gly Cys Cys Gly Thr Gly Thr Ala Thr Ala Cys Thr Gly Thr
            275                 280                 285
Gly Cys Ala Ala Cys Ala Ala Ala Cys Gly Ala Thr Thr Thr Thr Thr
            290                 295                 300
Gly Gly Ala Gly Thr Gly Gly Thr Thr Ala Thr Thr Ala Thr Ala Ala
305                 310                 315                 320
Cys Thr Ala Cys Thr Gly Gly Gly Gly Cys Cys Ala Gly Gly Gly Ala
            325                 330                 335
Ala Cys Cys Cys Thr Gly Gly Thr Cys Ala Cys Gly Thr Cys Thr
            340                 345                 350
Cys Cys Thr Cys Ala Gly Cys Cys Thr Cys Cys Ala Cys Cys Ala Ala
            355                 360                 365
Gly Gly Gly Cys Cys Ala Thr Cys Gly Gly Thr Cys Thr Thr Cys
            370                 375                 380
Cys Cys Cys Cys Thr Gly Gly Cys Gly Cys Cys Thr Gly Cys Thr
385                 390                 395                 400
Cys Cys Ala Gly Gly Ala Gly Cys Ala Cys Cys Thr Cys Cys Gly Ala
            405                 410                 415
Gly Ala Gly Cys Ala Cys Ala Gly Cys Gly Gly Cys Cys Cys Thr Gly
            420                 425                 430
Gly Gly Cys Thr Gly Cys Cys Thr Gly Gly Thr Cys Ala Ala Gly Gly
            435                 440                 445
Ala Cys Thr Ala Cys Thr Thr Cys Cys Cys Gly Ala Ala Cys Cys
            450                 455                 460
Gly Gly Thr Gly Ala Cys Gly Gly Thr Gly Thr Cys Gly Thr Gly Gly
465                 470                 475                 480
Ala Ala Cys Thr Cys Ala Gly Gly Cys Gly Cys Thr Cys Thr Gly Ala
                485                 490                 495
Cys Cys Ala Gly Cys Gly Gly Cys Gly Thr Gly Cys Ala Cys Ala Cys
            500                 505                 510
Cys Thr Thr Cys Cys Cys Ala Gly Cys Thr Gly Thr Cys Cys Thr Ala
            515                 520                 525
Cys Ala Gly Thr Cys Cys Thr Cys Ala Gly Gly Ala Cys Thr Cys Thr
            530                 535                 540
Ala Cys Thr Cys Cys Cys Thr Cys Ala Gly Cys Ala
545                 550                 555

<210> SEQ ID NO 10
<211> LENGTH: 185
<212> TYPE: PRT
<213> ORGANISM: Homo sapiens

<400> SEQUENCE: 10
```

```
Gln Val Gln Leu Val Gln Ser Gly Ala Glu Val Lys Lys Pro Gly Ala
 1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asn Asp Phe Trp Ser Gly Tyr Tyr Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser
            180                 185

<210> SEQ ID NO 11
<211> LENGTH: 490
<212> TYPE: DNA
<213> ORGANISM: Homo sapiens

<400> SEQUENCE: 11
gacatcgtga tgacccagtc tccagactcc ctggctgtgt ctctgggcga gagggccacc      60
atcaactgca gtccagcca gagtgtttta tacagctcca acaataagaa ctacttagtt     120
tggtaccaac agaaaccagg acagcctcct aaactgctca tttactgggc atctatccgg     180
gaatccgggg tccctgaccg attcagtggc agcgggtctg ggacagattt cactctcacc     240
atcaacagcc tgcaggctga agatgtggca gtttattact gtcagcagta ttttatagt     300 ccgtggacgt tcggccaagg gaccaaggtg gaaatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta                                                            490

<210> SEQ ID NO 12
<211> LENGTH: 163
<212> TYPE: PRT
<213> ORGANISM: Homo sapiens

<400> SEQUENCE: 12

Asp Ile Val Met Thr Gln Ser Pro Asp Ser Leu Ala Val Ser Leu Gly
 1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Lys Pro Gly Gln
        35                  40                  45
```

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Phe Tyr Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly

<210> SEQ ID NO 13
<211> LENGTH: 543
<212> TYPE: DNA
<213> ORGANISM: Homo sapiens

<400> SEQUENCE: 13
caggtccagc tggtacagtc tggggctgag gtgaagaagc ctggggcctc agtgaaggtc      60
tcctgcaagg tttccggaca cccctcact gaattatcca tgcactgggt gcgacaggct     120
cctggaaaag ggcttgagtg gatgggaggt tttgatcctg aagatgatga acaatctac      180 gcacagaagt tccaggacag agtcaccatg accgaggaca catctacaga cacagcctac     240
atggagctga gcagcctaag atctgaggac acggccgtgt attactgtgc aaccaacgat     300
ttttggagtg gttattttga ctgctggggc cagggaaccc tggtcaccgt ctcctcagcc     360
tccaccaagg gcccatcggt cttccccctg gcgccctgct ccaggagcac ctccgagagc     420
acagcggccc tgggctgcct ggtcaaggac tacttccccg aaccggtgac ggtgtcgtgg     480
aactcaggcg ctctgaccag cggcgtgcac accttcccag ctgtcctaca gtcctcagga     540
ctt                                                                   543

<210> SEQ ID NO 14
<211> LENGTH: 181
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Val Ser Gly His Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Asp Glu Thr Ile Tyr Ala Gln Lys Phe
    50                  55                  60

Gln Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asn Asp Phe Trp Ser Gly Tyr Phe Asp Cys Trp Gly Gln Gly

-continued

```
                    100                 105                 110
Thr Leu Val Thr Val Ser Ser Ala Ser Thr Lys Gly Pro Ser Val Phe
            115                 120                 125
Pro Leu Ala Pro Cys Ser Arg Ser Thr Ser Glu Ser Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu
            180

<210> SEQ ID NO 15
<211> LENGTH: 490
<212> TYPE: DNA
<213> ORGANISM: Homo sapiens

<400> SEQUENCE: 15
gacatcgtgc tgacccagtc tccagactcc ctggctgtgt gtctgggcga gagggccacc      60
atcaactgca agtccagcca gagtgtttta tatagtccca caataagaaa cttcttagtt     120
tggtaccagc agagaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtagt     300
ccgtggacgt tcggccaagg gaccaaggtg gaaatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta                                                            490

<210> SEQ ID NO 16
<211> LENGTH: 163
<212> TYPE: PRT
<213> ORGANISM: Homo sapiens

<400> SEQUENCE: 16

Asp Ile Val Leu Thr Gln Ser Pro Asp Ser Leu Ala Val Cys Leu Gly
1               5                   10                  15
Glu Arg Ala Thr Ile Asn Cys Lys Ser Ser Gln Ser Val Leu Tyr Ser
            20                  25                  30
Pro Asn Asn Lys Asn Phe Leu Val Trp Tyr Gln Gln Arg Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Ser Ser Pro Trp Thr Phe Gly Gln Gly Thr Lys Val Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
```

-continued

```
145                 150                 155                 160
Gln Ser Gly

<210> SEQ ID NO 17
<211> LENGTH: 1335
<212> TYPE: DNA
<213> ORGANISM: Homo sapiens

<400> SEQUENCE: 17
caggtccagc tggtacagtc tggggctgag gtgaagaagc ctggggcctc agtgaaggtc    60
tcctgcaagg tttccggata caccctcact gaattatcca tgcactgggt gcgacaggct   120
cctggaaaag ggcttgagtg gatgggaggt tttgatcctg aagatggtga acaatctac    180 gcacagaagt tccagggcag agtcaccatg accgaggaca catctacaga cacagtctac   240
atggagctga gcagcctgag atctgaggac acggccatgt attactgtgc aacacgggag   300
ttttggactg gttattttga ccactggggc cagggaaccc tggtcaccgt ctcctcagcc   360
tccaccaagg gcccatcggt cttccccctg gcgccctgct ccaggagcac ctccgagagc   420
acagcggccc tgggctgcct ggtcaaggac tacttcccg aaccggtgac ggtgtcgtgg    480
aactcaggcg ctctgaccag cggcgtgcac accttcccag ctgtcctaca gtcctcagga   540
ctctactccc tcagcagcgt ggtgaccgtg ccctccagca acttcggcac ccagacctac   600
acctgcaacg tagatcacaa gcccagcaac accaaggtgg acaagacagt tgagcgcaaa   660
tgttgtgtcg agtgcccacc gtgcccagca ccacctgtgg caggaccgtc agtcttcctc   720
ttccccccaa aacccaagga caccctcatg atctcccgga cccctgaggt cacgtgcgtg   780
gtggtggacg tgagccacga agaccccgag gtccagttca actggtacgt ggacggcgtg   840
gaggtgcata atgccaagac aaagccacgg gaggagcagt tcaacagcac gttccgtgtg   900
gtcagcgtcc tcaccgttgt gcaccaggac tggctgaacg gcaaggagta caagtgcaag   960
gtctccaaca aaggcctccc agcccccatc gagaaaacca tctccaaaac caaagggcag  1020
ccccgagaac acaggtgta cccctgcccc catcccggg aggagatgac caagaaccag   1080
gtcagcctga cctgcctggt caaaggcttc taccccagcg acatcgccgt ggagtgggag  1140
agcaatgggc agccggagaa caactacaag accacacctc ccatgctgga ctccgacggc  1200
tccttcttcc tctacagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gtaaa                                                   1335

<210> SEQ ID NO 18
<211> LENGTH: 445
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Val Tyr
```

```
                65                  70                  75                  80
Met Glu Leu Ser Ser Leu Arg Ser Glu Asp Thr Ala Met Tyr Tyr Cys
                    85                  90                  95

Ala Thr Arg Glu Phe Trp Thr Gly Tyr Phe Asp His Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Asn Phe Gly Thr Gln Thr Tyr Thr Cys Asn Val Asp His Lys Pro
                195                 200                 205

Ser Asn Thr Lys Val Asp Lys Thr Val Glu Arg Lys Cys Cys Val Glu
            210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
                260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Phe Arg Val Val Ser Val Leu
            290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 19
<211> LENGTH: 660
<212> TYPE: DNA
<213> ORGANISM: Homo sapiens

<400> SEQUENCE: 19
```

-continued

```
gacatcgtga tgacccagtc tccagactcc ctggctgtgt ctctgggcga gagggccacc      60
atcaactgca agtccagcca gagtgtttta tacagctcca acaataagaa ctacttagtt     120
tggtatcagc agaaaccagg acagcctcct aaactgctca tttactgggc atctatccgg     180
gaatccgggg tcccggaccg attcagtggc agcgggtctg ggacagattt cactctcacc     240
atcagcagcc tgcaggctga agatgtggca gtttattact gtcagcaata ttatagtact     300
ccgctcactt tcggcggagg gaccaaggtg gagatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
```

<210> SEQ ID NO 20
<211> LENGTH: 220
<212> TYPE: PRT
<213> ORGANISM: Homo sapiens

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 21
<211> LENGTH: 543
<212> TYPE: DNA
<213> ORGANISM: Homo sapiens

<400> SEQUENCE: 21

```
caggtccagc tggtacagtc tgggctgag gtgaagaagc ctggggcctc agtgaaggtc      60
tcctgcaagg tttccggata cactttact  gaattatcca tgcactgggt gcgacaggct    120
cctggaaaag gcttgagtg  gatgggaggt tttgatcctg aagatggtga aacaagctac    180
gcacagaagt tccggggcag agtcaccatg accgaggaca catctacaga cacagcccac    240
atggagctga gcagcctgag atctgaggac acggccgtgt attactgtgc aaccaacgat    300
ttttggagtg gttatttga  ctattgggc  cagggaaccc tggtcaccgt ctcctcagcc    360
tccaccaagg gcccatcggt cttcccctg  gcgccctgct ccaggagcac ctccgagagc    420
acagcggccc tgggctgcct ggtcaaggac tacttcccg  aaccggtgac ggtgtcgtgg    480
aactcaggcg ctctgaccag cggcgtgcac accttcccag ctgtcctaca gtcctcagga    540
ctt                                                                  543
```

```
<210> SEQ ID NO 22
<211> LENGTH: 181
<212> TYPE: PRT
<213> ORGANISM: Homo sapiens

<400> SEQUENCE: 22
```

```
Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Phe Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ser Tyr Ala Gln Lys Phe
    50                  55                  60

Arg Gly Arg Val Thr Met Thr Glu Asp Thr Ser Thr Asp Thr Ala His
65                  70                  75                  80

Met Glu Leu Ser Ser Leu Arg Ser Glu Asp Thr Ala Val Tyr Tyr Cys
                85                  90                  95

Ala Thr Asn Asp Phe Trp Ser Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu
            180
```

```
<210> SEQ ID NO 23
<211> LENGTH: 460
<212> TYPE: DNA
<213> ORGANISM: Homo sapiens

<400> SEQUENCE: 23
```

```
gacatccaga tgacccagtc tccatcttcc gtgtctgcat ctgtaggaga cagagtcacc     60
atcacttgtc gggcgagtca gggtattgac atctacttag cctggtatca gcagaaacca   120
gggaaagccc ctaagctcct gatcaatgct gcatccagtt tgcaaaacgg ggtcccctca   180
```

| | | | | |
|---|---|---|---|---|
| aggttcggcg | gcagtggatc | tgggacagat | tcactctca | ccatcagcgg cctgcagcct | 240 |
| gaagattttg | caacttacta | ttgtcaactg | acttacttt | tcccgtggac gttcggccaa | 300 |
| gggaccaagg | tggaaatcaa | acgaactgtg | gctgcaccat | ctgtcttcat cttcccgcca | 360 |
| tctgatgagc | agttgaaatc | tggaactgcc | tctgttgtgt | gcctgctgaa taacttctat | 420 |
| cccagagagg | ccaaagtaca | gtggaaggtg | gataacgccc | | 460 |

<210> SEQ ID NO 24
<211> LENGTH: 153
<212> TYPE: PRT
<213> ORGANISM: Homo sapiens

<400> SEQUENCE: 24

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ile Tyr
            20                  25                  30

Leu Ala Trp Tyr Gln Gln Lys Pro Gly Lys Ala Pro Lys Leu Leu Ile
        35                  40                  45

Asn Ala Ala Ser Ser Leu Gln Asn Gly Val Pro Ser Arg Phe Gly Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Leu Thr Tyr Phe Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala
145                 150

<210> SEQ ID NO 25
<211> LENGTH: 543
<212> TYPE: DNA
<213> ORGANISM: Homo sapiens

<400> SEQUENCE: 25

| | | | | |
|---|---|---|---|---|
| caggtccagc | tggtacagtc | tggggctgag | gtgaagaagc | ctggggcctc agtgaaggtc | 60 |
| tcctgcaagg | tttccggata | caccctcact | gaattatcca | tgcactgggt gcgacgaatt | 120 |
| cctggaaaag | ggcttgagtg | gatgggaggt | tttgaccctg | aagatggtga aacaatctac | 180 |
| gcacagaagt | tccagggcag | agtcaccatg | accgaggaca | catctacaga cacagcctac | 240 |
| atggagctga | gcagcctgag | atctgaggac | acggccgtgt | attactgtgc aacaaacgat | 300 |
| ttttggagtg | gctattgggg | ccactggggc | cagggaaccc | tggtcaccgt ctcctcagcc | 360 |
| tccaccaagg | gcccatcggt | cttccccctg | gcgccctgct | ccaggagcac ctccgagagc | 420 |
| acagcggccc | tgggctgcct | ggtcaaggac | tacttccccg | aaccggtgac ggtgtcgtgg | 480 |
| aactcaggcg | ctctgaccag | cggcgtgcac | accttcccag | ctgtcctaca gtcctcagga | 540 |
| ctt | | | | | 543 |

<210> SEQ ID NO 26
<211> LENGTH: 181

<212> TYPE: PRT
<213> ORGANISM: Homo sapiens

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Arg Ile Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asn Asp Phe Trp Ser Gly Tyr Trp Gly His Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu
            180

<210> SEQ ID NO 27
<211> LENGTH: 459
<212> TYPE: DNA
<213> ORGANISM: Homo sapiens

<400> SEQUENCE: 27
gacatcgtga tgacccagtc tccagactcc ctggctgtgt ctctgggcga gagggccacc      60
atcaactgca gtccagcca gagtgtttta tacagctcca acaataagaa ctacctagct     120
tggtaccaag ctgctcattt actggacata tatccgggaa tccggggtcc ctgaccgatt    180
cagtggcagc gggtctggga cagatttcac tctcaccatc agcagcctgc aggctgaaga    240
tgtggcagtt tattactgtc aggaacatta gtattccg tggacgttcg gccaagggac      300
caaggtggaa atcaaacgaa ctgtggctgc accatctgtc ttcatcttcc cgccatctga    360
tgagcagttg aactgcctct gttgtgtgcc tgctgaataa cttctatccc agagaggcca    420
aagtacagtg gaaggtggat aacgccctcc aatcgggta                           459

<210> SEQ ID NO 28
<211> LENGTH: 149
<212> TYPE: PRT
<213> ORGANISM: Homo sapiens

<400> SEQUENCE: 28

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Leu Leu Ile Tyr Trp Thr
         35                  40                  45

Tyr Ile Arg Glu Ser Gly Val Pro Asp Arg Phe Ser Gly Ser Gly Ser
     50                  55                  60

Gly Thr Asp Phe Thr Leu Thr Ile Ser Ser Leu Gln Ala Glu Asp Val
 65                  70                  75                  80

Ala Val Tyr Tyr Cys Gln Glu His Tyr Ser Ile Pro Trp Thr Phe Gly
                 85                  90                  95

Gln Gly Thr Lys Val Glu Ile Lys Arg Thr Val Ala Ala Pro Ser Val
            100                 105                 110

Phe Ile Phe Pro Pro Ser Asp Glu Gln Leu Asn Cys Leu Cys Cys Val
        115                 120                 125

Pro Ala Glu Leu Leu Ser Gln Arg Gly Gln Ser Thr Val Glu Gly Gly
    130                 135                 140

Arg Pro Pro Ile Gly
145

<210> SEQ ID NO 29
<211> LENGTH: 524
<212> TYPE: DNA
<213> ORGANISM: Homo sapiens

<400> SEQUENCE: 29
caggtccagc tggtacagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcctg aagatgatga acaatctac      180 gcacagaagt tccagggcag agtcaccatg accgaggaca catctacaga cacggcctac     240
atggagctga gcagcctgag atctgaggac acggccgtgt atttctgtgc aaccaacgat     300
ttttggagtg gttattttga ctgctgggac cagggaaccc tggtcaccgt ctcctcagcc     360
tccaccaagg gcccatcggt cttccccctg gcgccctgct ccaggaacac tccgagagc      420 acagcggccc tgggctgcct ggtcaaggac tacttccccg aaccggtgac ggtgtcgtgg     480
aactcaggcg ctctgaccag cggcgtgcac accttcccag ctgt                     524

<210> SEQ ID NO 30
<211> LENGTH: 174
<212> TYPE: PRT
<213> ORGANISM: Homo sapiens

<400> SEQUENCE: 30

Gln Val Gln Leu Val Gln Ser Gly Ala Glu Val Lys Lys Pro Gly Ala
  1               5                  10                  15

Ser Val Lys Val Ser Cys Lys Val Ser Gly Tyr Thr Leu Thr Glu Leu
             20                  25                  30

Ser Met His Trp Val Arg Gln Ala Pro Gly Lys Gly Leu Glu Trp Met
         35                  40                  45

Gly Gly Phe Asp Pro Glu Asp Asp Glu Thr Ile Tyr Ala Gln Lys Phe
     50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Phe Cys
                 85                  90                  95

Ala Thr Asn Asp Phe Trp Ser Gly Tyr Phe Asp Cys Trp Asp Gln Gly
            100                 105                 110

```
Thr Leu Val Thr Val Ser Ser Ala Ser Thr Lys Gly Pro Ser Val Phe
            115                 120                 125

Pro Leu Ala Pro Cys Ser Arg Asn Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala
                165                 170

<210> SEQ ID NO 31
<211> LENGTH: 490
<212> TYPE: DNA
<213> ORGANISM: Homo sapiens

<400> SEQUENCE: 31
gacatcgtga tgacccagtc tccagactcc ctggctgcgt ctctgggcga gagggccacc      60
atcaactgca agtccagtca gagtgtttta tacaggtcca acaataagaa ttatttagtt     120
tggtaccagc aaaaaccagg acagcctcct aagctgctca tttactgggc atctatccgg     180
gaatccgggg tccctgaccg attcagtggc agcgggtctg ggacagattt cactctcacc     240
atcagcagcc tgcaggctga agatgtggca gtttatttct gtcagcaata ttatagttct     300
ccgtggacgt ttggccaagg gaccaaggtg gaaatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta                                                           490

<210> SEQ ID NO 32
<211> LENGTH: 163
<212> TYPE: PRT
<213> ORGANISM: Homo sapiens

<400> SEQUENCE: 32

Asp Ile Val Met Thr Gln Ser Pro Asp Ser Leu Ala Ala Ser Leu Gly
1               5                   10                  15

Glu Arg Ala Thr Ile Asn Cys Lys Ser Ser Gln Ser Val Leu Tyr Arg
            20                  25                  30

Ser Asn Asn Lys Asn Tyr Leu Val Trp Tyr Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Ser Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly
```

<210> SEQ ID NO 33
<211> LENGTH: 545
<212> TYPE: DNA
<213> ORGANISM: Homo sapiens

<400> SEQUENCE: 33

```
caggtccagc tggtacagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcctg aagatggtga acaatctac     180
gcacagaagt tccagggcag agtcaccatg accgaggaca catctacaga cacagcctac     240
atggagctga gcagcctgag atctgaggac acggccgtgt attactgtgc aacctggtat     300
agtgggatct acttagcttt tgatatctgg ggccaaggga caatggtcac cgtctcttca     360
gcctccacca agggcccatc ggtcttcccc ctggcgccct gctccaggag cacctccgag     420
agcacagcgg ccctgggctg cctggtcaag gactacttcc ccgaaccggt gacggtgtcg     480
tggaactcag gcgctctgac cagcggcgtg cacaccttcc cagctgtcct acagtcctca     540
ggatt                                                                 545
```

<210> SEQ ID NO 34
<211> LENGTH: 181
<212> TYPE: PRT
<213> ORGANISM: Homo sapiens

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Trp Tyr Ser Gly Ile Tyr Leu Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly
            180

<210> SEQ ID NO 35
<211> LENGTH: 472
<212> TYPE: DNA
<213> ORGANISM: Homo sapiens

<400> SEQUENCE: 35

```
gaaattgtgc tgactcagtc tccagacttt cagtctgtga ctccaaagga gaaagtcacc    60
atcacctgcc gggccagtca gagcattggt agtagcttac actggtacca gcagaaacca   120
gatcagtctc caaagctcct catcaagtat gcttcccagt ccttctcagg ggtcccctcg   180
aggttcagtg gcagtggatc tgggacagat ttcaccctca ccatcaatag cctggaagct   240
gaagatgctg caacgtatta ctgtcatcag agtagtagtt acctcacac tttcggcgga   300 gggaccaagg tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg ta           472
```

<210> SEQ ID NO 36
<211> LENGTH: 157
<212> TYPE: PRT
<213> ORGANISM: Homo sapiens

<400> SEQUENCE: 36

```
Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro His
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly
145                 150                 155
```

<210> SEQ ID NO 37
<211> LENGTH: 1335
<212> TYPE: DNA
<213> ORGANISM: Homo sapiens

<400> SEQUENCE: 37

```
caggtccagt tggtacagtc tggggctgag gtgaagaagc ctggggcctc agtgaaggtc    60
tcctgcaagg tttccggata caccctcact gaattatcca tgcactgggt gcgacaggct   120
cctggaaaag ggcttgagtg gatgggaggt tttgatcctg aagatggtga acaatctac    180 gcacagaagt tccagggcag agtcagtatg accgaggaca catccacaga cacagcctac   240
atggagctga gcagcctgag atctgaggac acggccgtgt atttctgtgc aaccaacgaa   300
ttttggagtg gttattttga ctactggggc caggaaccc tggtcaccgt ctcctcagcc   360
tccaccaagg gcccatcggt cttccccctg gcgccctgct ccaggagcac ctccgagagc   420
acagcggccc tgggctgcct ggtcaaggac tacttcccg aaccggtgac ggtgtcgtgg   480
aactcaggcg ctctgaccag cggcgtgcac accttcccag ctgtcctaca gtcctcagga   540
```

```
ctctactccc tcagcagcgt ggtgaccgtg ccctccagca acttcggcac ccagacctac    600
acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttccccccaa acccaaggac accctcatg atctcccgga ccccctgaggt cacgtgcgtg    780 gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgttgt gcaccaggac tggctgaacg gcaaggagta caagtgcaag    960
gtctccaaca aaggcctccc agcccccatc gagaaaacca tctccaaaac caaagggcag   1020
ccccgagaac cacaggtgta caccctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacacctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaa                                                     1335
```

<210> SEQ ID NO 38
<211> LENGTH: 445
<212> TYPE: PRT
<213> ORGANISM: Homo sapiens

<400> SEQUENCE: 38

```
Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Ser Met Thr Glu Asp Thr Ser Thr Asp Thr Ala Tyr
65                  70                  75                  80

Met Glu Leu Ser Ser Leu Arg Ser Glu Asp Thr Ala Val Tyr Phe Cys
                85                  90                  95

Ala Thr Asn Glu Phe Trp Ser Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220
```

```
Cys Pro Pro Cys Pro Ala Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
        260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
        435                 440                 445

<210> SEQ ID NO 39
<211> LENGTH: 660
<212> TYPE: DNA
<213> ORGANISM: Homo sapiens

<400> SEQUENCE: 39
gacatcgtga tgacccagtc tccagactcc ctggctgtgt ctctgggcga gagggccacc      60
atcaactgca agtccagcca gagtgtttta tacagctcca acaataagaa ctatttagtt     120
tggtaccagc agagaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttttttattct     300 ccgtggacgt tcggccaagg gaccaaggta gaaatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660

<210> SEQ ID NO 40
<211> LENGTH: 220
<212> TYPE: PRT
<213> ORGANISM: Homo sapiens

<400> SEQUENCE: 40
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Arg Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Tyr Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 41
<211> LENGTH: 556
<212> TYPE: DNA
<213> ORGANISM: Homo sapiens

<400> SEQUENCE: 41
caggtccagc tggtacagtc tggggctgag gtgaagaagc ctggggcctc agtgaaggtc      60
tcctgcaagg tttccggaca catttttcact gaattatcca tacactgggt gcgacaggct    120
cctggaaaag gctcgagtg gatgggaggt tttgatcctg aagatggtga acaatctac       180 gcacagaagt tccagggcag agtcaccatg accgaggaca tctacagaca cagtctac      240 atggagctga gcagcctgag atctgaggac acggccgtgt attactgtgc aaccaacgat    300
ttttggagtg gttattttga ctactgggc cagggaaccc tggtcaccgt ctcctcagcc     360
tccaccaagg gcccatcggt cttccccctg gcgccctgct ccaggagcac ctccgagagc    420
acagcggccc tgggctgcct ggtcaaggac tacttcccccg aaccggtgac ggtgtcgtgg   480
aactcaggcg ctctgaccag cggcgtgcac accttcccag ctgtcctaca gtcctcagga    540
ctctactccc tcagca                                                     556

<210> SEQ ID NO 42
<211> LENGTH: 185
<212> TYPE: PRT
<213> ORGANISM: Homo sapiens

<400> SEQUENCE: 42

```
Gln Val Gln Leu Val Gln Ser Gly Ala Glu Val Lys Lys Pro Gly Ala
 1               5                  10                  15
Ser Val Lys Val Ser Cys Lys Val Ser Gly His Ile Phe Thr Glu Leu
            20                  25                  30
Ser Ile His Trp Val Arg Gln Ala Pro Gly Lys Gly Leu Glu Trp Met
        35                  40                  45
Gly Gly Phe Asp Pro Glu Asp Gly Glu Thr Ile Tyr Ala Gln Lys Phe
    50                  55                  60
Gln Gly Arg Val Thr Met Thr Glu Asp Thr Ser Thr Asp Thr Val Tyr
65                  70                  75                  80
Met Glu Leu Ser Ser Leu Arg Ser Glu Asp Thr Ala Val Tyr Tyr Cys
                85                  90                  95
Ala Thr Asn Asp Phe Trp Ser Gly Tyr Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser
                180                 185

<210> SEQ ID NO 43
<211> LENGTH: 490
<212> TYPE: DNA
<213> ORGANISM: Homo sapiens

<400> SEQUENCE: 43
gacatcgtga tgacccagtc tccaggctcc ctggctgtgt ctctgggcga gagggccacc      60
atcaactgca agtccagcca gagtatttta ttcaggtcca acaataagaa ctatttaact     120
tggtaccagc agaaaccagg acagcctcct aaactgctca tttactgggc atctatccgg     180
gaatccgggg tccctgatcg attcagtggc agcgggtctg ggtcaaattt cactctcacc     240
atcaccagcc tgcaggctga agatgtggca atttattact gtcagcaata ttatagtagt     300
ccgtggacgt tcggccaagg gaccaaggtg gaaatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta                                                            490

<210> SEQ ID NO 44
<211> LENGTH: 163
<212> TYPE: PRT
<213> ORGANISM: Homo sapiens

<400> SEQUENCE: 44

Asp Ile Val Met Thr Gln Ser Pro Gly Ser Leu Ala Val Ser Leu Gly
 1               5                  10                  15
Glu Arg Ala Thr Ile Asn Cys Lys Ser Ser Gln Ser Ile Leu Phe Arg
            20                  25                  30
Ser Asn Asn Lys Asn Tyr Leu Thr Trp Tyr Gln Gln Lys Pro Gly Gln
        35                  40                  45
```

```
Pro Pro Lys Leu Leu Ile Tyr Trp Ala Ser Ile Arg Glu Ser Gly Val
    50                  55                  60
Pro Asp Arg Phe Ser Gly Ser Gly Ser Gly Asn Phe Thr Leu Thr
65                  70                  75                  80
Ile Thr Ser Leu Gln Ala Glu Asp Val Ala Ile Tyr Tyr Cys Gln Gln
                85                  90                  95
Tyr Tyr Ser Ser Pro Trp Thr Phe Gly Gln Gly Thr Lys Val Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly
```

```
<210> SEQ ID NO 45
<211> LENGTH: 559
<212> TYPE: DNA
<213> ORGANISM: Homo sapiens

<400> SEQUENCE: 45
caggtccagc tggtacagtc tggggctgag gtgaagaagc ctggggcctc agtgaaggtc      60
tcctgcaagg tttccggata cacccTcact gaattatcca tgcactgggt gcgacaggct     120
cctggaaaag ggcttgagtg gatgggaggt tttgatcctg aagatggtga acaatcaac     180
gcacagaagt tccagggcag agtcaccatg accgaggaca tctacagaca caggctac      240
atggagctga gcagcctgag atctgaggac acggccgtgt attactgtgc aacagatcct    300
ggtggatata gtggctactt tgaccactgg ggccagggaa ccctggtcac cgtctcctca    360
gcctccacca agggcccatc ggtcttcccc ctggcgccct gctccaggag cacctccgag    420
agcacagcgg ccctgggctg cctggtcaag gactacttcc ccgaaccggt gacggtgtcg    480
tggaactcag gcgctctgac cagcggcgtg cacaccttcc cagctgtcct acagtcctca    540
ggactctact ccctcagca                                                 559
```

```
<210> SEQ ID NO 46
<211> LENGTH: 186
<212> TYPE: PRT
<213> ORGANISM: Homo sapiens

<400> SEQUENCE: 46

Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Leu Thr Glu Leu
            20                  25                  30
Ser Met His Trp Val Arg Gln Ala Pro Gly Lys Gly Leu Glu Trp Met
        35                  40                  45
Gly Gly Phe Asp Pro Glu Asp Gly Glu Thr Ile Asn Ala Gln Lys Phe
    50                  55                  60
Gln Gly Arg Val Thr Met Thr Glu Asp Thr Ser Thr Asp Thr Gly Tyr
65                  70                  75                  80
Met Glu Leu Ser Ser Leu Arg Ser Glu Asp Thr Ala Val Tyr Tyr Cys
                85                  90                  95
Ala Thr Asp Pro Gly Gly Tyr Ser Gly Tyr Phe Asp His Trp Gly Gln
            100                 105                 110
```

```
Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser
            180                 185

<210> SEQ ID NO 47
<211> LENGTH: 464
<212> TYPE: DNA
<213> ORGANISM: Homo sapiens

<400> SEQUENCE: 47
gacatcgtga tgacccagtc tccagatttc ctggctgtgt ctctgggcga gagggccacc      60
atcaactgca agtccagcca gagtgttttt tacagctcca acaataagaa ctacttagtt     120
tggtaccagc agaaacccgg acagcctcct aagctgctcc tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagttct     300
ccgtggacgt tcggccaagg gaccaaggtg gaaatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaa                     464

<210> SEQ ID NO 48
<211> LENGTH: 154
<212> TYPE: PRT
<213> ORGANISM: Homo sapiens

<400> SEQUENCE: 48

Asp Ile Val Met Thr Gln Ser Pro Asp Phe Leu Ala Val Ser Leu Gly
1               5                   10                  15

Glu Arg Pro Thr Ile Asn Cys Lys Ser Ser Gln Ser Val Phe Tyr Ser
            20                  25                  30

Ser Asn Asn Lys Asn Tyr Leu Val Trp Tyr Gln Gln Lys Pro Gly Gln
        35                  40                  45

Pro Pro Lys Leu Leu Leu Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp
145                 150
```

<210> SEQ ID NO 49
<211> LENGTH: 476
<212> TYPE: DNA
<213> ORGANISM: Homo sapiens

<400> SEQUENCE: 49

| | | |
|---|---|---|
| caggtccagc tggtacagtc tggggctgag gtgaagaagc ctggggcctc agtgaaggtc | 60 |
| tcctgcaagg tttccggata caccctcact gaattatcca tgcactgggt gcgacaggct | 120 |
| cctggaaaag ggcttgagtg gatgggaggt tttgatcctg aagatgatga acaatctac | 180 |
| gcacagaagt tccagggcag agtcaccatg accgaggaca catctacaca cacagcctac | 240 |
| atggaactga gcagcctgag atctgaggac acggccgtgt attactgtgc aacacacgat | 300 |
| ttttggagtg cttatttta ctactggggc cagggaaccc tggtcaccgt ctcctcagct | 360 |
| tccaccaagg gcccatccgt cttcccctg cgccctgct ccaggagcac ctccgagagc | 420 |
| acagccgccc tgggctgcct ggtcaaggac tacttcccg aaccggtgac ggtgtc | 476 |

<210> SEQ ID NO 50
<211> LENGTH: 158
<212> TYPE: PRT
<213> ORGANISM: Homo sapiens

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Asp Glu Thr Ile Tyr Ala Gln Lys Phe
    50                  55                  60

Gln Gly Arg Val Thr Met Thr Glu Asp Thr Ser Thr His Thr Ala Tyr
65                  70                  75                  80

Met Glu Leu Ser Ser Leu Arg Ser Glu Asp Thr Ala Val Tyr Tyr Cys
                85                  90                  95

Ala Thr His Asp Phe Trp Ser Ala Tyr Phe Tyr Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val
145                 150                 155

<210> SEQ ID NO 51
<211> LENGTH: 490
<212> TYPE: DNA
<213> ORGANISM: Homo sapiens

<400> SEQUENCE: 51

| | | |
|---|---|---|
| gacatcgtga tgacccagtc tccagactcc ctggctgtgt ctctgggcga gagggccacc | 60 |
| atcaactgca gtccagcca gagtgtttta tacggctcca acaataagag ctacttagct | 120 |
| tggtaccagc agaaaccagg acagcctcct aagctgctca tttactgggc atctacccgg | 180 |
| gaatccgggg tccctgaccg attcagtggc agcgggtctg ggacagattt cactctcacc | 240 |
| atcagcagcc tgcaggctgc agatgtggca gtttattact gtcagcaaca ttatagtact | 300 |

```
ccgtgcagtt ttggccaggg gaccaaactg gagatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta                                                          490
```

<210> SEQ ID NO 52
<211> LENGTH: 163
<212> TYPE: PRT
<213> ORGANISM: Homo sapiens

<400> SEQUENCE: 52

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Gly
            20                  25                  30

Ser Asn Asn Lys Ser Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Ala Asp Val Ala Val Tyr Tyr Cys Gln Gln
                85                  90                  95

His Tyr Ser Thr Pro Cys Ser Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly
```

<210> SEQ ID NO 53
<211> LENGTH: 550
<212> TYPE: DNA
<213> ORGANISM: Homo sapiens

<400> SEQUENCE: 53

```
caggtgcagc tggtgcagtc tggggctgag gtgaagaagc ctggggcctc agtgaaggtc     60
tcctgcaagg cttctggata caccttcacc ggctactatc tgcactgggt gcgacaggcc    120
cctggacaag gcttgagtg gatgggatgg atcaacccct acaatgatgg cacaaactat    180
gcacagaagt tcagggcag ggtcaccatg accaggaca cgtccatcag cacagcctac    240
atggagctga gcaggctgag atctgacgac acggccgttt attactgtgc gagagatata    300
gccgcagctg gagccgtcta ctttgactac tggggccagg gaaccctggt caccgtctcc    360
tcagcttcca ccaagggccc atccgtcttc cccctggcgc cctgctccag gagcacctcc    420
gagagcacag ccgccctggg ctgcctggtc aaggactact tccccgaacc ggtgacggt    480 gtcgtggaac tcaggcgccc tgaccagcgg cgtgcacacc ttcccggctg tcctacagtc    540
ctcaggactt                                                           550
```

<210> SEQ ID NO 54
<211> LENGTH: 183

```
<212> TYPE: PRT
<213> ORGANISM: Homo sapiens

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Leu His Trp Val Arg Gln Ala Pro Gly Gln Gly Leu Glu Trp Met
        35                  40                  45

Gly Trp Ile Asn Pro Tyr Asn Asp Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ile Ala Ala Ala Gly Ala Val Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Arg Thr Gly Asp Gly
145                 150                 155                 160

Val Val Glu Leu Arg Arg Pro Asp Gln Arg Ala His Leu Pro Gly
                165                 170                 175

Cys Pro Thr Val Leu Arg Thr
            180

<210> SEQ ID NO 55
<211> LENGTH: 458
<212> TYPE: DNA
<213> ORGANISM: Homo sapiens

<400> SEQUENCE: 55
gacatccaga tgacccagtc tccatcctcc ctgtctgcat ctgtaggaga cagagtcacc      60
atcacttgcc aggcgagtca ggacattacc acctatttaa attggtatca gcagaaacca    120
gggaaagccc ctaagctcct gatctacgat gcatccaatt tggaaacagg ggtcccatca    180
aggttcagtg gaagtggatc tgggacagat tttactttca ccatcagcag cctgcagcct    240
gaagatattg caacatatta ctgtcaacaa tatgataatc tcccgatcac cttcggccaa    300
gggacacgac tggagattaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gggaaggtgg ataacgcc                            458

<210> SEQ ID NO 56
<211> LENGTH: 152
<212> TYPE: PRT
<213> ORGANISM: Homo sapiens

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Thr Tyr
            20                  25                  30
```

Leu Asn Trp Tyr Gln Gln Lys Pro Gly Lys Ala Pro Lys Leu Leu Ile
           35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Ile
                 85                  90                  95

Thr Phe Gly Gln Gly Thr Arg Leu Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Gly Arg Trp Ile Thr
145                 150

<210> SEQ ID NO 57
<211> LENGTH: 571
<212> TYPE: DNA
<213> ORGANISM: Homo sapiens

<400> SEQUENCE: 57
caggtccagc tggtacagtc tggggctgag gtgaagaagc ctggggcctc agtgaaggtc      60
tcctgcaagg tttccggata cacccTcact gaattatcca tgcactgggt gcgacaggct     120
cctggaaaag ggcttgagtg gatgggaggt tttgatcctg aagatggtga acaatctac      180 gcacagaagt tccagggcag agtcatgatg accgaggaca catctacaga cacagccttc     240
atggacctga gcagcctgag atctgaggac acggccgtgt attactgtgc aacagacgat     300
atgttgaccc ctcactacct ctacttcggt atggacgtct ggggccaagg gaccacggtc     360
accgtctcct cagcttccac caagggccca tccgtcttcc ccctggcgcc ctgctccagg     420
agcacctccg agagcacagc cgccctgggc tgcctggtca aggactactt ccccgaaccg     480
gtgacggtgt cgtggaactc aggcgccctg accagcggcg tgcacacctt cccggctgtc     540
ctacagtcct caggactcta ctccctcagc a                                    571

<210> SEQ ID NO 58
<211> LENGTH: 190
<212> TYPE: PRT
<213> ORGANISM: Homo sapiens

<400> SEQUENCE: 58

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
             20                  25                  30

Ser Met His Trp Val Arg Gln Ala Pro Gly Lys Gly Leu Glu Trp Met
         35                  40                  45

Gly Gly Phe Asp Pro Glu Asp Gly Glu Thr Ile Tyr Ala Gln Lys Phe
     50                  55                  60

Gln Gly Arg Val Met Met Thr Glu Asp Thr Ser Thr Asp Thr Ala Phe
 65                  70                  75                  80

Met Asp Leu Ser Ser Leu Arg Ser Glu Asp Thr Ala Val Tyr Tyr Cys
                 85                  90                  95

Ala Thr Asp Asp Met Leu Thr Pro His Tyr Leu Tyr Phe Gly Met Asp

```
                100                 105                 110
Val Trp Gly Gln Gly Thr Thr Val Thr Val Ser Ser Ala Ser Thr Lys
            115                 120                 125

Gly Pro Ser Val Phe Pro Leu Ala Pro Cys Ser Arg Ser Thr Ser Glu
        130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser
            180                 185                 190

<210> SEQ ID NO 59
<211> LENGTH: 458
<212> TYPE: DNA
<213> ORGANISM: Homo sapiens

<400> SEQUENCE: 59
gacatccaga tgacccagtc tccatcctcc ctgtctgcat ctgtaggaga cagagtcacc      60
atcacttgcc gggcaagtca gggcattaga aatgatttag gctggtatca gcagaaacca    120
gggaaagccc ctaagcgcct gatctatgct acatccagtt tgcaaagtgg ggtcccatca    180
aggttcagcg gcagtggatc tgggacagaa ttcactctca caatcagcag cctgcagcct    240
gaagattttg caacttatta ctgtctacag cataatactt acccattcac tttcggccct    300
gggaccaaag tggatatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgc                             458

<210> SEQ ID NO 60
<211> LENGTH: 152
<212> TYPE: PRT
<213> ORGANISM: Homo sapiens

<400> SEQUENCE: 60

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn
145                 150
```

<210> SEQ ID NO 61
<211> LENGTH: 1338
<212> TYPE: DNA
<213> ORGANISM: Homo sapiens

<400> SEQUENCE: 61

```
caggtgcagc tgcaggagtc gggcccagga ctggtgaagc cttcacagac cctgtccctc        60
acctgcactg tctcaggtgg ctccatcagc agtggtggta actactggaa ctggatccgc       120
cagcacccag ggaagggcct ggagtggatt gggtacatct attacagtgg aaacacctac       180
tacaacccgt ccctcaagag tcgaattacc atatcaatag acacgtctaa gaaccagttc       240
tccctgaccc tgagctctgt gactgccgcg gacacggccg tgtattactg tgcgagagat       300
ggtggagacg atgcttttga tatctggggc caagggacaa tggtcaccgt ctcttcagct       360
tccaccaagg gcccatccgt cttccccctg gcgccctgct ccaggagcac ctccgagagc       420
acagccgccc tgggctgcct ggtcaaggac tacttccccg aaccggtgac ggtgtcgtgg       480
aactcaggcg ccctgaccag cggcgtgcac accttcccgg ctgtcctaca gtcctcagga       540
ctctactccc tcagcagcgt ggtgaccgtg ccctccagca gcttgggcac gaagacctac       600
acctgcaacg tagatcacaa gcccagcaac accaaggtgg acaagagagt tgagtccaaa       660
tatggtcccc catgcccatc atgcccagca cctgagttcc tggggggacc atcagtcttc       720
ctgttccccc caaaacccaa ggacactctc atgatctccc ggacccctga ggtcacgtgc       780
gtggtggtgg acgtgagcca ggaagacccc gaggtccagt tcaactggta cgtggatggc       840
gtggaggtgc ataatgccaa gacaaagccg cgggaggagc agttcaacag cacgtaccgt       900
gtggtcagcg tcctcaccgt cctgcaccag gactggctga acggcaagga gtacaagtgc       960
aaggtctcca acaaaggcct cccgtcctcc atcgagaaaa ccatctccaa agccaaaggg      1020
cagccccgag agccacaggt gtacaccctg cccccatccc aggaggagat gaccaagaac      1080
caggtcagcc tgacctgcct ggtcaaaggc ttctacccca gcgacatcgc cgtggagtgg      1140
gagagcaatg ggcagccgga gaacaactac aagaccacgc ctcccgtgct ggactccgac      1200
ggctccttct tcctctacag caggctaacc gtggacaaga gcaggtggca ggaggggaat      1260
gtcttctcat gctccgtgat gcatgaggct ctgcacaacc actacacaca gaagagcctc      1320
tccctgtctc tgggtaaa                                                   1338
```

<210> SEQ ID NO 62
<211> LENGTH: 446
<212> TYPE: PRT
<213> ORGANISM: Homo sapiens

<400> SEQUENCE: 62

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Asn Tyr Trp Asn Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Ile Thr Ile Ser Ile Asp Thr Ser Lys Asn Gln Phe
65                  70                  75                  80

Ser Leu Thr Leu Ser Ser Val Thr Ala Ala Asp Thr Ala Val Tyr Tyr
                85                  90                  95
```

```
Cys Ala Arg Asp Gly Gly Asp Asp Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
            435                 440                 445

<210> SEQ ID NO 63
<211> LENGTH: 642
<212> TYPE: DNA
<213> ORGANISM: Homo sapiens

<400> SEQUENCE: 63
gacatccaga tgacccagtc tccatcctcc ctgtctgcat ctgtaggaga cagagtcacc      60
atcacttgcc aggcgagtca ggacattagc aactatttaa attggtatca gcagaaacca     120
```

| | |
|---|---|
| gggaaagccc ctaaactcct gatctacgat gcatccaatt tggaaacagg ggtcccatca | 180 |
| aggttcagtg aagtggatc tgggacagat tttactttca ccatcaacag cctgcagcct | 240 |
| gaagatattg caacatatta ctgtcaagaa tataataatc tcccgtacag ttttggccag | 300 |
| gggaccaagt tggagatcaa acgaactgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga aaacacaaa gtctacgcct gcgaagtcac ccatcagggc | 600 |
| ctgagctcgc ccgtcacaaa gagcttcaac aggggagagt gt | 642 |

<210> SEQ ID NO 64
<211> LENGTH: 214
<212> TYPE: PRT
<213> ORGANISM: Homo sapiens

<400> SEQUENCE: 64

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Asn Ser Leu Gln Pro
 65                  70                  75                  80

Glu Asp Ile Ala Thr Tyr Tyr Cys Gln Glu Tyr Asn Asn Leu Pro Tyr
                 85                  90                  95

Ser Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 1341
<212> TYPE: DNA
<213> ORGANISM: Homo sapiens

<400> SEQUENCE: 65

| | |
|---|---|
| caggtccagc tggtacagtc tggggctgag gtgaagaagc ctggggcctc agtgcaggtc | 60 |
| tcctgcaagg tttccggaga caccctcact gaattatcca tgcactgggt gcgacaggct | 120 |

-continued

```
cctggaaaag ggcttgagtg gatgggaggt tttgatcctg aagatggtga aacaatctac      180
gcacggaagt tccagggcag agtcaccatg accgaggaca catctacaga cacagtttac      240
atggagctga gcagcctgag atctgaggac acggccgtgt atttctgtgc aacagattca      300
cgtggatata gtggctactt tgacaactgg ggccagggaa ccctggtcac cgtctcctca      360
gcttccacca agggcccatc cgtcttcccc ctggcgccct gctccaggag cacctccgag      420
agcacagccg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacgaagacc      600
tacacctgca acgtagatca caagcccagc aacaccaagg tggacaagag agttgagtcc      660
aaatatggtc ccccatgccc atcatgccca gcacctgagt tcctgggggg accatcagtc      720
ttcctgttcc ccccaaaacc caaggacact ctcatgatct cccggacccc tgaggtcacg      780
tgcgtggtgg tggacgtgag ccaggaagac cccgaggtcc agttcaactg gtacgtggat      840
ggcgtggagg tgcataatgc caagacaaag ccgcgggagg agcagttcaa cagcacgtac      900
cgtgtggtca gcgtcctcac cgtcctgcac caggactggc tgaacggcaa ggagtacaag      960
tgcaaggtct ccaacaaagg cctcccgtcc tccatcgaga aaaccatctc caaagccaaa     1020
gggcagcccc gagagccaca ggtgtacacc ctgcccccat cccaggagga gatgaccaag     1080
aaccaggtca gcctgacctg cctggtcaaa ggcttctacc ccagcgacat cgccgtggag     1140
tgggagagca atgggcagcc ggagaacaac tacaagacca cgcctcccgt gctggactcc     1200
gacggctcct tcttcctcta cagcaggcta accgtggaca agagcaggtg gcaggagggg     1260
aatgtcttct catgctccgt gatgcatgag gctctgcaca accactacac acagaagagc     1320
ctctccctgt ctctgggtaa a                                                1341
```

<210> SEQ ID NO 66
<211> LENGTH: 447
<212> TYPE: PRT
<213> ORGANISM: Homo sapiens

<400> SEQUENCE: 66

```
Gln Val Gln Leu Val Gln Ser Gly Ala Glu Val Lys Lys Pro Gly Ala
 1               5                  10                  15

Ser Val Gln Val Ser Cys Lys Val Ser Gly Asp Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Arg Lys Phe
    50                  55                  60

Gln Gly Arg Val Thr Met Thr Glu Asp Thr Ser Thr Asp Thr Val Tyr
65                  70                  75                  80

Met Glu Leu Ser Ser Leu Arg Ser Glu Asp Thr Ala Val Tyr Phe Cys
                85                  90                  95

Ala Thr Asp Ser Arg Gly Tyr Ser Gly Tyr Phe Asp Asn Trp Gly Gln
           100                 105                 110

Gly Thr Leu Val Thr Val Ser Ser Ala Ser Thr Lys Gly Pro Ser Val
       115                 120                 125

Phe Pro Leu Ala Pro Cys Ser Arg Ser Thr Ser Glu Ser Thr Ala Ala
   130                 135                 140

Leu Gly Cys Leu Val Lys Asp Tyr Phe Pro Glu Pro Val Thr Val Ser
```

```
                145                 150                 155                 160
Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 67
<211> LENGTH: 660
<212> TYPE: DNA
<213> ORGANISM: Homo sapiens

<400> SEQUENCE: 67
gacatcgtga tgacccagtc tccagactcc ctggctgtgt ctctgggcga gagggccacc      60
atcaactgca gtccagcca gagtgttta tacagctcca acaataacaa ctacttagtt      120
tggtaccagc agaaaccagg acagcctcct aaattgctca tttactgggc atctacccgg     180
gaattcgggg ttcctgaccg attcagtggc agcgggtctg ggacagattt cactctcacc     240
atcagcagcc tgcaggctga agatgtggca gtttattact gtcagcaata ttattttct     300 ccgtggacgt tcggccaagg gaccaaggtg gaaatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
```

```
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660
```

<210> SEQ ID NO 68
<211> LENGTH: 220
<212> TYPE: PRT
<213> ORGANISM: Homo sapiens

<400> SEQUENCE: 68

```
Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
             20                  25                  30

Ser Asn Asn Asn Asn Tyr Leu Val Trp Tyr Gln Gln Lys Pro Gly Gln
         35                  40                  45

Pro Pro Lys Leu Leu Ile Tyr Trp Ala Ser Thr Arg Glu Phe Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Phe Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 69
<211> LENGTH: 556
<212> TYPE: DNA
<213> ORGANISM: Homo sapiens

<400> SEQUENCE: 69

```
caggtccagc tggtacagtc tggggctgag gtgaagaagc ctggggcctc agtgaaggtc       60
tcctgcaagg tttccggata caccctcact gatttatcca tgcactgggt gcgacaggct      120
cctggaaaag ggcttgagtg gatgggaggt tttgatcctg aagatggtga acaatctac       180 gcacagaagt tccagggcag agtcaccatg accgaggaca catcttcaga cacagcctac      240
atggagctga gcagcctgag atctgaggac acggccgtgt attactgtgc aacccacgaa      300
ttttggagtg gttatttttga ctactggggc cagggaaccc tggtcaccgt ctcctcagct      360
tccaccaagg gcccatccgt cttccccctg gcgccctgct ccaggagcac ctccgagagc      420
```

```
acagccgccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagca                                                    556
```

<210> SEQ ID NO 70
<211> LENGTH: 185
<212> TYPE: PRT
<213> ORGANISM: Homo sapiens

<400> SEQUENCE: 70

```
Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Asp Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Ser Asp Thr Ala Tyr
 65                 70                  75                  80

Met Glu Leu Ser Ser Leu Arg Ser Glu Asp Thr Ala Val Tyr Tyr Cys
                85                  90                  95

Ala Thr His Glu Phe Trp Ser Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser
            180                 185
```

<210> SEQ ID NO 71
<211> LENGTH: 476
<212> TYPE: DNA
<213> ORGANISM: Homo sapiens

<400> SEQUENCE: 71

```
gacatcgtga tgacccagtc tccagactcc ctggctgtgt ctctgggcga gagggccacc     60
atcaactgca agtccagcca gagtgtttta ttcagctcca acaataagag ctacttaact    120
tggtaccagc agaaaccagg acagcctcct aaattactca ttttctgggc atctatccgg    180
gaatccgggg tccctgaccg aatcagtggc agcgggtctg ggacagatct cactctcacc    240
atcagcagcc tgcaggctga agatgcggca gtttattact gtcagcaata ttatagtagt    300
ccgtggacgt tcggccaagg gaccaaggtg gaaatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgc       476
```

<210> SEQ ID NO 72
<211> LENGTH: 158
<212> TYPE: PRT
<213> ORGANISM: Homo sapiens

<400> SEQUENCE: 72

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Ser Tyr Leu Thr Trp Tyr Gln Gln Lys Pro Gly Gln
        35                  40                  45

Pro Pro Lys Leu Leu Ile Phe Trp Ala Ser Ile Arg Glu Ser Gly Val
    50                  55                  60

Pro Asp Arg Ile Ser Gly Ser Gly Ser Gly Thr Asp Leu Thr Leu Thr
65                  70                  75                  80

Ile Ser Ser Leu Gln Ala Glu Asp Ala Ala Val Tyr Tyr Cys Gln Gln
                85                  90                  95

Tyr Tyr Ser Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn
145                 150                 155

<210> SEQ ID NO 73
<211> LENGTH: 546
<212> TYPE: DNA
<213> ORGANISM: Homo sapiens

<400> SEQUENCE: 73
caggtccagc tggtacagtc tggggctgag gtgaagaagc ctggggcctc agtgaaggtc    60
tcctgcaagg tttccggata caccctcagt gaattatcca tgcactgggt gcgacaggct   120
cctggaaaag ggcttgagtg gatgggaggt tttgatcctg aagatggtga ataatccac    180
gcacagaagt tccagggcag agtcaccatg accgaggaca catctacaga cacagcctac   240
atggagctga gcagcctgag atctgaggac acggccgtgt attactgtgc aacaggcgat   300
ttttggagtg gttattacct tgactggtgg ggccagggaa ccctggtcac cgtctcctca   360
gcttccacca agggcccatc cgtcttcccc ctggcgccct gctccaggag cacctccgag   420
agcacagccg ccctgggctg cctggtcaag gactacttcc ccgaaccggt gacggtgtcg   480
tggaactcag gcgccctgac cagcggcgtg cacaccttcc cggctgtcct acagtcctca   540
ggactt                                                              546

<210> SEQ ID NO 74
<211> LENGTH: 182
<212> TYPE: PRT
<213> ORGANISM: Homo sapiens

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Ser Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Ile Ile His Ala Gln Lys Phe

```
                50                  55                  60
Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Asp Phe Trp Ser Gly Tyr Tyr Leu Asp Trp Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu
                180

<210> SEQ ID NO 75
<211> LENGTH: 457
<212> TYPE: DNA
<213> ORGANISM: Homo sapiens

<400> SEQUENCE: 75
gaaatagtga tgatgcagtc tccagccacc ctgtctgtgt ctccagggga aagagccacc      60
ctctcctgca gggccagtca gagtgttaac agcaacttag cctggtacca gcagaaacct    120
ggccaggctc ccaggctcct catcaacggt gcatccacca gggccactgg catcccagcc    180
aggttcagtg gcagtgggtc tgggacagag ttcaccctca ccatcagcag cctgcagtct    240
gaagattttg caatttatta ctgtcagcag tataatgact ggcctacgtt cactttcggc    300
ggagggacca aggtggagat caatcgaact gtggctgcac catctgtctt catcttcccg    360
ccatctgatg agcagttgaa atctggaact gcctctgttg tgtgcctgct gaataacttc    420
tatcccagag aggccaaagt acagtgggaa ggtggat                             457

<210> SEQ ID NO 76
<211> LENGTH: 152
<212> TYPE: PRT
<213> ORGANISM: Homo sapiens

<400> SEQUENCE: 76

Glu Ile Val Met Met Gln Ser Pro Ala Thr Leu Ser Val Ser Pro Gly
 1               5                  10                  15

Glu Arg Ala Thr Leu Ser Cys Arg Ala Ser Gln Ser Val Asn Ser Asn
                 20                  25                  30

Leu Ala Trp Tyr Gln Gln Lys Pro Gly Gln Ala Pro Arg Leu Leu Ile
                 35                  40                  45

Asn Gly Ala Ser Thr Arg Ala Thr Gly Ile Pro Ala Arg Phe Ser Gly
             50                  55                  60

Ser Gly Ser Gly Thr Glu Phe Thr Leu Thr Ile Ser Ser Leu Gln Ser
 65                  70                  75                  80

Glu Asp Phe Ala Ile Tyr Tyr Cys Gln Gln Tyr Asn Asp Trp Pro Thr
                 85                  90                  95

Phe Thr Phe Gly Gly Gly Thr Lys Val Glu Ile Asn Arg Thr Val Ala
                100                 105                 110
```

```
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Glu Gly Gly
145                 150
```

<210> SEQ ID NO 77
<211> LENGTH: 470
<212> TYPE: DNA
<213> ORGANISM: Homo sapiens

<400> SEQUENCE: 77

```
caggtccagc tggtacagtc tggggctgag gtgaagaagc ctggggcctc agtgaaggtc    60
tcctgcaagg tttccggata caccctcact gaattatcca tgcactgggt gcgacaggct   120
cctggaaaag gcttgagtg gatgggaggt tttgatcctg aagatggtga acaatgtac    180
gcacagaagt tccagggcag agtcaccatg accgaggaca catctacaga cacagcctac   240
atggagctga gcagcctgag atctgaggac acggccgtgt attactgtgc aaccgacgat   300
ttttggagtg gttatttga ctactgggc cagggaaccc tggtcaccgt ctcctcagcc    360
tccaccaagg gcccatcggt cttccccctg gcgccctgct ccaggagcac ctccgagagc   420
acagcggccc tgggctgcct ggtcaaggac tacttccccg aaccggcagg              470
```

<210> SEQ ID NO 78
<211> LENGTH: 156
<212> TYPE: PRT
<213> ORGANISM: Homo sapiens

<400> SEQUENCE: 78

```
Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Leu Thr Glu Leu
            20                  25                  30
Ser Met His Trp Val Arg Gln Ala Pro Gly Lys Gly Leu Glu Trp Met
        35                  40                  45
Gly Gly Phe Asp Pro Glu Asp Gly Glu Thr Met Tyr Ala Gln Lys Phe
    50                  55                  60
Gln Gly Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr Asp Asp Phe Trp Ser Gly Tyr Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Ala
145                 150                 155
```

<210> SEQ ID NO 79
<211> LENGTH: 490
<212> TYPE: DNA
<213> ORGANISM: Homo sapiens

<400> SEQUENCE: 79

```
gacatcgtga tgacccagtc tccagactcc ctggctgtgt ctctggacga gagggccacc    60
atcaactgca agtccagcca gagtgtttta tacagtccca accaaaagaa ctacttagtt   120
tggtatcagc agaagccagg acagcctcct aagctgctcc tttactgggc atctatccgg   180
gaatccgggg tccctgaccg attcagtggc agcgggtctg ggacagattt cactctcacc   240
atcagcagcc tgcaggctga agatgtggca gtttattact gtcaacaaag ttattttact   300
ccgtggacgt tcggccaagg gaccaaggtg gaaatcaaac gaactgtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta                                                          490

<210> SEQ ID NO 80
<211> LENGTH: 163
<212> TYPE: PRT
<213> ORGANISM: Homo sapiens

<400> SEQUENCE: 80

Asp Ile Val Met Thr Gln Ser Pro Asp Ser Leu Ala Val Ser Leu Asp
 1               5                  10                  15

Glu Arg Ala Thr Ile Asn Cys Lys Ser Ser Gln Ser Val Leu Tyr Ser
             20                  25                  30

Pro Asn Gln Lys Asn Tyr Leu Val Trp Tyr Gln Gln Lys Pro Gly Gln
         35                  40                  45

Pro Pro Lys Leu Leu Leu Tyr Trp Ala Ser Ile Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Phe Thr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly

<210> SEQ ID NO 81
<211> LENGTH: 556
<212> TYPE: DNA
<213> ORGANISM: Homo sapiens

<400> SEQUENCE: 81
caggtccagc tggtacagtc tggggctgag gtgaagaagc ctggggcctc agtgaaggtc    60
tcctgcaagg tttccggata caccctcagt gaattatcca tgcactgggt gcgacaggct   120
cctggaaaag ggcttgagtg gatgggaggt tttgatcctg aagatgatga acaatctac    180 gcacagaagt tccagggcag agtcaccatg accgaggaca catctacaga cacagccttc   240
atggagctga gcagcctgag atctgaggac acggccgtgt attactgtgc aacccacgat   300
ttttggagtg gttattttca ctactggggc caggaaccc  tggtcaccgt ctcctcagct   360
tccaccaagg gcccatccgt cttccccctg gcgccctgct ccaggagcac ctccgagagc   420
```

```
acagccgccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagca                                                    556
```

<210> SEQ ID NO 82
<211> LENGTH: 185
<212> TYPE: PRT
<213> ORGANISM: Homo sapiens

<400> SEQUENCE: 82

```
Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Ser Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Asp Glu Thr Ile Tyr Ala Gln Lys Phe
    50                  55                  60

Gln Gly Arg Val Thr Met Thr Glu Asp Thr Ser Thr Asp Thr Ala Phe
65                  70                  75                  80

Met Glu Leu Ser Ser Leu Arg Ser Glu Asp Thr Ala Val Tyr Tyr Cys
                85                  90                  95

Ala Thr His Asp Phe Trp Ser Gly Tyr Phe His Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser
            180                 185
```

<210> SEQ ID NO 83
<211> LENGTH: 476
<212> TYPE: DNA
<213> ORGANISM: Homo sapiens

<400> SEQUENCE: 83

```
gacatcgtga tgacccagtc tccagactcc ctggctgtgt ctctgggcga gagggccacc    60
atcaactgca gtccagcca gagtgtttta tacagctccg acaataagag ctacttagtt    120
tggtaccagc agaaaccagg acagcctcct aaggtgctca tttactgggc atctattcgg    180
gaatccgggg tccctgaccg attcagtggc agcgggtctg ggacagattt cactctcacc    240
atcagcagcc tgcaggctga agatgtggca gtttattact gtcagcaata ttatactagt    300
ccgtggacgt tcggccaagg gaccaaggtg gaaatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgc       476
```

<210> SEQ ID NO 84
<211> LENGTH: 158
<212> TYPE: PRT

<400> SEQUENCE: 84

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asp Asn Lys Ser Tyr Leu Val Trp Tyr Gln Gln Lys Pro Gly Gln
        35                  40                  45

Pro Pro Lys Val Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn
145                 150                 155

<210> SEQ ID NO 85
<211> LENGTH: 543
<212> TYPE: DNA
<213> ORGANISM: Homo sapiens

<400> SEQUENCE: 85
caggtccagc tggtacagtc tggggctgag gtgaagaagc ctggggcctc agtgaaggtc    60
tcctgtaagg tttccggata caccctcact gaattatcca tgcactgggt gcgacaggct   120
cctggaaaag ggcttgagtg gatgggaggt tttgatcctg aagatggtga acaatctac    180
gcacagaagt tccagggcag agtcaccatg accgaggaca tctacagaca cacagcctac   240
atggagctga gcagcctgag atctgaggac acggccgtgt attactgtgc aatccacgag   300
ttttggagtg gttattttga ctactggggc cagggaaccc tggtcaccgt ctcttcagct   360
tccaccaagg gcccatccgt cttccccctg gcgccctgct ccaggagcac ctccgagagc   420
acagccgccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctt                                                                 543

<210> SEQ ID NO 86
<211> LENGTH: 181
<212> TYPE: PRT
<213> ORGANISM: Homo sapiens

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

```
Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Asp Thr Ala Tyr
 65                  70                  75                  80

Met Glu Leu Ser Ser Leu Arg Ser Glu Asp Thr Ala Val Tyr Tyr Cys
                    85                  90                  95

Ala Ile His Glu Phe Trp Ser Gly Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu
            180

<210> SEQ ID NO 87
<211> LENGTH: 477
<212> TYPE: DNA
<213> ORGANISM: Homo sapiens

<400> SEQUENCE: 87
gacatcgtga tgacccagtc tccagactcc ctggctgtgt ctctgggcga gagggccacc      60
atcaactgca gtccagcct gagtgtttta tacagctcca acaataagaa ctatttagtt     120
tggtaccttc agaaaccagg acagcctcct aagttgctca tttactgggc atctacccgg    180
gaatccgggg tccctgaccg attcagtggc agcgggtctg ggacagattt cactctcacc    240
atcagcagcc tgcaggccga agatgtggca gtttattact gtcagcaata ttatagttct    300
ccgtggacgt tcggccaagg gaccaaggtg gaaatcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgcc      477

<210> SEQ ID NO 88
<211> LENGTH: 159
<212> TYPE: PRT
<213> ORGANISM: Homo sapiens

<400> SEQUENCE: 88

Asp Ile Val Met Thr Gln Ser Pro Asp Ser Leu Ala Val Ser Leu Gly
 1               5                  10                  15

Glu Arg Ala Thr Ile Asn Cys Lys Ser Ser Leu Ser Val Leu Tyr Ser
                20                  25                  30

Ser Asn Asn Lys Asn Tyr Leu Val Trp Tyr Leu Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Ser Pro Trp Thr Phe Gly Gln Gly Thr Lys Val Glu Ile
            100                 105                 110
```

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala
145                 150                 155

<210> SEQ ID NO 89
<211> LENGTH: 1335
<212> TYPE: DNA
<213> ORGANISM: Homo sapiens

<400> SEQUENCE: 89

```
caggtccagc tggtacagtc tggggctgag gtgaagaagc tggggcctc agtgaaggtc      60
tcctgcaagg tttccggata caccctcact gaattatcca tgcactgggt gcgacagact    120
cctggaaaag ggcttgagtg gatgggaggt tttgatcctg aagatggtga acaatctac    180
gcacagaagt tccaggacag agtcaccatg accgaggaca tctacaga cacagcctac     240
atggaactga gcagcctgag atctgaggac acggccgtgt attactgtgc aacaaacgat   300
ttttggactg gttattatga ctactgggc cagggaaccc tggtcaccgt ctcctcagcc    360
tccaccaagg gcccatcggt cttccccctg gcgccctgct ccaggagcac ctccgagagc   420
acagcggccc tgggctgcct ggtcaaggac tacttcccg aaccggtgac ggtgtcgtgg    480
aactcaggcg ctctgaccag cggcgtgcac accttccag ctgtcctaca gtcctcagga   540
ctctactccc tcagcagcgt ggtgaccgtg ccctccagca cttcggcac ccagacctac    600
acctgcaacg tagatcacaa gcccagcaac accaaggtgg acaagacagt tgagcgcaaa   660
tgttgtgtcg agtgcccacc gtgcccagca ccacctgtgg caggaccgtc agtcttcctc   720
ttccccccaa aacccaagga caccctcatg atctcccgga cccctgaggt cacgtgcgtg   780
gtggtggacg tgagccacga agaccccgag gtccagttca actggtacgt ggacggcgtg   840
gaggtgcata atgccaagac aaagccacgg gaggagcagt tcaacagcac gttccgtgtg   900
gtcagcgtcc tcaccgttgt gcaccaggac tggctgaacg gcaaggagta caagtgcaag   960
gtctccaaca aaggcctccc agcccccatc gagaaaacca tctccaaaac caaagggcag  1020
cccc gagaac acaggtgta caccctgccc ccatcccggg aggagatgac caagaaccag  1080
gtcagcctga cctgcctggt caaaggcttc taccccagcg acatcgccgt ggagtgggag  1140
agcaatgggc agccggagaa caactacaag accacacctc ccatgctgga ctccgacggc  1200
tccttcttcc tctacagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gtaaa                                                   1335
```

<210> SEQ ID NO 90
<211> LENGTH: 445
<212> TYPE: PRT
<213> ORGANISM: Homo sapiens

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Thr Pro Gly Lys Gly Leu Glu Trp Met

```
                35                  40                  45
Gly Gly Phe Asp Pro Glu Asp Gly Glu Thr Ile Tyr Ala Gln Lys Phe
         50                  55                  60
Gln Asp Arg Val Thr Met Thr Glu Asp Thr Ser Thr Asp Thr Ala Tyr
 65                  70                  75                  80
Met Glu Leu Ser Ser Leu Arg Ser Glu Asp Thr Ala Val Tyr Tyr Cys
                 85                  90                  95
Ala Thr Asn Asp Phe Trp Thr Gly Tyr Tyr Asp Tyr Trp Gly Gln Gly
                100                 105                 110
Thr Leu Val Thr Val Ser Ser Ala Ser Thr Lys Gly Pro Ser Val Phe
                115                 120                 125
Pro Leu Ala Pro Cys Ser Arg Ser Thr Ser Glu Ser Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Asn Phe Gly Thr Gln Thr Tyr Thr Cys Asn Val Asp His Lys Pro
            195                 200                 205
Ser Asn Thr Lys Val Asp Lys Thr Val Glu Arg Lys Cys Cys Val Glu
        210                 215                 220
Cys Pro Pro Cys Pro Ala Pro Pro Val Ala Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Gln
                260                 265                 270
Phe Asn Trp Tyr Val Asp Gly Val Glu Val His Asn Ala Lys Thr Lys
            275                 280                 285
Pro Arg Glu Glu Gln Phe Asn Ser Thr Phe Arg Val Val Ser Val Leu
        290                 295                 300
Thr Val His Gln Asp Trp Leu Asn Gly Lys Glu Tyr Lys Cys Lys
305                 310                 315                 320
Val Ser Asn Lys Gly Leu Pro Ala Pro Ile Glu Lys Thr Ile Ser Lys
                325                 330                 335
Thr Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Met Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
            435                 440                 445

<210> SEQ ID NO 91
```

<211> LENGTH: 660
<212> TYPE: DNA
<213> ORGANISM: Homo sapiens

<400> SEQUENCE: 91

```
gacatcgtga tgacccagtc tccagactcc ctggctgtgt ctctgggcga gagggccacc      60
atcaactgca gtccagcca gagtgtttta tacagctcca acaataagaa ctacttagtt     120
tggtaccagc agaaaccagg acagcctcct aagacgctca tttactgggc atctacccgg    180
gaatccgggg tccctgaccg attcagtggc agcgggtctg ggacagattt cactctcacc    240
atcagcagcc tgcaggctga agatgtggga gtttattact gtcaacaata ttatactagt    300
ccgtggacgt tcggccaagg gaccaaggtg gaaatcaagc gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
```

<210> SEQ ID NO 92
<211> LENGTH: 220
<212> TYPE: PRT
<213> ORGANISM: Homo sapiens

<400> SEQUENCE: 92

```
Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Val Trp Tyr Gln Gln Lys Pro Gly Gln
         35                  40                  45

Pro Pro Lys Thr Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Gly Val Tyr Tyr Cys Gln Gln
                 85                  90                  95

Tyr Tyr Thr Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 93
<211> LENGTH: 560
<212> TYPE: DNA
<213> ORGANISM: Homo sapiens

<400> SEQUENCE: 93

```
caggtgcagc tgcaggagtc gggcccagga ctggtgaagc cgtcacagac cctgtccctc      60
acctgcactg tctctggtgg ctccatcagc agtggtggtt actactggag ctggatccgc     120
cagcacccag ggaagggcct ggagtggatt gggtacatct attacagtgg gagcacctac     180
tacaacccgt ccctcaagag tcgagttatc atatcagtag acacgtctaa gaaccagttc     240
tccctgaagc tgacctctgt gactgccgcg gacacggccg tgtattactg tgcgagatca     300
tatagcagct cgtccccact ggttcgaccc ctggggccag ggaaccctgg tcaccgtctc     360
ctcagcttcc accaagggcc catccgtctt ccccctggcg ccctgctcca ggagcacctc     420
cgagagcaca gccgccctgg gctgcctggt caaggactac ttccccgaac cggtgacggt     480
gtcgtggaac tcaggcgccc tgaccagcgg cgtgcacacc ttcccggctg tcctacagtc     540
ctcaggactc tactccctca                                                 560
```

<210> SEQ ID NO 94
<211> LENGTH: 186
<212> TYPE: PRT
<213> ORGANISM: Homo sapiens

<400> SEQUENCE: 94

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Ile Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Ser Tyr Ser Ser Ser Pro Leu Val Arg Pro Leu Gly
            100                 105                 110

Pro Gly Asn Pro Gly His Arg Leu Leu Ser Phe His Gln Gly Pro Ile
        115                 120                 125

Arg Leu Pro Pro Gly Ala Leu Leu Gln Glu His Leu Arg Glu His Ser
    130                 135                 140

Arg Pro Gly Leu Pro Gly Gln Gly Leu Leu Pro Arg Thr Gly Asp Gly
145                 150                 155                 160

Val Val Glu Leu Arg Arg Pro Asp Gln Arg Ala His Leu Pro Gly
                165                 170                 175

Cys Pro Thr Val Leu Arg Thr Leu Leu Pro
            180                 185

<210> SEQ ID NO 95
<211> LENGTH: 458
<212> TYPE: DNA
<213> ORGANISM: Homo sapiens

<400> SEQUENCE: 95

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccattcac tttcggccct   300
gggaccaaag tggatatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgc                           458
```

<210> SEQ ID NO 96
<211> LENGTH: 152
<212> TYPE: PRT
<213> ORGANISM: Homo sapiens

<400> SEQUENCE: 96

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn
145                 150
```

<210> SEQ ID NO 97
<211> LENGTH: 559
<212> TYPE: DNA
<213> ORGANISM: Homo sapiens

<400> SEQUENCE: 97

```
caggtccagc tggtacagtc tggggctgag gtgaagaagc ctgggcctc agtgaaggtc     60 tcctgcaagg tttccggata caccctcact gaattatcca tgcactgggt gcgacaggct   120
cctggaaaag ggcttgagtg gatgggaggt tttgatcctg aagatggtga acaatctac    180 gcacagaagt tccagggcag agtcaccatg accgaggaca catctacaga cacagcctac   240
atggagctga gcagcctgag atctgaggac acggccgtgt attactgtgc aacagatcgc   300
gagttttgga gtggttattt ctaccactgg ggccagggaa ccctggtcac cgtctcctca   360
gcctccacca agggcccatc ggtcttcccc ctggcgccct gctccaggag cacctccgag   420
agcacagcgg ccctgggctg cctggtcaag gactacttcc ccgaaccggt gacggtgtcg   480
tggaactcag gcgctctgac cagcggcgtg cacaccttcc cagctgtcct acagtcctca   540
```
ggactctact ccctcagca 559

<210> SEQ ID NO 98
<211> LENGTH: 186
<212> TYPE: PRT
<213> ORGANISM: Homo sapiens

<400> SEQUENCE: 98

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
             20                  25                  30

Ser Met His Trp Val Arg Gln Ala Pro Gly Lys Gly Leu Glu Trp Met
         35                  40                  45

Gly Gly Phe Asp Pro Glu Asp Gly Glu Thr Ile Tyr Ala Gln Lys Phe
     50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Asp Arg Glu Phe Trp Ser Gly Tyr Phe Tyr His Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser
            180                 185

<210> SEQ ID NO 99
<211> LENGTH: 491
<212> TYPE: DNA
<213> ORGANISM: Homo sapiens

<400> SEQUENCE: 99
gacatcgtga tgacccagtc tccagactcc ctggctgtgt ctctgggcga gagggccacc    60
atcaactgca agtccagcca gagtgtttta tacagctcca acaatgagaa cttcttagct   120
tggtaccagc agaaaccagg acagcctcct aaactgctca tttactgggc atctacccgg   180
gaatccgggg tcccagaccg cttcagtggc agcgggtctg ggacagattt cactctcacc   240
atcagcagcc tgcaggctga agatgtggca gtttattact gtcagcaata ttataatagt   300
ccgtggacgt tcggccaagg gaccaaggtg gaaatcaaac gaactgtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgcctcc   480
ccaatcgggt a                                                        491

<210> SEQ ID NO 100
<211> LENGTH: 163
<212> TYPE: PRT
<213> ORGANISM: Homo sapiens

<400> SEQUENCE: 100

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Glu Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Ser
145                 150                 155                 160

Pro Ile Gly

<210> SEQ ID NO 101
<211> LENGTH: 543
<212> TYPE: DNA
<213> ORGANISM: Homo sapiens

<400> SEQUENCE: 101
caggtccagc tggtacagtc tggggctgag gtgaagaagc ctggggcctc agtgaaggtc     60
tcctgcaagg tttccggata caccctcact gaattatcca tgcactgggt gcgacaggct    120
cctggaaaag ggcttgagtg gatgggaggt tttgatcctg aagatggtga acaatctac    180
gcacagaagt tccagggcag agtcaccatg accgaggaca tctacagaca cagcctac     240
atggagctga gcagcctgag atctgaggac acggccgtgt attactgtgc aacgacgat    300
ttttggagtg gttattttga ctactggggc cagggaaccc tggtcaccgt ctcctcagcc    360
tccaccaagg gcccatcggt cttccccctg gcgccctgct ccaggagcac tccgagagc    420
acagcggccc tgggctgcct ggtcaaggac tacttccccg aaccggtgac ggtgtcgtgg    480
aactcaggcg ctctgaccag cggcgtgcac accttcccag ctgtcctaca gtcctcagga    540
ctt                                                                  543

<210> SEQ ID NO 102
<211> LENGTH: 181
<212> TYPE: PRT
<213> ORGANISM: Homo sapiens

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

```
Gly Gly Phe Asp Pro Glu Asp Gly Glu Thr Ile Tyr Ala Gln Lys Phe
 50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Asp Asp Phe Trp Ser Gly Tyr Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu
            180

<210> SEQ ID NO 103
<211> LENGTH: 491
<212> TYPE: DNA
<213> ORGANISM: Homo sapiens

<400> SEQUENCE: 103
gacatcgtga tgacccagtc tccagactcc ctggctgtgt ctctgggcga gagggccacc      60
atcaactgca gtccagtca gagtgtttta tacaggtcta acaataagag ctacttagtt     120
tggtaccagc agaaactagg acagtctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattatt gtcaacaata ttatagtact     300
ccgtggacgt tcggccaagg gaccaaggtg gaaatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
ccaatcgggt a                                                         491

<210> SEQ ID NO 104
<211> LENGTH: 163
<212> TYPE: PRT
<213> ORGANISM: Homo sapiens

<400> SEQUENCE: 104

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Arg
                 20                  25                  30

Ser Asn Asn Lys Ser Tyr Leu Val Trp Tyr Gln Gln Lys Leu Gly Gln
             35                  40                  45

Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95
```

```
Tyr Tyr Ser Thr Pro Trp Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Pro Ile Gly

<210> SEQ ID NO 105
<211> LENGTH: 499
<212> TYPE: DNA
<213> ORGANISM: Homo sapiens

<400> SEQUENCE: 105
caggtccagc tggtacagtc tggggctgag gtgaagaagc ctggggcctc agtgaaggtc      60
tcctgcaagg tttccggata cccctcact gaattatcca tgcactgggt gcgacaggct     120
cctggaaaag ggcttgagtg gatgggaggt tttgatcctg aagatggtga acaatctac     180 gcacagaagt tccagggcag agtcaccatg accgaggaca tctacaga cacagcctac      240 atggagctga gcagcctgag atctgaggac acggccgtgt attactgtgc aacagacgat    300
ttttggagtg gttattttga ctactggggc cagggaaccc tggtcaccgt ctcctcagcc    360
tccaccaagg gcccatcggt cttccccctg gcgccctgct ccaggagcac tccgagagc    420 acagcggccc tgggctgcct ggtcaaggac tacttccccg aaccggtgac ggtgtcgtgg    480
aactcaggcg ctctgacca                                                 499

<210> SEQ ID NO 106
<211> LENGTH: 166
<212> TYPE: PRT
<213> ORGANISM: Homo sapiens

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Asp Phe Trp Ser Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr
```

<210> SEQ ID NO 107
<211> LENGTH: 448
<212> TYPE: DNA
<213> ORGANISM: Homo sapiens

<400> SEQUENCE: 107

```
gacatcgtga tgacccagtc tccagactcc ctggctgtgt ctctgggcga gagggccacc      60
atcaactgca gtccagcca gagtgtttta tacagctcca acaataagaa ctacttagtt     120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtcct    300
acgtggacgt tcggccaagg gaccaaggtg gaaatcaaac gaactgtggc tgcaccatct    360
gtcttcatct tcccgccatc tgatgagcag ttgaaatctg gaactgcctc tgttgtgtgc    420
ctgctgaata acttctatcc cagagagg                                       448
```

<210> SEQ ID NO 108
<211> LENGTH: 149
<212> TYPE: PRT
<213> ORGANISM: Homo sapiens

<400> SEQUENCE: 108

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Pro Thr Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu
145

<210> SEQ ID NO 109
<211> LENGTH: 540
<212> TYPE: DNA
<213> ORGANISM: Homo sapiens

<400> SEQUENCE: 109

```
caggtccagc tggtacagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcctg aagatggtga aacaatctac     180
gcacagaagt tccagggcag agtcaccatg accgaggaca catctacaga cacagcctac     240
```

```
atggagctga gcagcctgag atctgaggac acggccgtgt attactgtgc aacggacgat      300
ttttggagtg gttattttga ctactggggc cagggaaccc tggtcaccgt ctcctcagcc      360
tccaccaagg gcccatcggt cttccccctg gcgccctgct ccaggagcac tccgagagc       420 acagcggccc tgggctgcct ggtcaaggac tacttccccg aaccggtgac ggtgtcgtgg      480
aactcaggcg ctctgaccag cggcgtgcac accttcccag ctgtcctaca gtcctcagga     540
```

<210> SEQ ID NO 110
<211> LENGTH: 180
<212> TYPE: PRT
<213> ORGANISM: Homo sapiens

<400> SEQUENCE: 110

```
Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Asp Phe Trp Ser Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly
            180
```

<210> SEQ ID NO 111
<211> LENGTH: 478
<212> TYPE: DNA
<213> ORGANISM: Homo sapiens

<400> SEQUENCE: 111

```
gacatcgtga tgacccagtc tccagactcc ctggctgtgt ctctgggcga gagggccacc       60
atcaactgca gtccagcca gagtgtttta tacagctcca acaataagaa ctacttagct      120
tggtaccagc agaaaccagg acagcctcct aagctgctca tttactggac atctacccgg      180
gaatccgggg tccctgaccg attcagtggc agcgggtctg tgacagattt cactctcacc      240
atcagcagcc tgcaggctga agatgtggca gtttattact gtcagcaata ttatagttct      300
ccgtggacgt tcggccaagg gaccaaggtg gaaatcaaac gaactgtggc tgcaccatct     360
gtcttcatct tcccgccatc tgatgagcag ttgaaatctg gaactgcctc tgttgtgtgc      420
ctgctgaata acttctatcc cagagaggcc aaagtacagt ggaaggtgga taacgcct     478
```

<210> SEQ ID NO 112
<211> LENGTH: 159
<212> TYPE: PRT
<213> ORGANISM: Homo sapiens

<400> SEQUENCE: 112

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Thr Ser Thr Arg Glu Ser Gly Val
    50                  55                  60

Pro Asp Arg Phe Ser Gly Ser Gly Ser Val Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala
145                 150                 155

<210> SEQ ID NO 113
<211> LENGTH: 542
<212> TYPE: DNA
<213> ORGANISM: Homo sapiens

<400> SEQUENCE: 113
caggtccagc tggtacagtc tggggctgag gtgaagaagc ctggggcctc agtgaaggtc      60
tcctgcaagg tttccggata caccctcagt gaattatcca tgcactgggt gcgacaggct     120
cctggaaaag ggcttgagtg gatgggaggt tttgatcctg aagatggtga acaatctac     180 gcacagaagt tccagggcag agtcaccatg accgaggaca catctacaga cacagcctac     240
atggagctga gcagcctgag atctgaggac acggccgtgt tttactgtgc aacaaagagg     300
gaatatagtg gctactttga ctactgggc cagggaaccc tggtcaccgt ctcctcagcc      360
tccaccaagg gcccatcggt cttccccctg gcgccctgct ccaggagcac ctccgagagc     420
acagcggccc tgggctgcct ggtcaaggac tacttccccg aaccggtgac ggtgtcgtgg     480
aactcaggcg ctctgaccag cggcgtgcac accttcccag ctgtcctaca gtcctcagga     540
ct                                                                     542

<210> SEQ ID NO 114
<211> LENGTH: 180
<212> TYPE: PRT
<213> ORGANISM: Homo sapiens

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Ser Glu Leu
            20                  25                  30

-continued

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
 50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Phe Tyr Cys
                85                  90                  95

Ala Thr Lys Arg Glu Tyr Ser Gly Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly
            180

<210> SEQ ID NO 115
<211> LENGTH: 477
<212> TYPE: DNA
<213> ORGANISM: Homo sapiens

<400> SEQUENCE: 115
gacatcgtga tgacccagtc tccagactcc ctggctgtgt ctctgggcga gagggccacc     60
atcaactgca gtccagcca gagtgttta tacagctcca acagtaagaa ctacttagct     120
tggttccagc agaaaccagg acagcctcct aagctgctca tttactgggc atctacccgg    180
gaatccgggg tccctgaccg attcagtggc agcgggtctg ggacagattt cactctcacc    240
atcagccgcc tgcaggctga agatgtggca gtttattcct gtcagcaata ttttattact    300
ccgtggacgt tcggccaagg gaccaaggtg gaactcaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgcc        477

<210> SEQ ID NO 116
<211> LENGTH: 159
<212> TYPE: PRT
<213> ORGANISM: Homo sapiens

<400> SEQUENCE: 116

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Ser Lys Asn Tyr Leu Ala Trp Phe Gln Gln Lys Pro Gly Gln
            35                  40                  45

Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
65                  70                  75                  80

Ile Ser Arg Leu Gln Ala Glu Asp Val Ala Val Tyr Ser Cys Gln Gln

```
                    85                  90                  95
Tyr Phe Ile Thr Pro Trp Thr Phe Gly Gln Gly Thr Lys Val Glu Leu
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala
145                 150                 155
```

<210> SEQ ID NO 117
<211> LENGTH: 459
<212> TYPE: DNA
<213> ORGANISM: Homo sapiens

<400> SEQUENCE: 117

```
caggtgcagc tgagcagtc gggtccagga ctggtgaagc cctcgcagac cctctcactc      60
acctgtgcca tctccgggga cagtgtctct agcaacagtg ctgcttggaa ctggatcagg    120
cagtcccctt cgagaggcct tgagtggctg gaaggacat actacaggtc aagtggtat     180
agtgatcatg cagtatctgt gagaagtcga ataaccatct acccagacac atccaagaac   240
cagttctccc tgcagctgaa ctctgtgact cccgaggaca cggctgtgta ttactgtgca   300
agagatcgga ttagtgggac ctatgtcggt atggacgtct ggggccaagg gaccacggtc   360
accgtctcct cagcctccac caagggccca tcggtcttcc ccctggcgcc cctgctccag   420
gagcacctcc gagagcacag cggccctggg ctgcctggc                          459
```

<210> SEQ ID NO 118
<211> LENGTH: 153
<212> TYPE: PRT
<213> ORGANISM: Homo sapiens

<400> SEQUENCE: 118

```
Gln Val Gln Pro Glu Gln Ser Gly Pro Gly Leu Val Lys Pro Ser Gln
1               5                   10                  15
Thr Leu Ser Leu Thr Cys Ala Ile Ser Gly Asp Ser Val Ser Ser Asn
            20                  25                  30
Ser Ala Ala Trp Asn Trp Ile Arg Gln Ser Pro Ser Arg Gly Leu Glu
        35                  40                  45
Trp Leu Gly Arg Thr Tyr Tyr Arg Ser Lys Trp Tyr Ser Asp His Ala
    50                  55                  60
Val Ser Val Arg Ser Arg Ile Thr Ile Tyr Pro Asp Thr Ser Lys Asn
65                  70                  75                  80
Gln Phe Ser Leu Gln Leu Asn Ser Val Thr Pro Glu Asp Thr Ala Val
                85                  90                  95
Tyr Tyr Cys Ala Arg Asp Arg Ile Ser Gly Thr Tyr Val Gly Met Asp
            100                 105                 110
Val Trp Gly Gln Gly Thr Thr Val Thr Val Ser Ser Ala Ser Thr Lys
        115                 120                 125
Gly Pro Ser Val Phe Pro Leu Ala Pro Leu Leu Gln Glu His Leu Arg
    130                 135                 140
Glu His Ser Gly Pro Gly Leu Pro Gly
145                 150
```

<210> SEQ ID NO 119
<211> LENGTH: 526

<210> SEQ ID NO 119
<211> LENGTH: 526
<212> TYPE: DNA
<213> ORGANISM: Homo sapiens

<400> SEQUENCE: 119

| | | | | | |
|---|---|---|---|---|---|
| ccagctcagc | tcctggggct | gctaatgctc | tgggtccctg | gatccaatga | ggatattgtg | 60 |
| atgacccaga | ctccactctc | cctgcccgtc | acccctggag | agccggcctc | catctcctgc | 120 |
| aggtctagtc | agagcctctt | ggatagtgat | gatggaaaca | cctatttgga | ctggtacctg | 180 |
| cagaagccag | ggcagtctcc | acagctcctg | atctatacgc | tttcctttcg | ggcctctgga | 240 |
| gtcccagaca | ggttcagtgg | cagtgggtca | ggcactgatt | tcacactgac | aatcagcagg | 300 |
| gtggaggctg | aggatgttgg | agtttattac | tgcatgcaac | gtatagagtt | tcctctcact | 360 |
| ttcggcggag | ggaccaaggt | ggagatcaaa | cgaactgtgg | ctgcaccatc | tgtcttcatc | 420 |
| ttcccgccat | ctgatgagca | gttgaaatct | ggaactgcct | ctgttgtgtg | cctgctgaat | 480 |
| aacttctatc | ccagagaggc | caaagtacag | tggaaggtgg | ataacg | | 526 |

<210> SEQ ID NO 120
<211> LENGTH: 175
<212> TYPE: PRT
<213> ORGANISM: Homo sapiens

<400> SEQUENCE: 120

Pro Ala Gln Leu Leu Gly Leu Leu Met Leu Trp Val Pro Gly Ser Asn
1               5                   10                  15

Glu Asp Ile Val Met Thr Gln Thr Pro Leu Ser Leu Pro Val Thr Pro
            20                  25                  30

Gly Glu Pro Ala Ser Ile Ser Cys Arg Ser Ser Gln Ser Leu Leu Asp
        35                  40                  45

Ser Asp Asp Gly Asn Thr Tyr Leu Asp Trp Tyr Leu Gln Lys Pro Gly
    50                  55                  60

Gln Ser Pro Gln Leu Leu Ile Tyr Thr Leu Ser Phe Arg Ala Ser Gly
65                  70                  75                  80

Val Pro Asp Arg Phe Ser Gly Ser Gly Ser Gly Thr Asp Phe Thr Leu
                85                  90                  95

Thr Ile Ser Arg Val Glu Ala Glu Asp Val Gly Val Tyr Tyr Cys Met
            100                 105                 110

Gln Arg Ile Glu Phe Pro Leu Thr Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn
                165                 170                 175

<210> SEQ ID NO 121
<211> LENGTH: 499
<212> TYPE: DNA
<213> ORGANISM: Homo sapiens

<400> SEQUENCE: 121

| | | | | | |
|---|---|---|---|---|---|
| caggtccagg | tggtacagtc | tggggctgag | gtgaagaacc | ctggggcctc | agtgaaggtc | 60 |
| tcctgcaagg | tttccggatc | caccctcact | gaattatcca | tgcactgggt | gcgacaggct | 120 |
| cctggaaaag | ggcttgagtg | gatgggaggt | tttgatcctg | aagatggtga | aacaatctac | 180 |
| gcacagaagt | tccagggcag | agtcaccatg | accgaggaca | catctacaga | cacagtctac | 240 |

```
atggagctga gcagcctgag atctgaggac acggccgtgt attactgtgc aaccaacgat      300
ttttggagtg gttattttga ctactggggc cagggaaccc tggtcaccgt ctcctcagcc      360
tccaccaagg gcccatcggt cttccccctg gcgccctgct ccaggagcac ctccgagagc      420
acagcggccc tgggctgcct ggtcaaggac tacttccccg aaccggtgac ggtgtcgtgg      480
aactcaggcg ctctgacca                                                   499

<210> SEQ ID NO 122
<211> LENGTH: 166
<212> TYPE: PRT
<213> ORGANISM: Homo sapiens

<400> SEQUENCE: 122

Gln Val Gln Val Val Gln Ser Gly Ala Glu Val Lys Asn Pro Gly Ala
 1               5                  10                  15

Ser Val Lys Val Ser Cys Lys Val Ser Gly Ser Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Val Tyr
65                  70                  75                  80

Met Glu Leu Ser Ser Leu Arg Ser Glu Asp Thr Ala Val Tyr Tyr Cys
                85                  90                  95

Ala Thr Asn Asp Phe Trp Ser Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr
                165

<210> SEQ ID NO 123
<211> LENGTH: 536
<212> TYPE: DNA
<213> ORGANISM: Homo sapiens

<400> SEQUENCE: 123
caggtcttca tttctctgtt gctctggatc tctgatgtct atgggacat cgtgatgacc       60 cagtctccag actccctggc tgtgtctctg ggcgagaggg ccaccatcac ctgcaagtcc      120
agccagactg ttttatacag ctccaacaat aagaactact agtttggta tcagcagaaa      180 tcaggacagc ctcctaagct gctcattcac tgggcatcta ccgggaatc ggggtccct       240 gaccgattca gtggcagcgg gtctgggaca gatttcacgc tcaccatcag cagcctgcag      300
gctgaagatg tggcagttta ttactgtcag caatattata gtagtccgtg acgttcggc      360 caagggacca aggtggaaat caaacgaact gtggctgcac catctgtctt catcttcccg      420
ccatctgatg agcagttgaa atctggaact gcctctgttg tgtgcctgct gaataacttc      480
tatcccagag aggccaaagt acagtggaag gtggataacg cccttccaat cgggta         536
```

<210> SEQ ID NO 124
<211> LENGTH: 178
<212> TYPE: PRT
<213> ORGANISM: Homo sapiens

<400> SEQUENCE: 124

```
Gln Val Phe Ile Ser Leu Leu Leu Trp Ile Ser Asp Val Tyr Gly Asp
1               5                   10                  15

Ile Val Met Thr Gln Ser Pro Asp Ser Leu Ala Val Ser Leu Gly Glu
            20                  25                  30

Arg Ala Thr Ile Thr Cys Lys Ser Ser Gln Thr Val Leu Tyr Ser Ser
        35                  40                  45

Asn Asn Lys Asn Tyr Leu Val Trp Tyr Gln Gln Lys Ser Gly Gln Pro
    50                  55                  60

Pro Lys Leu Leu Ile His Trp Ala Ser Ile Arg Glu Ser Gly Val Pro
65                  70                  75                  80

Asp Arg Phe Ser Gly Ser Gly Ser Gly Thr Asp Phe Thr Leu Thr Ile
                85                  90                  95

Ser Ser Leu Gln Ala Glu Asp Val Ala Val Tyr Tyr Cys Gln Gln Tyr
            100                 105                 110

Tyr Ser Pro Trp Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Pro
                165                 170                 175

Ile Gly
```

<210> SEQ ID NO 125
<211> LENGTH: 414
<212> TYPE: DNA
<213> ORGANISM: Homo sapiens

<400> SEQUENCE: 125

```
caggtgcagg ctgagcagtc gggtccagga ctggtgaagc cctcgcagac cctctcactc      60
acctgtgcca tctccgggga cagtgtctct agctacagtg ctgcttggaa ctggatcagg     120
cagtcccctt cgagaggcct tgagtggctg gaaggacat actacaggtc caagtggtat      180
agtgatcatg cagtatctgt gagaagtcga ataaccatct cccagacac atccaagaac     240
cagttctccc tgcagctgaa ctctgtgact cccgaggaca cggctgtgta ttactgtgca     300
agagatcgga ttagtgggac ctatgtcggt atggacgtct ggggccaagg gaccacggtc     360
accgtctcct cagcctccac caagggcccc atcggtcttc cccctggccc cctc           414
```

<210> SEQ ID NO 126
<211> LENGTH: 138
<212> TYPE: PRT
<213> ORGANISM: Homo sapiens

<400> SEQUENCE: 126

```
Gln Val Gln Ala Glu Gln Ser Gly Pro Gly Leu Val Lys Pro Ser Gln
1               5                   10                  15

Thr Leu Ser Leu Thr Cys Ala Ile Ser Gly Asp Ser Val Ser Ser Tyr
            20                  25                  30

Ser Ala Ala Trp Asn Trp Ile Arg Gln Ser Pro Ser Arg Gly Leu Glu
```

```
                35                  40                  45
Trp Leu Gly Arg Thr Tyr Tyr Arg Ser Lys Trp Tyr Ser Asp His Ala
     50                  55                  60

Val Ser Val Arg Ser Arg Ile Thr Ile Tyr Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Asp Arg Ile Ser Gly Thr Tyr Val Gly Met Asp
                100                 105                 110

Val Trp Gly Gln Gly Thr Thr Val Thr Val Ser Ser Ala Ser Thr Lys
            115                 120                 125

Gly Pro Ile Gly Leu Pro Pro Gly Pro Leu
        130                 135

<210> SEQ ID NO 127
<211> LENGTH: 514
<212> TYPE: DNA
<213> ORGANISM: Homo sapiens

<400> SEQUENCE: 127
gtcttcattt ctctgttgct ctggatctct ggtgcctacg ggacatcgt gatgacccag      60 tctccagact ccctggctgt gtctctgggc gagagggcca ccatcaactg caagtccagc     120
cagagtgttt tatacagttc caacaataag aactacatag tttggtacca gcagaaacca    180
gggcagcctc ctaagttgct catttactgg acatctaccc gggaatccgg ggtccctgac    240
cgattcagtg gcagcgggtc tgggacagat ttcactctca ctatcagtag cctgcaggct    300
gaagatgtgg cagtttatta ctgtcagcaa tatttagtt ctccgtggac gttcggccaa     360
gggaccaaag tggacatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gata                                514

<210> SEQ ID NO 128
<211> LENGTH: 171
<212> TYPE: PRT
<213> ORGANISM: Homo sapiens

<400> SEQUENCE: 128

Val Phe Ile Ser Leu Leu Trp Ile Ser Gly Ala Tyr Gly Asp Ile
  1               5                  10                  15

Val Met Thr Gln Ser Pro Asp Ser Leu Ala Val Ser Leu Gly Glu Arg
             20                  25                  30

Ala Thr Ile Asn Cys Lys Ser Ser Gln Ser Val Leu Tyr Ser Ser Asn
         35                  40                  45

Asn Lys Asn Tyr Ile Val Trp Tyr Gln Gln Lys Pro Gly Gln Pro Pro
     50                  55                  60

Lys Leu Leu Ile Tyr Trp Thr Ser Thr Arg Glu Ser Gly Val Pro Asp
 65                  70                  75                  80

Arg Phe Ser Gly Ser Gly Ser Gly Thr Asp Phe Thr Leu Thr Ile Ser
                 85                  90                  95

Ser Leu Gln Ala Glu Asp Val Ala Val Tyr Tyr Cys Gln Gln Tyr Phe
            100                 105                 110

Ser Ser Pro Trp Thr Phe Gly Gln Gly Thr Lys Val Asp Ile Lys Arg
            115                 120                 125

Thr Val Ala Ala Pro Ser Val Phe Ile Phe Pro Pro Ser Asp Glu Gln
```

```
                 130                 135                 140
Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp
                165                 170
```

<210> SEQ ID NO 129
<211> LENGTH: 444
<212> TYPE: DNA
<213> ORGANISM: Homo sapiens

<400> SEQUENCE: 129

```
cagtcgggtc caggactggt gaagccctcg cagaccctct cactcacctg tgccatctcc     60
ggggacagtg tctctagcaa cagtgctgct tggaactgga tcaggcagtc cccttcgaga    120
ggccttgagt ggctgggaag gacatactac aggtccaagt ggtatagtga tcatgcagta    180
tctgtgagaa gtcgaataac catctaccca gacacatcca agaaccagtt ctccctgcag    240
ctgaactctg tgactcccga ggacacggct gtgtattact gtgcaagaga tcggattagt    300
gggacctatg tcggtatgga cgtctggggc caagggacca cggtcaccgt ctcctcagcc    360
tccaccaagg gcccatcggt cttccccctg gcgccctgc tccaggagca cctccgagag     420
cacagcggcc ctgggctgcc tggc                                           444
```

<210> SEQ ID NO 130
<211> LENGTH: 148
<212> TYPE: PRT
<213> ORGANISM: Homo sapiens

<400> SEQUENCE: 130

```
Gln Ser Gly Pro Gly Leu Val Lys Pro Ser Gln Thr Leu Ser Leu Thr
  1               5                  10                  15

Cys Ala Ile Ser Gly Asp Ser Val Ser Ser Asn Ser Ala Ala Trp Asn
             20                  25                  30

Trp Ile Arg Gln Ser Pro Ser Arg Gly Leu Glu Trp Leu Gly Arg Thr
         35                  40                  45

Tyr Tyr Arg Ser Lys Trp Tyr Ser Asp His Ala Val Ser Val Arg Ser
     50                  55                  60

Arg Ile Thr Ile Tyr Pro Asp Thr Ser Lys Asn Gln Phe Ser Leu Gln
 65                  70                  75                  80

Leu Asn Ser Val Thr Pro Glu Asp Thr Ala Val Tyr Tyr Cys Ala Arg
                 85                  90                  95

Asp Arg Ile Ser Gly Thr Tyr Val Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Leu Leu Gln Glu His Leu Arg Glu His Ser Gly Pro
    130                 135                 140

Gly Leu Pro Gly
145
```

<210> SEQ ID NO 131
<211> LENGTH: 505
<212> TYPE: DNA
<213> ORGANISM: Homo sapiens

<400> SEQUENCE: 131

```
gggctgctaa tgctctggat acctggatcc agtgcagata ttgggatgac ccagactcca     60
```

-continued

```
ctctctctgt ccgtcacccc tggacagccg gcctccatct cctgtaagtc tagtcagagc    120
ctcctgtata gtgatggaaa gacctatttg tattggtacc tgcagaagcc aggccagcct    180
ccacaacacc tgatctatga agtttccaac cggttctctg gagtgccaga taggttcagt    240
ggcagcgggt ctgggacaga tttcacactg aaaatcagcc gggtggaggc tgatgatgtt    300
ggggtttatt actgcatgca aactatacac cttccgctca ctttcggcgg agggaccaag    360
gtggagatcc aacgaactgt ggctgcacca tctgtcttca tcttcccgcc atctgatgag    420
cagttgaaat ctggaactgc ctctgttgtg tgcctgctga ataacttcta tcccagagag    480
gccaaagtac agtggaaggt ggata                                           505
```

<210> SEQ ID NO 132
<211> LENGTH: 168
<212> TYPE: PRT
<213> ORGANISM: Homo sapiens

<400> SEQUENCE: 132

```
Gly Leu Leu Met Leu Trp Ile Pro Gly Ser Ser Ala Asp Ile Gly Met
 1               5                  10                  15

Thr Gln Thr Pro Leu Ser Leu Ser Val Thr Pro Gly Gln Pro Ala Ser
             20                  25                  30

Ile Ser Cys Lys Ser Ser Gln Ser Leu Leu Tyr Ser Asp Gly Lys Thr
         35                  40                  45

Tyr Leu Tyr Trp Tyr Leu Gln Lys Pro Gly Gln Pro Pro Gln His Leu
     50                  55                  60

Ile Tyr Glu Val Ser Asn Arg Phe Ser Gly Val Pro Asp Arg Phe Ser
 65                  70                  75                  80

Gly Ser Gly Ser Gly Thr Asp Phe Thr Leu Lys Ile Ser Arg Val Glu
                 85                  90                  95

Ala Asp Asp Val Gly Val Tyr Tyr Cys Met Gln Thr Ile His Leu Pro
            100                 105                 110

Leu Thr Phe Gly Gly Gly Thr Lys Val Glu Ile Gln Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp
                165
```

<210> SEQ ID NO 133
<211> LENGTH: 447
<212> TYPE: DNA
<213> ORGANISM: Homo sapiens

<400> SEQUENCE: 133

```
gagcagtcgg gtccaggact ggtgaagccc tcgcagaccc tctcactcac ctgtgccatc     60
tccggggaca gtgtctctag caacagtgct gcttggaact ggatcaggca gtccccttcg    120
agaggccttg agtggctggg aaggacatac tacaggtcca agtggtatag tgatcatgca    180
gtatctgtga aagtcgaat aaccatctac ccagacacat ccaagaacca gttctccctg    240
cagctgaact ctgtgactcc cgaggacacg gctgtgtatt actgtgcaag agatcggatt    300
agtgggacct atgtcggtat ggacgtctgg ggccaaggga ccacggtcac cgtctcctca    360
gcctccacca agggcccatc ggtcttcccc ctggcgcccc tgctccagga gcacctccga    420
```
gagcacagcg gccctgggct gcctggc 447

<210> SEQ ID NO 134
<211> LENGTH: 149
<212> TYPE: PRT
<213> ORGANISM: Homo sapiens

<400> SEQUENCE: 134

Glu Gln Ser Gly Pro Gly Leu Val Lys Pro Ser Gln Thr Leu Ser Leu
1               5                   10                  15

Thr Cys Ala Ile Ser Gly Asp Ser Val Ser Ser Asn Ser Ala Ala Trp
            20                  25                  30

Asn Trp Ile Arg Gln Ser Pro Ser Arg Gly Leu Glu Trp Leu Gly Arg
        35                  40                  45

Thr Tyr Tyr Arg Ser Lys Trp Tyr Ser Asp His Ala Val Ser Val Arg
    50                  55                  60

Ser Arg Ile Thr Ile Tyr Pro Asp Thr Ser Lys Asn Gln Phe Ser Leu
65                  70                  75                  80

Gln Leu Asn Ser Val Thr Pro Glu Asp Thr Ala Val Tyr Tyr Cys Ala
                85                  90                  95

Arg Asp Arg Ile Ser Gly Thr Tyr Val Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Leu Leu Gln Glu His Leu Arg Glu His Ser Gly
    130                 135                 140

Pro Gly Leu Pro Gly
145

<210> SEQ ID NO 135
<211> LENGTH: 520
<212> TYPE: DNA
<213> ORGANISM: Homo sapiens

<400> SEQUENCE: 135
caggtcttca tttctctgtt gctctggatc tctggtgcct acggggacat cgtgatgacc      60
cagtctccag actccctggc tgtgtctctg ggcgagaggg ccgccatcaa ctgcaagtcc     120
agccagactg tttttataca gctccaacaat aagaactact ggtttggta ccagcagaaa     180 ccaggacagc ctcccaagct gctcatttac tgggcatcta cccgggaatc cggggtccct     240
gaccgattca gtggcagcgg gtctgggaca gatttcactc tcaccatcag cagcctgcag     300
gctgaagatg tggcagttta ttactgtcaa caatattata aaagtccgtg acgttcggc      360 caagggacca aggtggaaat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg                           520

<210> SEQ ID NO 136
<211> LENGTH: 173
<212> TYPE: PRT
<213> ORGANISM: Homo sapiens

<400> SEQUENCE: 136

Gln Val Phe Ile Ser Leu Leu Leu Trp Ile Ser Gly Ala Tyr Gly Asp
1               5                   10                  15

Ile Val Met Thr Gln Ser Pro Asp Ser Leu Ala Val Ser Leu Gly Glu

```
                        20                  25                  30
Arg Ala Ala Ile Asn Cys Lys Ser Ser Gln Thr Val Leu Tyr Ser Ser
                35                  40                  45

Asn Asn Lys Asn Tyr Leu Val Trp Tyr Gln Gln Lys Pro Gly Gln Pro
         50                  55                  60

Pro Lys Leu Leu Ile Tyr Trp Ala Ser Thr Arg Glu Ser Gly Val Pro
 65                  70                  75                  80

Asp Arg Phe Ser Gly Ser Gly Ser Gly Thr Asp Phe Thr Leu Thr Ile
                 85                  90                  95

Ser Ser Leu Gln Ala Glu Asp Val Ala Val Tyr Tyr Cys Gln Gln Tyr
            100                 105                 110

Tyr Lys Ser Pro Trp Thr Phe Gly Gln Gly Thr Lys Val Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn
                165                 170

<210> SEQ ID NO 137
<211> LENGTH: 490
<212> TYPE: DNA
<213> ORGANISM: Homo sapiens

<400> SEQUENCE: 137
caggtccagc tggtacagtc tggggctgag gtgaagaagc ctggggcctc agtgaaggtc        60
tcctgcaagg tttccggata caccctcact gaattatcca tgcactgggt gcgacaggct       120
cctggaaaag ggcttgagtg gatgggaggt tttgatcctg aaaatggtga acaatccac        180 gcacagaagt tccagggcag agtcatcatg accgaggaca catctacaga cacagcctac       240
atggagctga gcagcctgag atctgaggac acggccgtgt attactgtgc aacagatcag       300
ggtggatata gtggctactt tgactgctgg ggccagggaa ccctggtcac cgtctcctca       360
gcttccacca agggcccatc cgtcttcccc ctggcgccct gctccaggag cacctccgag       420
agcacagccg ccctgggctg cctggtcaag gactacttcc ccgaaccggt gacggtgtcg       480
tggaactcag                                                               490

<210> SEQ ID NO 138
<211> LENGTH: 163
<212> TYPE: PRT
<213> ORGANISM: Homo sapiens

<400> SEQUENCE: 138

Gln Val Gln Leu Val Gln Ser Gly Ala Glu Val Lys Lys Pro Gly Ala
  1               5                  10                  15

Ser Val Lys Val Ser Cys Lys Val Ser Gly Tyr Thr Leu Thr Glu Leu
             20                  25                  30

Ser Met His Trp Val Arg Gln Ala Pro Gly Lys Gly Leu Glu Trp Met
         35                  40                  45

Gly Gly Phe Asp Pro Glu Asn Gly Glu Thr Ile His Ala Gln Lys Phe
     50                  55                  60

Gln Gly Arg Val Ile Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
```

```
              85                  90                  95
Ala Thr Asp Gln Gly Gly Tyr Ser Gly Tyr Phe Asp Cys Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
            130                 135                 140
Leu Gly Cys Leu Val Lys Asp Tyr Phe Pro Glu Pro Val Thr Val Ser
145                 150                 155                 160
Trp Asn Ser
```

<210> SEQ ID NO 139
<211> LENGTH: 540
<212> TYPE: DNA
<213> ORGANISM: Homo sapiens

<400> SEQUENCE: 139

```
agacccaggt cttcatttct ctgttgctct ggatctctgg tgcctacggg gacatcgtga    60
tgacccagtc tccagactcc ctggctgtgt ctctgggcga gagggccacc atcaactgca   120
agtccagcca gagtatttta tacagctcca ataataagaa ttatttagtt tggtaccagc   180
agaaaccagg acagcctcct aagttgctca tttactgggc atctacccgg gaatccgggg   240
tccctgaccg attcagtggc agcgggtctg gacagatttc actctcacc atcagcagcc    300
tgcaggctga agatgtggca gtttattact gtcagcaata ttatagtagt cctccgacgt   360
tcggccaagg gaccaaggtg gaaatcaaac gaactgtggc tgcaccatct gtcttcatct   420
tcccgccatc tgatgagcag ttgaaatctg gaactgcctc tgttgtgtgc ctgctgaata   480
acttctatcc cagagaggcc aaagtacagt ggaaggtgga taacgccctc caatcgggta   540
```

<210> SEQ ID NO 140
<211> LENGTH: 179
<212> TYPE: PRT
<213> ORGANISM: Homo sapiens

<400> SEQUENCE: 140

```
Thr Gln Val Phe Ile Ser Leu Leu Leu Trp Ile Ser Gly Ala Tyr Gly
1               5                  10                  15
Asp Ile Val Met Thr Gln Ser Pro Asp Ser Leu Ala Val Ser Leu Gly
            20                  25                  30
Glu Arg Ala Thr Ile Asn Cys Lys Ser Ser Gln Ser Ile Leu Tyr Ser
            35                  40                  45
Ser Asn Asn Lys Asn Tyr Leu Val Trp Tyr Gln Gln Lys Pro Gly Gln
        50                  55                  60
Pro Pro Lys Leu Leu Ile Tyr Trp Ala Ser Thr Arg Glu Ser Gly Val
65                  70                  75                  80
Pro Asp Arg Phe Ser Gly Ser Gly Ser Gly Thr Asp Phe Thr Leu Thr
                85                  90                  95
Ile Ser Ser Leu Gln Ala Glu Asp Val Ala Val Tyr Tyr Cys Gln Gln
            100                 105                 110
Tyr Tyr Ser Ser Pro Pro Thr Phe Gly Gln Gly Thr Lys Val Glu Ile
            115                 120                 125
Lys Arg Thr Val Ala Ala Pro Ser Val Phe Ile Phe Pro Pro Ser Asp
            130                 135                 140
Glu Gln Leu Lys Ser Gly Thr Ala Ser Val Val Cys Leu Leu Asn Asn
145                 150                 155                 160
```

Phe Tyr Pro Arg Glu Ala Lys Val Gln Trp Lys Val Asp Asn Ala Leu
            165                 170                 175

Gln Ser Gly

<210> SEQ ID NO 141
<211> LENGTH: 518
<212> TYPE: DNA
<213> ORGANISM: Homo sapiens

<400> SEQUENCE: 141
accatggagt ggacctggag ggtcctcttc ttggtggcag cagctacagg cacccacgcc      60
caggtccagc tggtacagtc tggggctgag gtgaagaagc ctggggcctc agtgaaggtc     120
tcctgcaagg tttccggata caccctcact gaattatcca tgcactgggt gcgacaggct     180
cctggaaaag gcttgagtg gatgggaggt tttgatcctg aagatggtga acaatctac      240 gcacagaagt tccagggcag agtcaccatg accgaggaca catctacaga cacagcctac     300
atggagctga gtagcctgag aactgaggac acggccgtgt attactgtac aacggacgat     360
ttttggagtg gttatttga ctactggggc cagggaaccc tggtcaccgt ctcctcagcc     420
tccaccaagg gcccatcggt cttccccctg gcgccctgct ccaggagcac ctccgagagc     480
acagcggcct gggctgcctg gtcaaggact acttcccc                              518

<210> SEQ ID NO 142
<211> LENGTH: 172
<212> TYPE: PRT
<213> ORGANISM: Homo sapiens

<400> SEQUENCE: 142

Thr Met Glu Trp Thr Trp Arg Val Leu Phe Leu Val Ala Ala Ala Thr
  1               5                  10                  15

Gly Thr His Ala Gln Val Gln Leu Val Gln Ser Gly Ala Glu Val Lys
             20                  25                  30

Lys Pro Gly Ala Ser Val Lys Val Ser Cys Lys Val Ser Gly Tyr Thr
         35                  40                  45

Leu Thr Glu Leu Ser Met His Trp Val Arg Gln Ala Pro Gly Lys Gly
 50                  55                  60

Leu Glu Trp Met Gly Gly Phe Asp Pro Glu Asp Gly Glu Thr Ile Tyr
 65                  70                  75                  80

Ala Gln Lys Phe Gln Gly Arg Val Thr Met Thr Glu Asp Thr Ser Thr
                 85                  90                  95

Asp Thr Ala Tyr Met Glu Leu Ser Ser Leu Arg Thr Glu Asp Thr Ala
            100                 105                 110

Val Tyr Tyr Cys Thr Thr Asp Asp Phe Trp Ser Gly Tyr Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Trp Ala Ala Trp Ser Arg Thr Thr Ser
                165                 170

<210> SEQ ID NO 143
<211> LENGTH: 519
<212> TYPE: DNA
<213> ORGANISM: Homo sapiens

<400> SEQUENCE: 143

```
caggtcttca tttctctgtt gctctggatc tctggtgcct acggggacat cgtgatgacc      60
cagtctccag actccctggc tgtgtctctg ggcgagaggg ccaccatcaa ctgcaagtcc     120
agccagagtc ttttatacag ctccaaaaat aagaactatt tagtttggta ccagcagaaa     180
ccaggacagc ctccaaagct gctcattaac tgggcatcta cccgggaatc cggggtccct     240
gaccgattca gtggcagcgg gtctgggaca gatttcactc tcaccatcag cagcctgcag     300
gctgaagatg tggcagttta ttactgtcag caatattata gttctccgtg gacgttcggc     360
caagggacca aggtggaaat caaacgaact gtggctgcac catctgtctt catcttcccg     420
ccatctgatg agcagttgaa atctggaact gcctctgttg tgtgcctgct gaataacttc     480
tatcccagag aggcaaagta cagtggaagg tggatacgc                            519
```

<210> SEQ ID NO 144
<211> LENGTH: 173
<212> TYPE: PRT
<213> ORGANISM: Homo sapiens

<400> SEQUENCE: 144

```
Gln Val Phe Ile Ser Leu Leu Trp Ile Ser Gly Ala Tyr Gly Asp
  1               5                  10                  15
Ile Val Met Thr Gln Ser Pro Asp Ser Leu Ala Val Ser Leu Gly Glu
             20                  25                  30
Arg Ala Thr Ile Asn Cys Lys Ser Ser Gln Ser Leu Leu Tyr Ser Ser
         35                  40                  45
Lys Asn Lys Asn Tyr Leu Val Trp Tyr Gln Gln Lys Pro Gly Gln Pro
     50                  55                  60
Pro Lys Leu Leu Ile Asn Trp Ala Ser Thr Arg Glu Ser Gly Val Pro
 65                  70                  75                  80
Asp Arg Phe Ser Gly Ser Gly Ser Gly Thr Asp Phe Thr Leu Thr Ile
                 85                  90                  95
Ser Ser Leu Gln Ala Glu Asp Val Ala Val Tyr Tyr Cys Gln Gln Tyr
            100                 105                 110
Tyr Ser Ser Pro Trp Thr Phe Gly Gln Gly Thr Lys Val Glu Ile Lys
        115                 120                 125
Arg Thr Val Ala Ala Pro Ser Val Phe Ile Phe Pro Pro Ser Asp Glu
    130                 135                 140
Gln Leu Lys Ser Gly Thr Ala Ser Val Val Cys Leu Leu Asn Asn Phe
145                 150                 155                 160
Tyr Pro Arg Glu Ala Lys Tyr Ser Gly Arg Trp Ile Arg
                165                 170
```

<210> SEQ ID NO 145
<211> LENGTH: 436
<212> TYPE: DNA
<213> ORGANISM: Homo sapiens

<400> SEQUENCE: 145

```
gagcagtcgg ggggaggcgt ggtccagcct gggaggtccc tgagactctc ctgtgcagcg      60
tctggattca ccttcagtag ctatggcatg cactgggtcc gccaggctcc aggcaagggg     120
ctggagtggg tggcagttat atggtatgat ggaaataata atactatgc agactccgtg     180
aagggccgat tcaccatctc cagagacact tccaagaaca cgctatatct gcaaatgaac     240
agcctgagag ccgaggacac ggctgtgtat tactgtgcga gagatagcag ctcgtactac     300
```

```
tactacggta tggacgtctg gggccaaggg accacggtca ccgtctcctc agcctccacc    360
aagggcccat cggtcttccc cctggcgccc tgctccagga gcacctccga gagcacagcg    420
gccctgggct gcctgg                                                    436
```

<210> SEQ ID NO 146
<211> LENGTH: 145
<212> TYPE: PRT
<213> ORGANISM: Homo sapiens

<400> SEQUENCE: 146

```
Glu Gln Ser Gly Gly Gly Val Val Gln Pro Gly Arg Ser Leu Arg Leu
 1               5                  10                  15

Ser Cys Ala Ala Ser Gly Phe Thr Phe Ser Ser Tyr Gly Met His Trp
             20                  25                  30

Val Arg Gln Ala Pro Gly Lys Gly Leu Glu Trp Val Ala Val Ile Trp
         35                  40                  45

Tyr Asp Gly Asn Asn Lys Tyr Tyr Ala Asp Ser Val Lys Gly Arg Phe
     50                  55                  60

Thr Ile Ser Arg Asp Thr Ser Lys Asn Thr Leu Tyr Leu Gln Met Asn
 65                  70                  75                  80

Ser Leu Arg Ala Glu Asp Thr Ala Val Tyr Tyr Cys Ala Arg Asp Ser
                 85                  90                  95

Ser Ser Tyr Tyr Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu
145
```

<210> SEQ ID NO 147
<211> LENGTH: 428
<212> TYPE: DNA
<213> ORGANISM: Homo sapiens

<400> SEQUENCE: 147

```
gctccgctac ttctcaccct cctcgctcac tgcacaggtt cttgggccaa ttttatgctg     60
actcagcccc actctgtgtc ggagtctccg gggaagacgg taaccatctc ctgcacccgc    120
agcagtggca gcattgccag caactatgtg cagtggttcc agcagcgccc gggcagttcc    180 ccaccactg taatctatga ggatgaccaa agaccctctg gggtccctga tcggttctgt    240
ggctccatcg acagctcctc caactctgcc tccctcacca tctctggact gaggactgag    300
gacgaggctg actactactg tcagtcttat gatagcagca atcatgtggt attcggcgga    360
gggaccaagc tgaccgtcct aggtcagccc aaggctgccc cctcggtcac tctgttcccg    420
ccctcctc                                                             428
```

<210> SEQ ID NO 148
<211> LENGTH: 142
<212> TYPE: PRT
<213> ORGANISM: Homo sapiens

<400> SEQUENCE: 148

```
Ala Pro Leu Leu Leu Thr Leu Leu Ala His Cys Thr Gly Ser Trp Ala
 1               5                  10                  15
```

Asn Phe Met Leu Thr Gln Pro His Ser Val Ser Glu Ser Pro Gly Lys
                20                  25                  30

Thr Val Thr Ile Ser Cys Thr Arg Ser Ser Gly Ser Ile Ala Ser Asn
            35                  40                  45

Tyr Val Gln Trp Phe Gln Arg Pro Gly Ser Ser Pro Thr Thr Val
    50                  55                  60

Ile Tyr Glu Asp Asp Gln Arg Pro Ser Gly Val Pro Asp Arg Phe Cys
65                  70                  75                  80

Gly Ser Ile Asp Ser Ser Asn Ser Ala Ser Leu Thr Ile Ser Gly
                85                  90                  95

Leu Arg Thr Glu Asp Glu Ala Asp Tyr Tyr Cys Gln Ser Tyr Asp Ser
                100                 105                 110

Ser Asn His Val Val Phe Gly Gly Thr Lys Leu Thr Val Leu Gly
                115                 120                 125

Gln Pro Lys Ala Ala Pro Ser Val Thr Leu Phe Pro Pro Ser
    130                 135                 140

<210> SEQ ID NO 149
<211> LENGTH: 76
<212> TYPE: PRT
<213> ORGANISM: Homo sapiens

<400> SEQUENCE: 149

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Ile Thr
            20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 150
<211> LENGTH: 16
<212> TYPE: PRT
<213> ORGANISM: Homo sapiens

<400> SEQUENCE: 150

Ile Ser Val Gln Arg Leu Ala Ser Tyr Arg Ile Thr Ser Ser Lys
1               5                   10                  15

<210> SEQ ID NO 151
<211> LENGTH: 39
<212> TYPE: PRT
<213> ORGANISM: Homo sapiens

<400> SEQUENCE: 151

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Ile Thr
            20                  25                  30

Ser Ser Lys Cys Pro Lys Glu
            35

<210> SEQ ID NO 152
<211> LENGTH: 26
<212> TYPE: PRT

<213> ORGANISM: Homo sapiens

<400> SEQUENCE: 152

Ile Cys Ala Asp Pro Lys Gln Lys Trp Val Gln Asp Ser Met Asp His
1               5                   10                  15

Leu Asp Lys Gln Thr Gln Thr Pro Lys Thr
            20                  25

<210> SEQ ID NO 153
<211> LENGTH: 11
<212> TYPE: PRT
<213> ORGANISM: Homo sapiens

<400> SEQUENCE: 3

Ala Val Ile Phe Lys Thr Ile Val Ala Lys Glu
1               5                   10

<210> SEQ ID NO 154
<211> LENGTH: 51
<212> TYPE: PRT
<213> ORGANISM: Homo sapiens

<400> SEQUENCE: 154

Asp Ala Ile Asn Ala Pro Val Thr Cys Cys Tyr Asn Phe Thr Asn Arg
1               5                   10                  15

Lys Ile Ser Val Gln Arg Leu Ala Ser Tyr Arg Arg Ile Thr Ser Ser
            20                  25                  30

Lys Cys Pro Lys Glu Ala Val Ile Phe Lys Thr Ile Val Ala Lys Glu
        35                  40                  45

Ile Cys Ala
    50

<210> SEQ ID NO 155
<211> LENGTH: 9
<212> TYPE: PRT
<213> ORGANISM: Homo sapiens

<400> SEQUENCE: 155

Asp Lys Gln Thr Gln Thr Pro Lys Thr
1               5

<210> SEQ ID NO 156
<211> LENGTH: 8
<212> TYPE: PRT
<213> ORGANISM: Homo sapiens

<400> SEQUENCE: 156

Asp Pro Lys Gln Lys Trp Val Gln
1               5

<210> SEQ ID NO 157
<211> LENGTH: 5
<212> TYPE: PRT
<213> ORGANISM: Homo sapiens

<400> SEQUENCE: 157

Ser Val Gln Arg Leu
1               5

<210> SEQ ID NO 158
<211> LENGTH: 19
<212> TYPE: PRT
<213> ORGANISM: Homo sapiens

```
<400> SEQUENCE: 158

Gln Pro Asp Ala Ile Asn Ala Pro Val Thr Cys Cys Tyr Asn Phe Thr
1               5                   10                  15

Asn Arg Lys

<210> SEQ ID NO 159
<211> LENGTH: 11
<212> TYPE: PRT
<213> ORGANISM: Homo sapiens

<400> SEQUENCE: 159

Trp Val Gln Asp Ser Met Asp His Leu Asp Lys
1               5                   10

<210> SEQ ID NO 160
<211> LENGTH: 7
<212> TYPE: PRT
<213> ORGANISM: Homo sapiens

<400> SEQUENCE: 160

Glu Ile Cys Ala Asp Pro Lys
1               5

<210> SEQ ID NO 161
<211> LENGTH: 6
<212> TYPE: PRT
<213> ORGANISM: Homo sapiens

<400> SEQUENCE: 161

Glu Ala Val Ile Phe Lys
1               5

<210> SEQ ID NO 162
<211> LENGTH: 6
<212> TYPE: PRT
<213> ORGANISM: Homo sapiens

<400> SEQUENCE: 162

Gln Thr Gln Thr Pro Lys
1               5

<210> SEQ ID NO 163
<211> LENGTH: 5
<212> TYPE: PRT
<213> ORGANISM: Homo sapiens

<400> SEQUENCE: 163

Thr Ile Val Ala Lys
1               5
```